(12) United States Patent
Lian

(10) Patent No.: US 8,475,463 B2
(45) Date of Patent: Jul. 2, 2013

(54) SYSTEMS AND INSTRUMENTALITIES FOR USE IN TOTAL ANKLE REPLACEMENT SURGERY

(76) Inventor: George J. Lian, Sacramento, CA (US)

(*) Notice: Subject to any disclaimer, the term of this patent is extended or adjusted under 35 U.S.C. 154(b) by 273 days.

(21) Appl. No.: 13/068,290

(22) Filed: May 6, 2011

(65) Prior Publication Data
US 2011/0218542 A1    Sep. 8, 2011

Related U.S. Application Data

(63) Continuation-in-part of application No. 12/798,417, filed on Apr. 2, 2010, now Pat. No. 8,337,503.

(60) Provisional application No. 61/212,533, filed on Apr. 13, 2009, provisional application No. 61/270,203, filed on Jul. 6, 2009, provisional application No. 61/395,017, filed on May 7, 2010, provisional application No. 61/392,013, filed on Oct. 11, 2010.

(51) Int. Cl.
*A61F 5/00* (2006.01)

(52) U.S. Cl.
USPC .......................................... 606/87

(58) Field of Classification Search
USPC .............................. 606/96, 98, 87; 623/21, 18
See application file for complete search history.

(56) References Cited

U.S. PATENT DOCUMENTS

| | | | |
|---|---|---|---|
| 2011/0190829 A1* | 8/2011 | Duggal et al. | 606/301 |
| 2011/0282397 A1* | 11/2011 | Richter et al. | 606/304 |
| 2012/0130434 A1* | 5/2012 | Stemniski | 606/300 |

* cited by examiner

*Primary Examiner* — Sameh Boles
(74) *Attorney, Agent, or Firm* — Dennis A. DeBoo; Audrey A. Millemann; Weintraub, et al.

(57) ABSTRACT

Custom radiographically designed tibial and talar cutting guide system and instrumentalities including a tibial cutting guide position verification device is disclosed. A computer-based system and method for making the custom radiographically designed tibial and talar cutting guides is also disclosed. Further disclosed is an adjustable tibial reaming guide positioning system for allowing a position for reaming of a distal tibia to be adjusted during total ankle replacement surgery and, particularly, during total ankle arthroplasty for prostheses with an intramedullary stem.

16 Claims, 58 Drawing Sheets

| In one embodiment of the invention, a method for manufacturing the custom tibial and talar cutting guides comprises the steps of: |

| 1) Obtaining radiographic data of an ankle of a patient prior to undergoing total ankle replacement surgery; |

| 2) Transforming the radiographic data into a virtual 3-dimensional model of the ankle for obtaining both tibial guide data correlative to a virtual 3-dimensional copy or model of a topography of an anterior surface portion of the distal tibia and talar guide data correlative to a virtual 3-dimensional copy or model of a topography of dome and dorsum surfaces of the talus; |

| 3) Controlling a computer or numerical controlled machine system as a function of the tibial guide data for forming a custom radiographically designed tibial cutting guide comprised of a posterior surface having a first posterior surface portion with a topography that is an inversion or negative of an anterior surface portion of a distal tibia bone bordering three sides of a trapezoidal section of the tibia bone that is to be surgically removed during the total ankle replacement surgery; having a second posterior surface portion trapezoidally shaped and anteriorly depressed relative to the first posterior surface portion for defining a trapezoidally shaped posterior notch in the tibial cutting guide for receiving a tibial reaming guide circumscribing a reamer bit and locating the reamer bit along a central axis of the tibia for use in reaming a blind bore in the tibia along the central axis, and having cutting slits in the guide that borders the trapezoidal shaped second posterior surface for providing guided passage of a saw blade to make a superior tibial cut transversely, a lateral tibial cut, and a medial malleolus cut; and |

| 4) Controlling a computer or numerical controlled machine system as a function of the talar guide data for forming a custom radiographically designed talar cutting guide comprised of a dome member having a inferior surface which is an inversion or negative of a dome surface portion of the talus and a neck member having a posterior surface which is an inversion of a dorsum surface portion of the talus; and having a cutting slit in the neck member for providing guided passage of a saw blade to make a talar or dome cut transversely. |

FIG. 9

SYSTEMS AND INSTRUMENTALITIES FOR USE IN TOTAL ANKLE REPLACEMENT SURGERY

CROSS-REFERENCE TO RELATED APPLICATIONS

This application claims priority under 35 USC Section 119(e) to co-pending U.S. Provisional Patent Application No. 61/395,017, filed May 7, 2010 and to co-pending U.S. Provisional Application No. 61/392,013, filed Oct. 11, 2010, both disclosures of which are incorporated herein by reference in their entireties.

This application is a continuation-in-part patent application of U.S. patent application Ser. No. 12/798,417, filed Apr. 2, 2010, now U.S. Pat. No. 8,337,503 currently pending and which claims priority under 35 USC Section 119(e) to U.S. Provisional Patent Application No. 61/212,533, filed Apr. 13, 2009 and to U.S. Provisional Application No. 61/270,203, filed Jul. 6, 2009, all three disclosures of which are incorporated herein by reference in their entireties.

FIELD OF THE INVENTION

This invention relates generally to systems and instrumentalities for use in total ankle replacement surgery, and, in particular, to a custom radiographically designed cutting guide system and instrumentalities including a tibial cutting guide position verification device, and, further, to an adjustable tibial reaming guide positioning system for allowing a position for reaming of a distal tibia to be adjusted during total ankle replacement surgery and, in particular, during total ankle arthroplasty for prostheses with an intramedullary stem.

BACKGROUND OF THE INVENTION

Total joint replacement is an orthopedic technique in which the diseased ends of bone at a joint are removed and replaced by a combination of metal and plastic prostheses. Joint replacement surgery is done to relieve pain and retain motion of the joint. Total joint replacement is very successful in the larger joints of the lower extremity, the hip and knee. Recently, new techniques and prosthetic designs have made this procedure more common as a treatment option for ankle arthritis.

During total joint replacement surgery precise cuts are made in the ends of the bones by the joint to remove the diseased joint surfaces. A metal appliance, or prosthesis, is then applied on the end of each bone, with a plastic spacer between them. Each joint has its own unique anatomy and functional characteristics. Different prosthetic designs require bone cuts with unique geometry. For the ultimate joint function to be optimal, bone cuts must be accurate so that the prostheses are placed in the proper alignment and orientation.

Currently, there are several designs of total ankle replacement prostheses. One type of total ankle replacement prosthesis is sold by Wright Medical Technology, Inc. (5677 Airline Road, Arlington, Tenn. 38002, USA) under the trademark INBONE Total Ankle System. The INBONE Total Ankle System includes a large intramedullary stem on the tibial side. Although the existing technique used to define the bone cuts for this prosthesis can be accurate, it is very complex thereby rendering it problematic to work with. Specifically, the existing technique or defined algorithm that is used during surgery to determine the alignment and position of cuts in the bone for the correct insertion of this prosthesis is as follows.

First, the anterior ankle is exposed through a longitudinal incision. The leg, ankle and foot are then placed into a leg-holding frame, with the ankle in neutral dorsiflexion and plantarflexion.

The leg is manipulated under fluoroscopy to show a true mortise view. The mortise view is a standard radiographic description of an internally rotated view of the ankle that looks down the axis of the body of the talus between the medial and lateral malleolei. The x-ray beam is perpendicular to the internalleolar axis. In this situation the internalleolar axis is parallel to the top of the operating table. Once this position is established, it is maintained by fixing the foot into the leg holder frame with K-wires drilled through the frame and into the heel.

The long axis of the tibia is then determined using guide rods built into the leg holder frame. Sets of guide rods in the anterior-posterior and medial-lateral planes are manipulated using fluoroscopy to align the long axis of the tibia with the leg holder.

After an incision is made in the bottom of the heel, a drill guide built into the leg holder frame is placed against the undersurface of the calcaneus. The frame and alignment rods are designed to position the drill guide along the central axis of the tibia. A drill bit is used to make a channel up through the calcaneus and talus, and into the distal tibia. This drill bit follows the central axis of the tibia, established by the alignment of the drill guide built into the leg holder frame.

The size of the implants to be used is based on the size of the ankle bones seen on the fluoroscopy views. There are 5 sizes of implant sets and a saw guide that corresponds to each size. Each set of implants comprises a tibial implant, a talar implant and a polyethylene spacer.

The tibial implant is constructed from different components. The inferior part is a tibial tray. This has a set size and morphology specified by the size of the implant set chosen. Superior to this is a base, which also has a set size and morphology specified by the size of the implant set chosen. Superior to this are a variable number and size of stem components that are chosen by the surgeon during the procedure to give the best fit in the tibial intramedullary canal.

The talar component has a set size and morphology specified by the size of the implant set chosen. There is a stem that fits into the inferior portion of the talar implant and extends inferiorly either 10 mm or 14 mm at a defined angle. The choice of which stem length to use is made by the surgeon during the procedure.

Each implant set has a defined number of polyethylene spacers of varying height that fit into the tibial tray on the tibial implant. The height of the spacer to be used is chosen by the surgeon during the procedure, after the tibial and talar components have been fit into the bones.

Additionally, each implant set has a saw guide that corresponds to the size of the implants. Each saw guide has four slits built into it that allow passage of a saw, and define the orientation of the bone cuts. A slit for a superior cut is made in the distal tibia. A parallel inferior cut is made in the superior talus defined by an inferior slit. Oblique medial and lateral cuts are made in the distal tibia and onto the superior talus with the two other slits. When viewed from anterior the guide defines a trapezoidal set of cuts in the ankle.

The saw guide fits into the top of the leg holder frame and can be moved about above the anterior surface of the ankle joint, and will superimpose with the ankle bones when viewed with fluoroscopy. The ankle is still held in the position that gives the mortise view. Using fluoroscopy, the center of the saw guide is aligned with the drill bit in the central axis of the tibia. It is positioned to make parallel superior and inferior cuts that take a similar depth of bone from the dorsum of the talus and inferior surface of the tibia. The medial cut into the medial malleolus should be less than ⅓ of the width of that segment of bone. The lateral cut should just come against the medial surface of the lateral malleolus without cutting into it. When viewed in the medial-lateral plane with fluoroscopy, the cuts should be perpendicular to the long axis of the tibia and the bottom of the foot. The size of saw guide that meets these parameters is then chosen. This determines the size of the implant set to be used.

Once the chosen size saw guide is properly positioned over the anterior ankle, it is stabilized with K-wires drilled through it and into the tibia and talus bones. Then a saw is used to make the tibial and talar cuts through the slits in the guide. The guide is removed and the cut bone segments are also taken out. This leaves a trapezoidal space between the bones into which the implant set will fit.

The distal tibia is then further prepared by reaming along its central axis to accommodate the proper size of the tibial stem. The diameter of the channel to be reamed is determined by the size of the stem to be used. To ream the tibia, the proper diameter reamer bit is put into the ankle space through the anterior wound. A reamer driver is passed through the drill guide against the bottom of the calcaneus, and superiorly through the channel made by the drill bit into the ankle space to meet the reamer bit. After the driver engages the reamer bit, reaming along the central axis of the distal tibia is performed. The frame and guide ensure that the reaming is done with the proper alignment along the central axis.

The talus is finally reamed for the stem of the talar prosthetic component. The position for talar reaming is determined by a guide attached to the frame, and is based on the central axis of the tibia.

Although the above delineated technique is accurate, its complexity has disadvantages. For example, the frame that holds the leg must be constructed sterilely for each patient, a process that takes up valuable operating room time. Additionally, the process of determining the proper alignment of the ankle in the frame prior to cutting the bone is technically exacting, and also time-consuming. There is often a significant amount of fluoroscopic imaging required during the alignment process. Furthermore, all of the equipment used for this procedure must be processed for each separate use.

Another problem with this system, and with all of the existing systems for total ankle replacement, is difficulty in correcting angular deformities that are present. Most arthritis in the ankle is secondary to pre-existing trauma, and it is not uncommon for patients undergoing total ankle replacement to have malalignment at the ankle, or concurrent malalignment in the hindfoot. If an external frame is used to hold the leg, it maintains the relationship between the ankle bones, and the hindfoot, even if there is malalignment. Existing cutting guides used with these systems make both the tibial and talar bone cuts simultaneous with one saw guide. The cuts in the two bones are thus linked and are strictly dependent on the position of each bone relative to the other. Consequently, if an abnormal angular relationship exists between the two bones, it will be maintained after the bone cuts have been made.

Accordingly, there is a need for a system for use in total ankle replacement surgery that overcomes the significant shortcomings of the known prior-art as delineated hereinabove.

BRIEF SUMMARY OF THE INVENTION

Accordingly, and in one aspect, an embodiment of the invention ameliorates or overcomes one or more of the significant shortcomings of the known prior art by providing a system comprised of custom guides defined by preoperative CAT scan or MRI scan analysis and a set of instrumentalities for use with the custom guides. In one aspect, the system improves the precision of bone cuts, eliminates the need for a large external frame to hold the ankle immobile, simplifies the operative procedure, decreases the operative time, minimizes the need for intra-operative fluoroscopy and allows better correction of deformities by independent bone cuts and reaming of the tibia and talus bones.

One important difference between the ankle and knee for joint replacement surgery is the exposure of the bones for cutting and reaming. During joint replacement surgery for each an anterior longitudinal incision is made to expose the bones at the joint. For the knee, this approach leads to the convex side of the joint. This places the ends of the bones external to the skin, a position that makes them easily accessible for the cutting guides. For the ankle, the anterior approach leads to the concave side of the joint. The ends of the bones thus remain interior as they are being prepared during the surgery. Hence, different types of instruments must therefore be used when performing ankle joint replacement surgery.

More particularly, and in one aspect, an embodiment of the invention provides a custom radiographically designed cutting guide system for use in total ankle replacement surgery, the system comprising: a tibial cutting guide having a first posterior surface portion with a topography that is a preoperatively defined negative of an anterior topography of a distal portion of a tibia of a patient to fit the first posterior surface portion of the tibial cutting guide to the distal portion of the tibia in one unique position; the tibial cutting guide having a second posterior surface portion anteriorly recessed from the first posterior surface portion at a preoperatively defined distance from a central longitudinal axis of the tibia for defining a tibial reaming guide locator notch anteriorly recessed from the first posterior surface portion; and the tibial cutting guide having at least one slit to guide a cutting instrument to make at least one cut in the distal portion of the tibia of the patient with the tibial cutting guide in the one unique position wherein at least the one cut is in a boundary of a segment of the distal portion of the tibia to resect during total ankle replacement surgery.

Additionally, an embodiment of the invention provides a computer-based method for making the custom radiographically designed tibial cutting guide.

In another aspect, an embodiment of the invention provides a custom radiographically designed cutting guide system for use in total ankle replacement surgery, the system comprising: a talar cutting guide comprised of a dome member and a neck member; the dome member having an inferior surface portion with a topography that is a preoperatively defined negative of a topography of at least a portion of a dome surface of a dome of a talus of a patient to fit the inferior surface portion of the dome member to at least the portion of the dome surface of the dome of the talus in one unique position; and the neck member having a posterior surface portion with a topography that is a preoperatively defined negative of a topography of at least a portion of a dorsum surface of a talar neck of the talus to fit the posterior surface portion of the neck member to at least the portion of the dorsum surface of the talar neck of the talus in one unique position.

Additionally, an embodiment of the invention provides a computer-based method for making the custom radiographically designed talar cutting guide.

In another aspect, an embodiment of the invention provides a custom radiographically designed cutting guide system for use in total ankle replacement surgery, the system comprising: a tibial reaming guide sized to fit in a space formed by a resected segment of a distal portion of a tibia and a resected segment of a dome of a talus, the tibial reaming guide having a opened ended channel; a cannulated reaming bit removably received within the opened ended channel of the tibial reaming guide; and the cannulated reaming bit having a bone reaming exterior surface for forming a bore in the tibia when driven wherein the bore is sized to receive an intramedullary stem of a preoperatively chosen total ankle prosthesis.

In yet another aspect, an embodiment of the invention provides an adjustable tibial reaming guide positioning system for allowing a position for reaming of a distal tibia to be adjusted during total ankle arthroplasty for prostheses with an intramedullary stem, the system comprising: a tibial reaming guide having a reamer body sized to fit in a space formed by a resected segment of a distal portion of a tibia and a resected segment of a dome of a talus, the reamer body having an opened ended channel for removeably receiving a cannulated reaming bit, the opened ended channel having a central longitudinal axis; and means, operatively coupled to the tibial reaming guide, for incrementally adjusting a position of the tibial reaming guide in the space formed by the resected segment of the distal portion of the tibia and the resected segment of the dome of the talus for locating the central longitudinal axis of the opened ended channel of the tibial reaming guide relative to a central longitudinal axis of the distal portion of the tibia during total ankle arthroplasty for prostheses with an intramedullary stem.

In a further aspect, an embodiment of the invention provides a tibial cutting guide position verification system for use in total ankle replacement surgery.

In yet a further aspect, an embodiment of the invention provides radiographic guide device for providing position verification of a tibial cutting guide utilized during total ankle replacement surgery, the radiographic guide device comprising: an elongated body formed from a radiolucent material and disposed at least partially within a tibial cutting guide, the elongated body extending between a posterior end and an anterior end and having a central longitudinal axis; a radiodense element disposed within the elongated body at a location proximate the posterior end of the elongated body; and a radiodense ring circumscribing the anterior end of the elongated body wherein a display of a position of the radiodense element relative to the radiodense ring is provided by an x-ray beam shooting directly along the central longitudinal axis of the elongated body from a position anterior to the radiodense ring.

Accordingly, having thus summarized the invention, it should be apparent that numerous modifications and adaptations may be resorted to without departing from the scope and fair meaning of the present invention as set forth hereinbelow by the claims.

BRIEF DESCRIPTION OF THE DRAWINGS

FIG. 9 is a general flowchart view of an embodiment of a method for producing the custom tibial cutting guide and the custom talar cutting guide with a manufacturing system generally presented in the block diagram illustrated in FIG. 8.

DETAILED DESCRIPTION OF THE INVENTION

Figure 1:
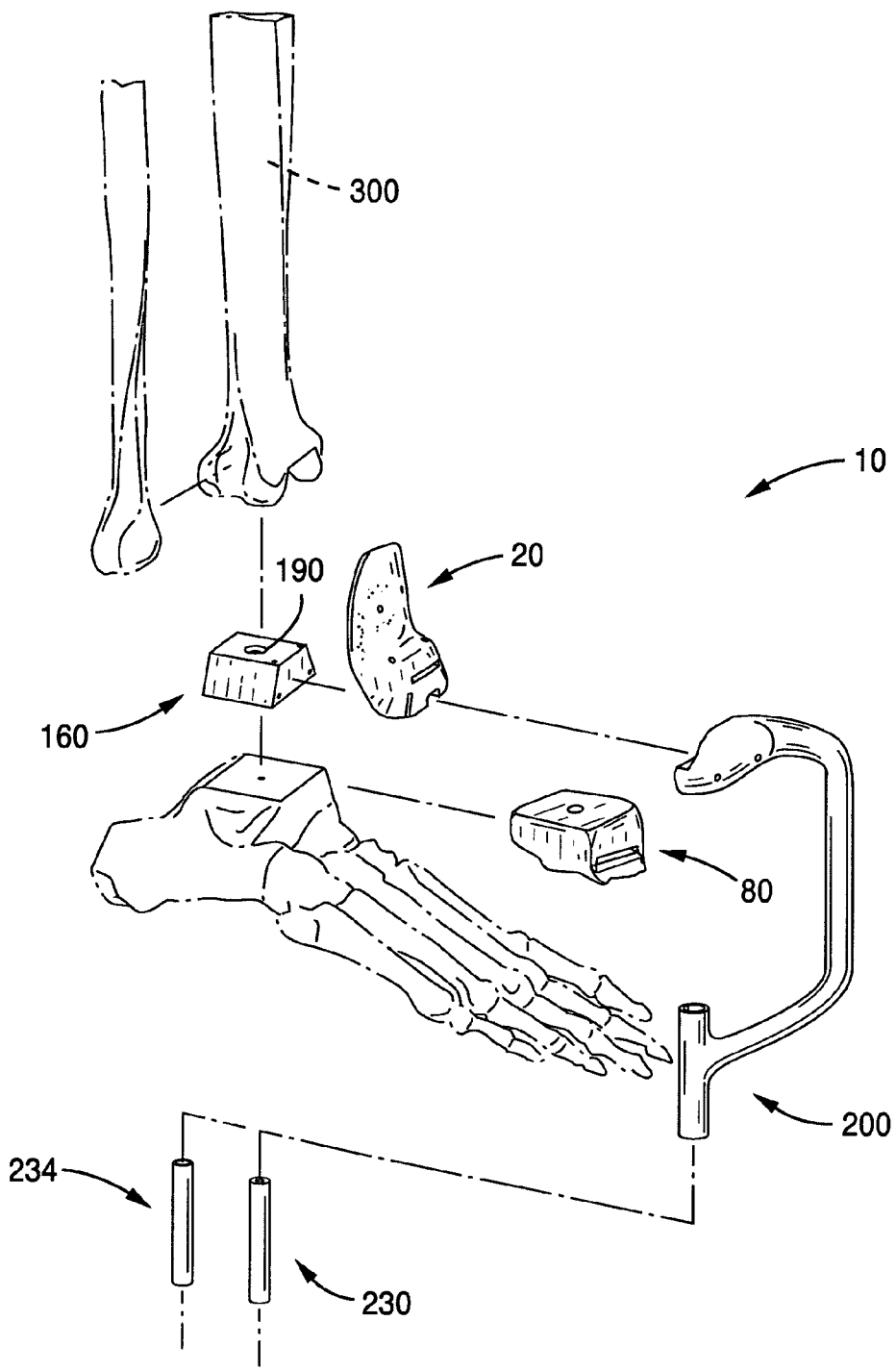
FIG. 1 is a front and side perspective view of a system for use in total ankle replacement surgery, the system comprising a custom tibial cutting guide, a custom talar cutting guide, a tibial reaming guide circumscribing a removable, cannulated reaming bit, a C-shaped outrigger alignment guide, a cylindrically shaped inner sleeve wire guide, and a cylindrically shaped inner sleeve drill and driver bit guide, and further illustrating a fragmentary front and side perspective view of a human leg and foot illustrating an ankle joint comprised of a fibula and a prepared tibia of the leg, and a prepared talus of the top of the foot.

Considering the drawings, wherein like reference numerals denote like parts throughout the various drawing figures, reference numeral 10 is directed to a system for use in total ankle replacement surgery.

Referring to FIG. 1, and in one embodiment, the system 10 is comprised of a set of two patient-specific, radiographically designed, custom-made cutting guides: a custom tibial cutting guide 20 and a custom talar cutting guide 80. Additionally, the system 10 is comprised of a tibial reaming guide 160 circumscribing and aligning a removable, cannulated reaming bit 190. The system 10 is further comprised of a C-shaped outrigger alignment guide 200 that receives two removable, alternate inner sleeve guides: a cylindrically shaped inner sleeve wire guide 230 and a cylindrically shaped inner sleeve drill and driver bit guide 234. Moreover, and referring to FIGS. 15 and 17, the system 10 is comprised of a skeleton cage or first frame member 240 and a double fork cage or second frame member 260 for use during prosthesis placement.

Custom Tibial Cutting Guide 20

Figure 2:
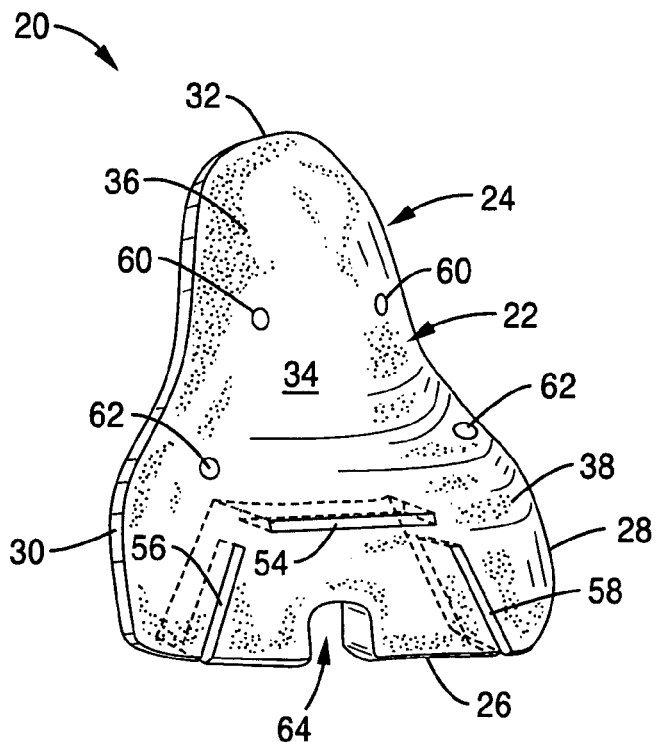
FIG. 2 is a front perspective view of a custom tibial cutting guide illustrating bone fixation holes, tibial reaming guide alignment holes, saw cutting slits, and an outrigger alignment guide keyway notch.

More specifically, and referring to FIGS. 1 and 2, the custom tibial cutting guide 20 is comprised of a generally half-bell-shaped body 22 having a generally bell-shaped peripheral edge 24.

The generally bell-shaped peripheral edge 24 is comprised of a generally flat distal edge 26 transitioning at one end to a proximally extending, curved shaped inner edge 28 and transitioning at the other end to a proximally extending, curved shaped outer edge 30. The generally bell-shaped peripheral edge 24 is further comprised of a rounded proximal edge 32 bridging the proximal ends of the inner and outer edges 28, 30 together. The "half-bell-shaped" as used herein refers to a general shape of a bell having an outwardly flaring opening and bisected by a plain parallel to the bell's longitudinal axis.

The generally half-bell-shaped body 22 is comprised of an anterior surface 34 circumscribed by the generally bell-shaped peripheral edge 24. The anterior surface 34 is comprised of a proximally tapered convex anterior surface portion 36 integrally formed with a distally flared bulbous anterior surface portion 38. The proximally tapered convex anterior surface portion 36 distally extends from the rounded proximal edge 32 while widening and then transitioning into the distally flared bulbous anterior surface portion 38 which terminates into the generally flat distal edge 26.

Figure 3:
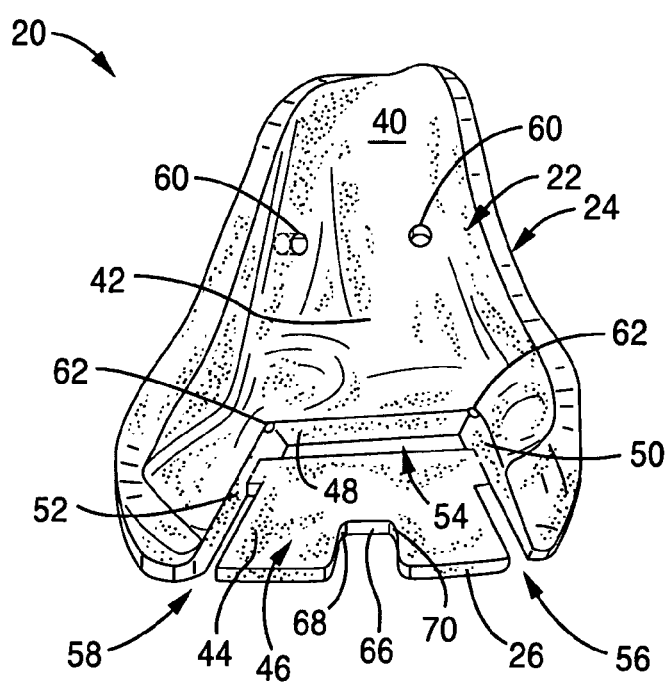
FIG. 3 is a back perspective view of the custom tibial cutting guide illustrating bone fixation holes, tibial reaming guide alignment holes, saw cutting slits, the outrigger alignment guide keyway notch, a reaming guide locator notch, and a posterior surface that has a patient specific topography that is a preoperatively defined negative or inversion of an anterior topography or surface of a distal portion of the patient's tibia.
Figure 4:
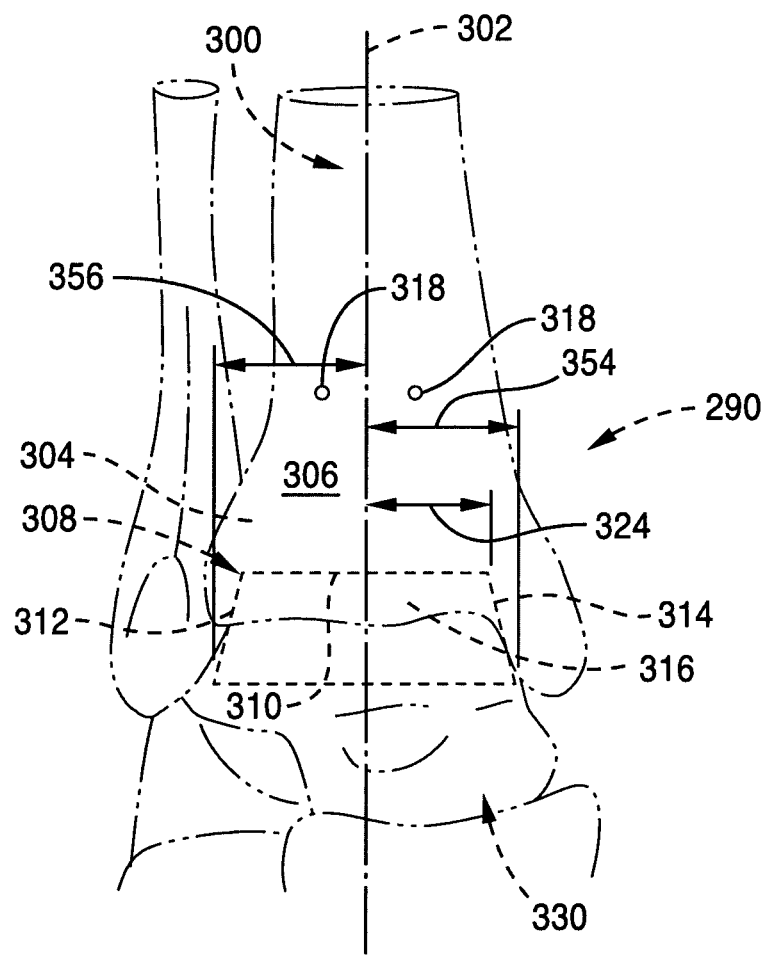
FIG. 4 is a fragmentary front elevational view of a human leg and foot illustrating an ankle joint comprised of a tibia and fibula bone of the leg, and a talus bone of the top of the foot and further illustrating a central axis of the distal tibia and a bone preparation area outlined by a broken line trapezoid.
Figure 5:
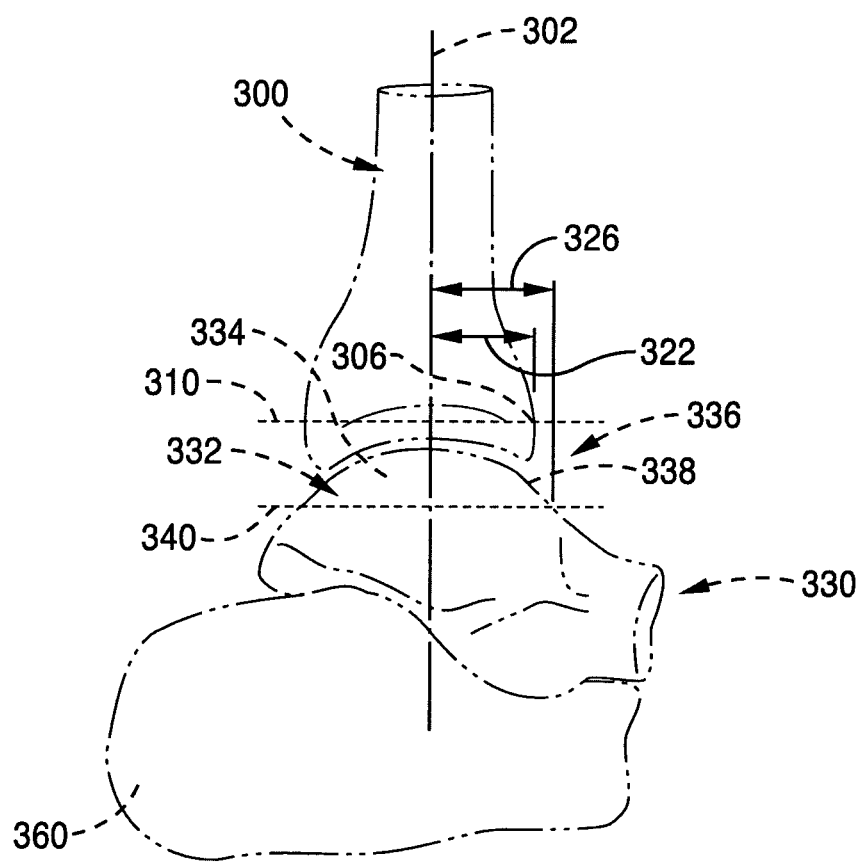
FIG. 5 is a fragmentary side elevational view of the tibia bone of the leg and the talus bone of the top of the foot and further illustrating the central axis of the distal tibia and illustrating, in broken lines, a central long axis of the distal tibia, a tibia bone cut location, and a talus bone cut location.

Additionally, and referring to FIGS. 3 through 5, the generally half-bell-shaped body 22 is comprised of a posterior surface 40 circumscribed by the generally bell-shaped peripheral edge 24. The posterior surface 40 is comprised of a first posterior surface portion 42 that has a topography that is a preoperatively defined inversion or negative of an anterior surface portion 306 of a distal portion 304 of a tibia 300 to which the custom tibial cutting guide 20 is fitted in one unique position during the total ankle replacement surgery. The first posterior surface portion 42 borders a superior base side and portions of two non-parallel sides of a broken line trapezoidal section 308 that outlines a trapezoidal portion of the tibia 300 and a talus 330 that is to be surgically removed or resected during the total ankle replacement surgery as will be further detailed below.

The posterior surface 40 of the body 22 is further comprised of a second posterior surface portion 44 that is trapezoidally shaped and anteriorly recessed relative to the first posterior surface portion 42 for defining a trapezoidally shaped posterior locator notch or reaming guide locator notch 46 in the custom tibial cutting guide 20. The reaming guide locator notch 46 is defined by the trapezoidally shaped second posterior surface portion 44, a superior base surface 48, an angled lateral or outer surface 50, and an angled medial or inner surface 52 wherein the superior base surface 48, angled lateral or outer surface 50, and angled medial or inner surface 52 generally extend perpendicularly between the first and second posterior surfaces 42, 44 of the custom tibial cutting guide 20. Accordingly, the reaming guide locator notch 46 extends between the generally flat distal edge 26 and the superior base surface 48, and between the angled outer and inner surfaces 50 and 52 thereby outlining the trapezoidal section 316 of the distal portion 304 of the tibia 300 that is surgically removed during the total ankle replacement surgery.

Figure 20:
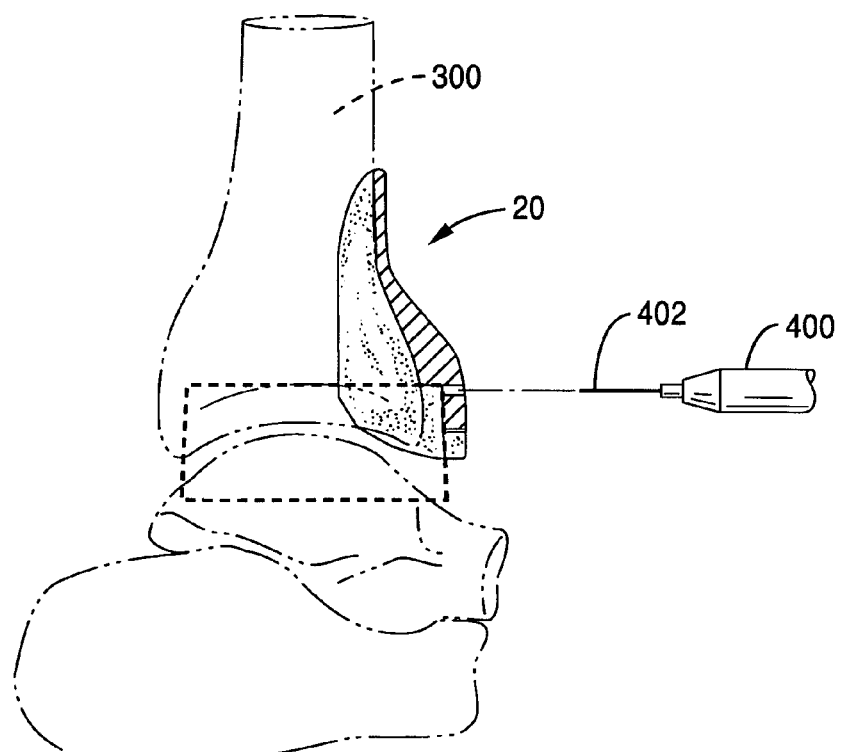
FIG. 20 is a side sectional view of the custom tibial cutting guide fit in place against the anterior surface of the distal tibia and further illustrating a tibia bone cut location in broken line and a conventional surgical saw and blade.
Figure 21:
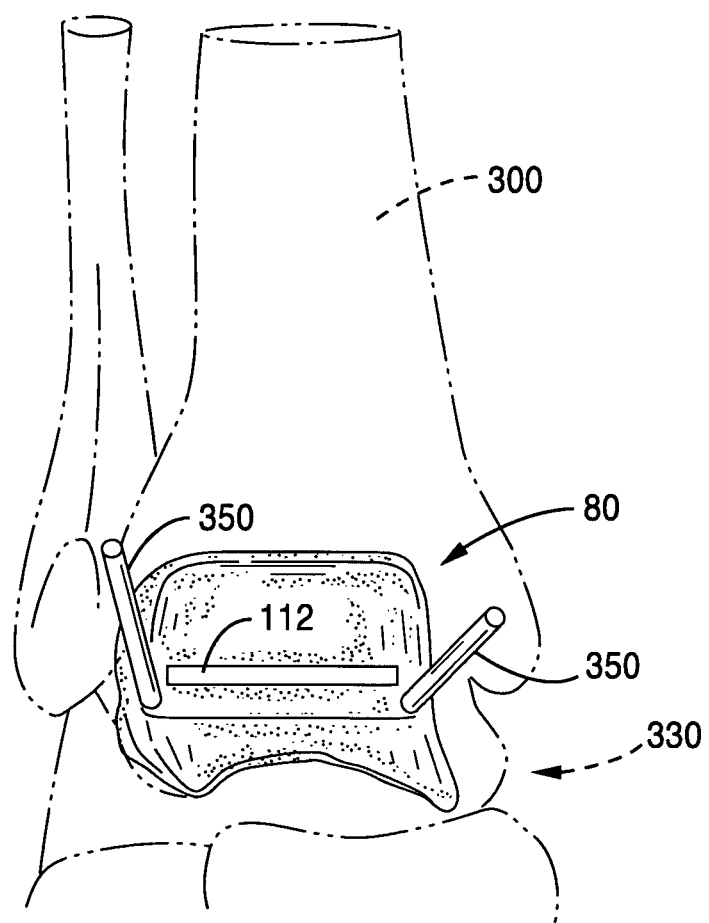
FIG. 21 is a front elevational view of the custom talar cutting guide shown fit in place against the superior surface of the dome of the talus and the anterior surface of the dorsum of the talar neck and removably secured thereto for use with a surgical saw and blade.
Figure 24:
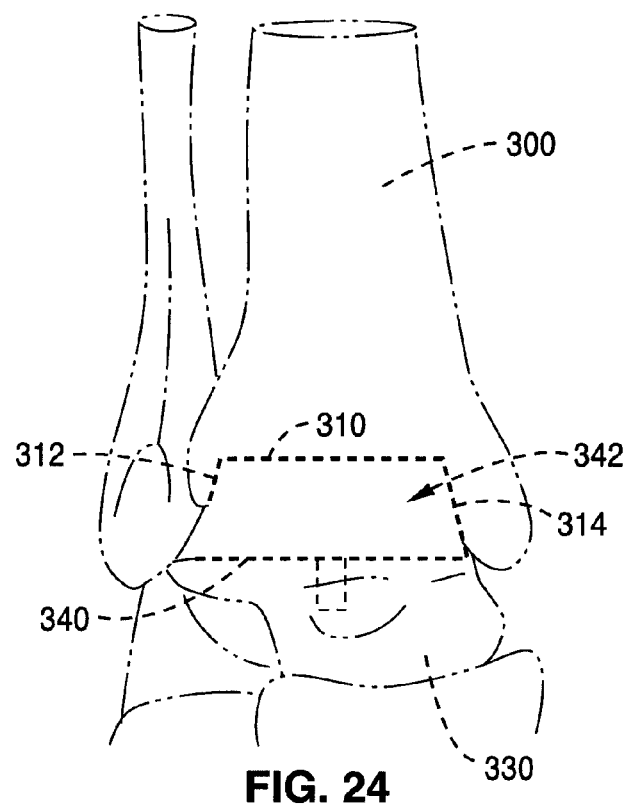
FIG. 24 is a fragmentary front elevational view of the ankle joint and further illustrating the tibia and talus bone cuts, the tibial-talar space, and the talar blind bore in broken line.

Additionally, the superior base surface 48 defines a superior base edge of a preoperatively located superior tibial cutting slit 54 disposed through the cutting guide 20 for guiding the passage of a saw blade 402 of a surgical saw 400 (FIG. 20) to make a superior tibial cut 310 transversely (FIGS. 4 and 24). The angled lateral surface 50 defines a lateral side edge of a preoperatively located lateral cutting slit 56 disposed through the cutting guide 20 for guiding the passage of the saw blade 402 to make the lateral tibial cut 312 (FIGS. 4 and 24). The angled medial surfaces 52 defines a medial side edge of a preoperatively located medial malleolus cutting slit 58 disposed through the cutting guide 20 for guiding the passage of the saw blade 402 to make the medial malleolus cut 314 (FIGS. 4 and 24) thereby defining three cutting zones of the distal portion 304 of tibia 300 for removing the trapezoidal section 316 of the distal portion 304 of the tibia 300 during the total ankle replacement surgery.

Figure 19:
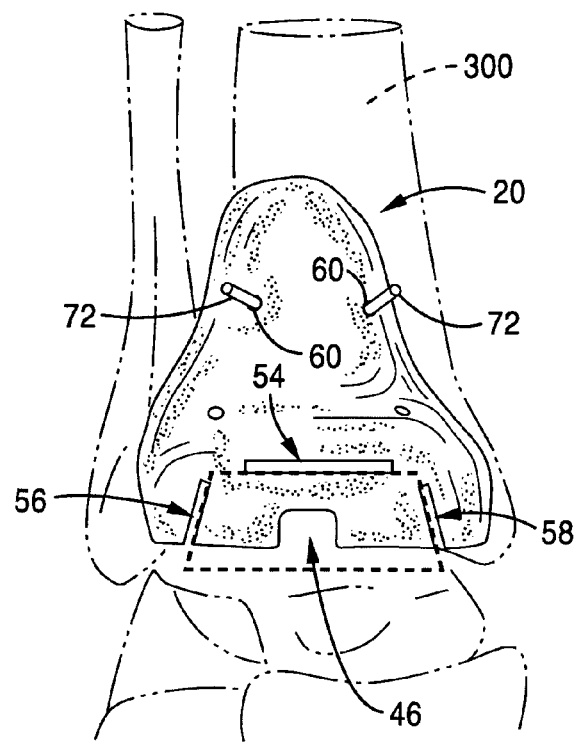
FIG. 19 is a front elevational view of the custom tibial cutting guide fit in place against the anterior surface of the distal portion of the tibia or the distal tibia and removably secured thereto.
Figure 25:
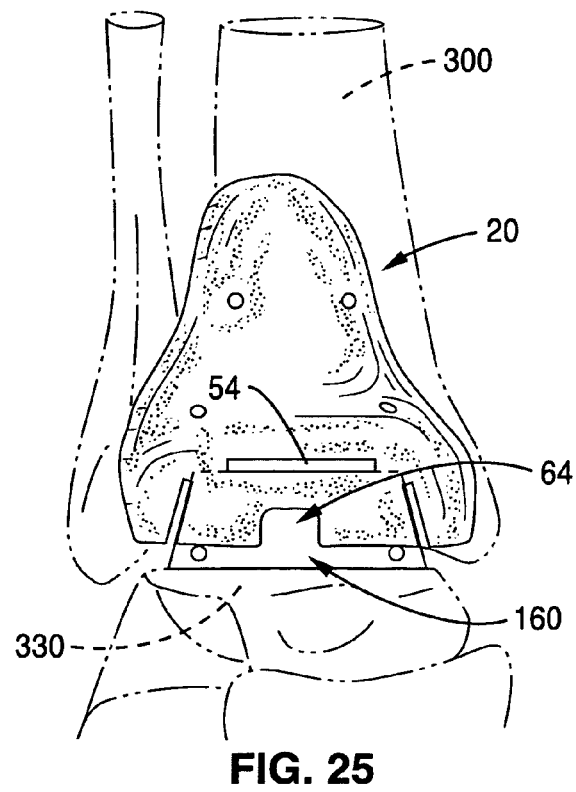
FIG. 25 is a front elevational view of the custom tibial cutting guide fit in place against the anterior surface of the distal tibia and fitted with the tibial reaming guide.

Furthermore, and referring to FIGS. 2 and 3, the custom tibial cutting guide 20 is comprised of a plurality of bone fixation holes 60 and reaming guide fixation holes 62. In one embodiment, two spaced apart bone fixation holes 60 pass through the generally half-bell-shaped body 22 of the custom tibial cutting guide 20 from the proximally tapered convex anterior surface portion 36 to the first posterior surface portion 42 for placement of wires or screws for the temporary fixation (FIG. 19) of the custom tibial cutting guide 20 to the distal portion 304 of the tibia 300 via tibia holes 318 (FIG. 4). Additionally, and in one embodiment, two spaced apart reaming guide fixation holes 62 pass through the generally half-bell-shaped body 22 of the custom tibial cutting guide 20 from the distally flared bulbous anterior surface portion 38 to the superior base surface 48 for placement of wires or screws for the temporary fixation of the tibial reaming guide 160 via holes 180 (FIGS. 10 and 25) into the reaming guide locator notch 46 of the custom tibial cutting guide 20 as will be further detailed below.

Moreover, and referring to FIGS. 2 and 3, the custom tibial cutting guide 20 is comprised of a preoperatively placed outrigger alignment guide locator notch 64 disposed through the generally half-bell-shaped body 22 of the custom tibial cutting guide 20. The outrigger alignment guide locator notch 64 extends from the distally flared bulbous anterior surface portion 38 to the trapezoidally shaped second posterior surface 44 while interrupting the generally flat distal edge 26. In one embodiment, the outrigger alignment guide locator notch 64 is defined by three outrigger guide locator notch surfaces: a superior notch surface 66, an inner notch surface 68, and outer notch surface 70 wherein the inner notch surface 68 generally normally depends distally from one end of the superior notch surface 66 while the outer notch surface 70 generally normally depends distally from the other end of the superior notch surface 66. In one embodiment, the outrigger alignment guide locator notch 64 is parallel to a central axis 302 of the tibia 300.

Custom Talar Cutting Guide 80

Figure 6:
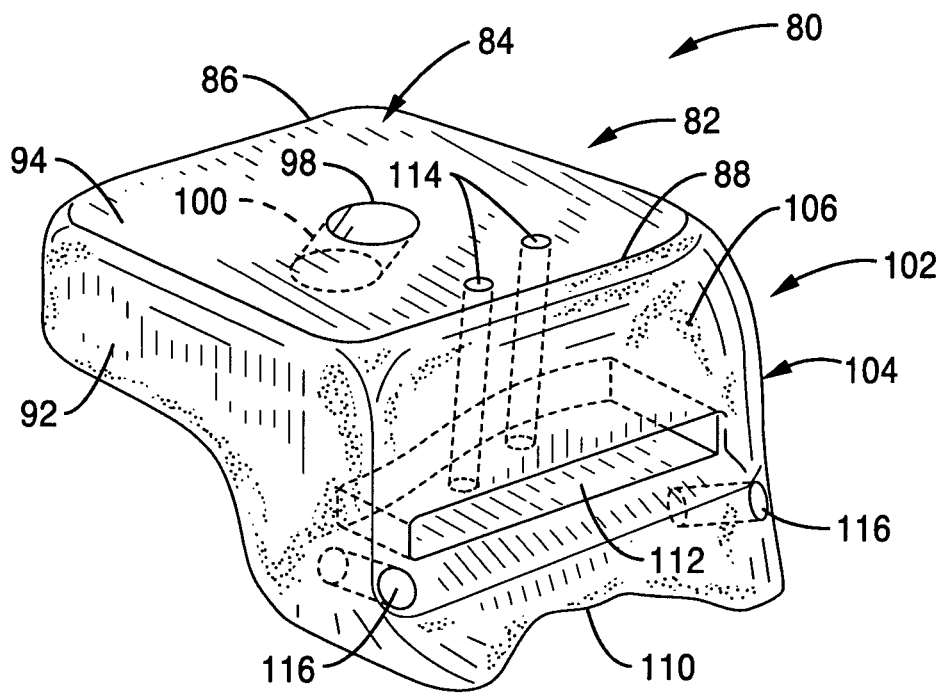
FIG. 6 is a top, front, and side perspective view of a custom talar cutting guide illustrating bone fixation holes, a saw cutting slit, and an angled reaming channel.
Figure 7:
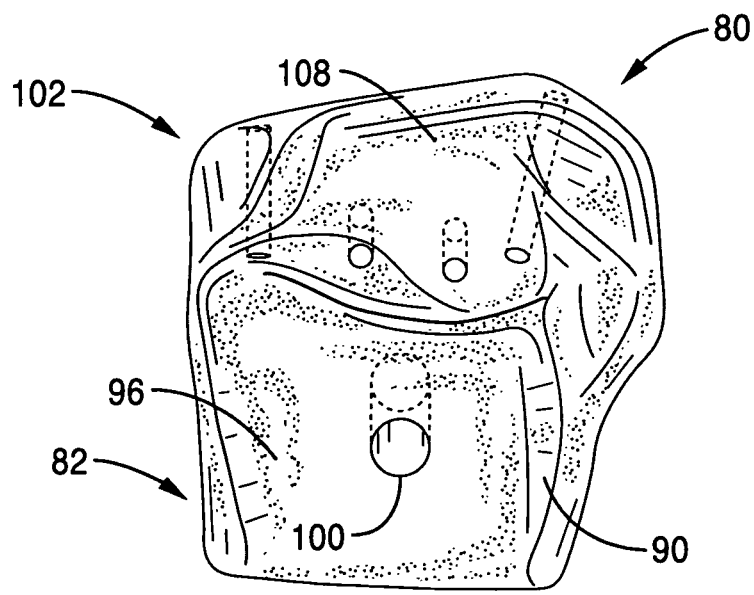
FIG. 7 is a bottom and back perspective view of the custom talar cutting guide illustrating an inferior surface and a posterior surface of the talar custom cutting guide that have patient specific topography that are, respectively, a preoperatively defined negative or inversion of a topography of a dome of the patient's talus and of a topography of a dorsum of a talar neck of the patient's talus and further illustrating the bone fixation holes and the angled reaming channel.

Referring to FIGS. 6 and 7, the custom talar cutting guide 80 is generally L-shaped in configuration and is comprised of a dome member 82 and a neck member 102 integrally formed therewith.

The dome member 82 is comprised of a generally rectangularly shaped body 84 longitudinally extending between a posterior end 86 and an anterior end 88 and laterally extending between a distally extending inner sidewall 90 and a distally extending outer sidewall 92. Additionally, the generally rectangularly shaped body 84 includes a superior or upper surface 94 and inferior or lower surface 96. The superior or upper surface 94 is generally flat and the inferior or lower surface 96 has a topography that is a preoperatively defined inversion or negative of the topography of a dome surface 334 of a dome 332 of a talus 330 (FIG. 5) on which it is mounted during the total ankle replacement surgery.

The generally rectangularly shaped body 84 is further comprised of an open ended, angled reaming channel or bore 98 that is disposed through the body 84 at a preoperatively defined location and at a preoperatively defined angle. The angled reaming channel or bore 98 is defined by a cylindrically shaped interior surface 100 that angularly extends posteriorly from the superior surface 94 to the inferior surface 96 at the preoperatively defined angle.

The neck member 102 is integrally formed with and distally depends from the anterior end 88 of the dome member 82. The neck member 102 is comprised of a generally rectangularly shaped body 104 comprised of an anterior or outer surface 106 and a posterior or inner surface 108. The anterior surface 106 of the neck member 102 generally perpendicularly extends distally from the superior surface 94 of the dome member 82. The posterior surface 108 of the neck member 102 comprises a topography that is a preoperatively defined inversion or negative of topography of a dorsum surface 338 of a talar neck 336 of the talus 330 (FIG. 5) to which it is to be received. The anterior and posterior surfaces 106, 108 distally terminate to a distal end surface 110 having a topography that is a preoperatively defined inversion or negative of the topography of a portion of the dorsum surface 338 of a talar neck 336 of the talus 330 on which it is fitted.

Additionally, the neck member 102 is comprised of a preoperatively sized and located talus cutting slit 112 disposed therethrough to guide the passage of a saw blade 406 powered by a surgical saw 400 (FIG. 22) for cutting the top of the talus along the talus cut line 340 (FIG. 5) during the total ankle replacement surgery.

Furthermore, the neck member 102 is comprised of a plurality of dome fixation holes 114 and neck fixation holes 116 as illustrated in FIG. 6. In one embodiment, two spaced apart dome fixation holes 114 pass through the superior surface 94 of the dome member 82 and pass through the generally rectangularly shaped body 104 of the neck member 102 at a location superior to the cutting slit 112 for allowing placement of wires or screws 346 for temporary fixation into the dome 332 via holes 348 (FIG. 23).

Figure 23:
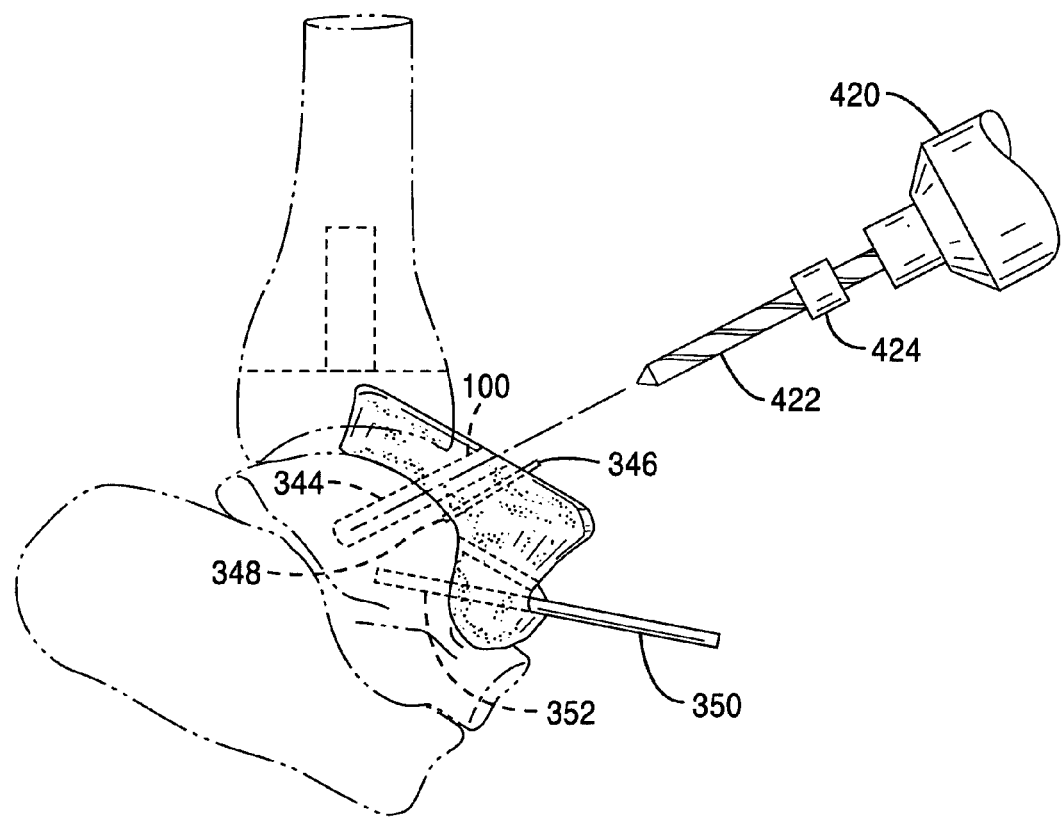
FIG. 23 is a side elevational view of the custom talar cutting guide shown fit in place against the superior surface of the dome of the talus and the anterior surface of the dorsum of the talar neck and removably secured thereto, and further illustrating the talar bone blind bore location in broken line and a conventional surgical drill and bit.

Additionally, and in one embodiment, two spaced apart neck fixation holes 116 pass through the generally rectangularly shaped body 104 of the neck member 102 at a location inferior to the cutting slit 112 for allowing placement of wires or screws 350 for temporary fixation into the dome 332 via holes 352 (FIG. 23).

System and Method for Manufacturing Custom Guides 20 and 80

Figure 8:
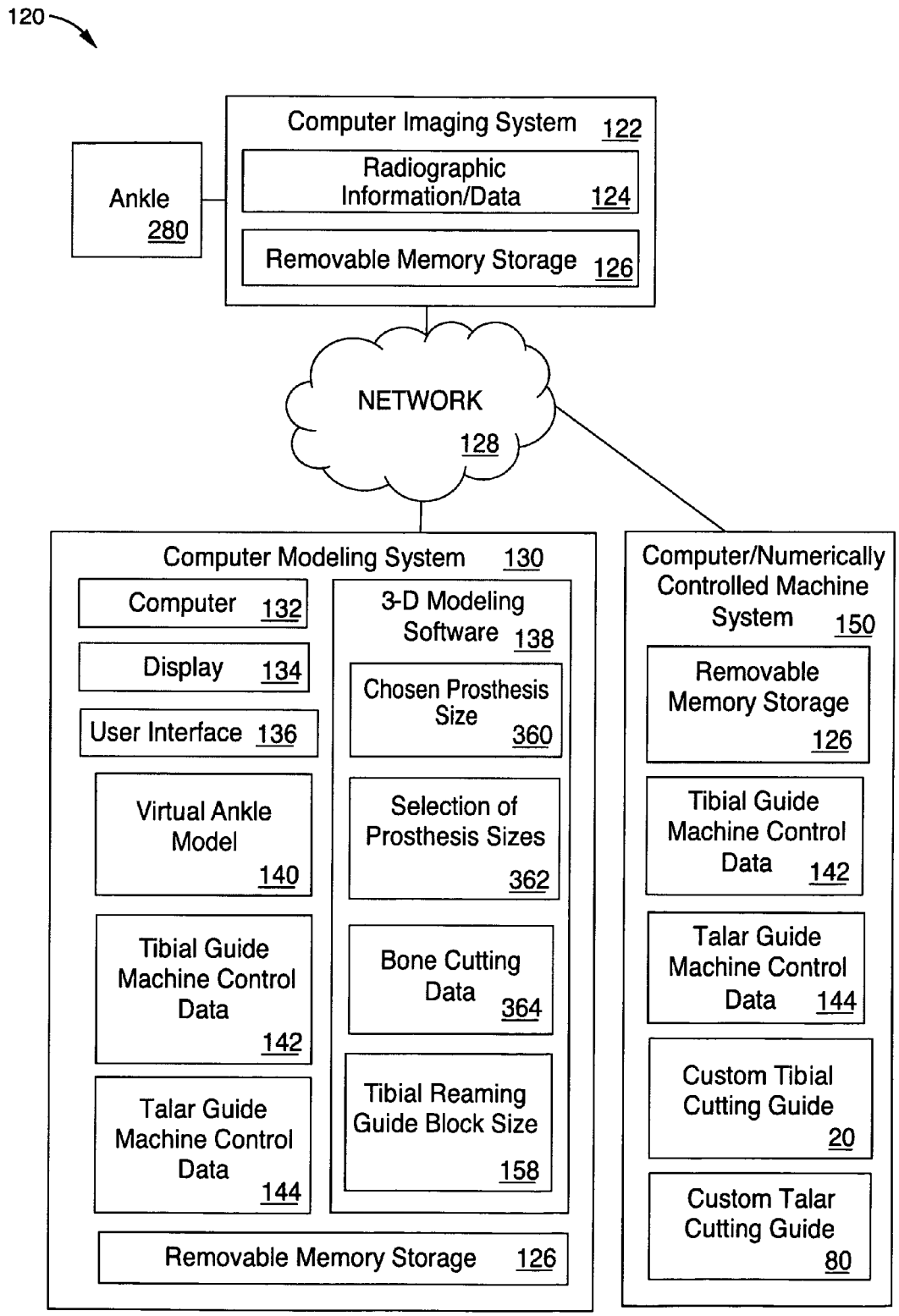
FIG. 8 is a general block diagram of a manufacturing system for producing the custom tibial cutting guide and the custom talar cutting guide.

In one embodiment, FIG. 8 illustrates a general block diagram of a manufacturing system 120 for producing the custom tibial cutting guide 20 and the custom talar cutting guide 80 in accordance with a method described below and generally illustrated via flow chart in FIG. 9.

Referring to FIG. 8, the system 120 is comprised of a computer imaging system 122 such as a CAT and/or a MRI system for obtaining radiographic information or data 124 of the patient's ankle 290 (FIG. 4). Additionally, the system 120 is comprised of a computer modeling system 130 comprised of, for example, a computer 132 having a display 134, a user interface or input apparatus 136 such as a keyboard and mouse, and existing 3-D modeling software 138 configured to operate on the computer 132. Furthermore, the system 120 is comprised of a computer or numerically controlled machine system 150 for manufacturing the custom tibial and talar cutting guides 20, 80 by, for example, a molding and milling process.

In general, and prior to surgery, the morphology of the patient's ankle 290 being replaced is assessed radiographically using the computer imaging system 122 for obtaining radiographic information or data 124. This radiographic information or data is used to render a virtual 3-dimensional copy or model 140 of the ankle 290 with the existing 3-D modeling software 138 of the computer modeling system 130. The 3-D modeling software 138 then analyzes the virtual ankle model 140 and chooses one of a plurality of available sizes of existing prostheses (for example, prostheses 370 illustrated in FIG. 30) and determines where the bones should be cut and reamed as a function of the radiographical analysis of the ankle 290 and the chosen size of the prosthesis. Accordingly, existing considerations are used in choosing one of the plurality of available sizes of existing prostheses and in determining the associated bone cuts correlative to the chosen size of the prosthesis; however, instead of the analysis being done during the surgical procedure, it is done preoperatively by utilizing the radiographic information or data 124 obtained by the computer imaging system 122 and the analysis provided by the computer modeling system 130.

Figure 22:
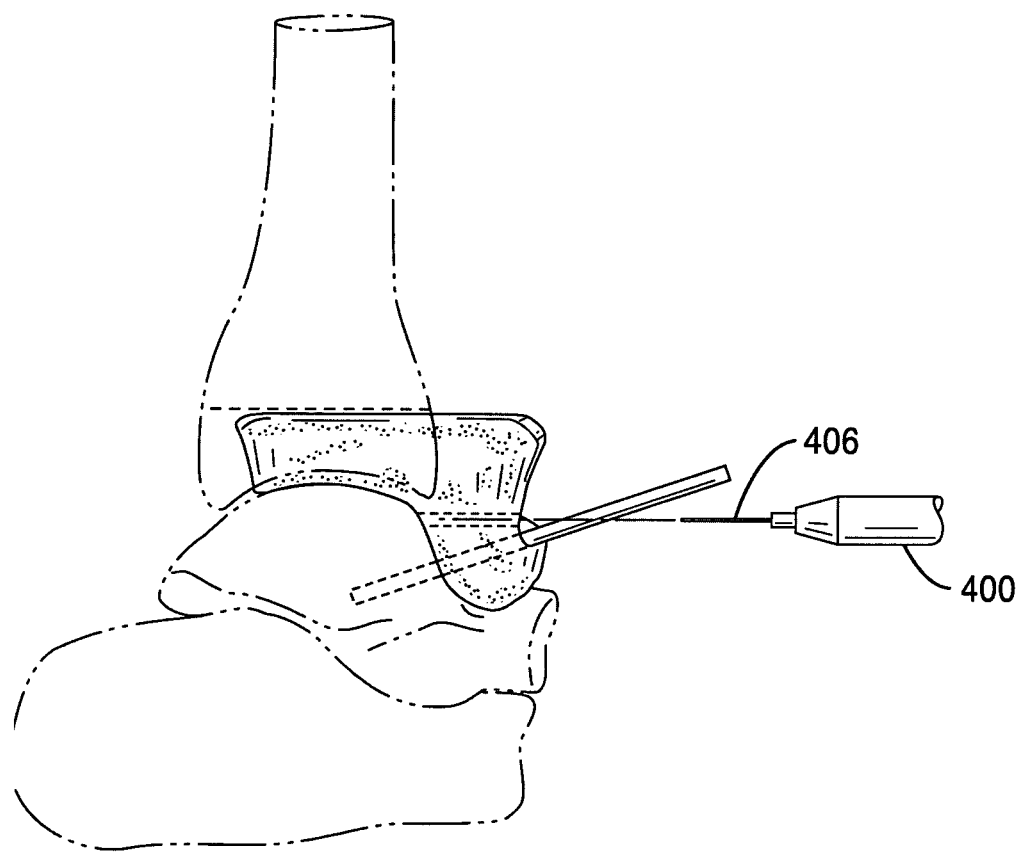
FIG. 22 is a side elevational view of the custom talar cutting guide shown fit in place against the superior surface of the dome of the talus and the anterior surface of the dorsum of the talar neck and removably secured thereto, and further illustrating a conventional surgical saw and blade for making the talar bone cut.

The computer or numerically controlled machine system 150 molds the custom tibial cutting guide 20 out of, for example, plastic and mills the guide 20 to fit precisely against the anterior border or surface portion 306 of the distal portion 304 of the tibia 300 (FIGS. 4, 19 and 20) as a function of tibial guide machine control data 142. Additionally, and as a function of talar guide machine control data 144, the computer or numerically controlled machine system 150 molds the custom talar cutting guide 80 out of, for example, plastic and mills the guide 80 to fit precisely on the dome surface 334 of the dome 332 of the talus 330 and against the dorsum surface 338 of the talar neck 336 of the talus 330 (FIGS. 5 and 22). Like a lock, the respective surfaces 42, 96, and 108 of the custom tibial and talar cutting guides 20, 80 match their respective bone surfaces in one unique position. Additionally, these plastic custom cutting guides 20, 80 are milled with precisely oriented slits that guide the position of saw blades, and holes for drill bits, reamer bits, and fixation pins or screws. When each guide 20, 80 is coupled to its respective bone in its unique position, the holes and slits are in the preoperatively determined position for each of them.

More specifically, and referring to FIGS. 8 and 9, an embodiment of a method for manufacturing the custom tibial cutting guide 20 and the custom talar cutting guide 80 comprises the following steps.

A step of operating the computer imaging system 122 for obtaining radiographic information or data 124 of the ankle 290 of the patient correlative to the morphology of the ankle 290 of the patient and prior to the patient undergoing total ankle replacement surgery.

A step of communicating the obtained radiographic information or data 124 from the computer imaging system 122 to the computer modeling system 130 via a removable memory storage medium 126 and/or via an interconnected network 128.

A step of utilizing the 3-D modeling software 138 for transforming the radiographic information or data 124 into a virtual 3-dimensional copy or model 140 of the ankle 290 and for analyzing and transforming the virtual 3-dimensional model 140 of the ankle as a function of known and computed criteria for obtaining tibial guide machine control data 142 and talar guide machine control data 144 for use in manufacturing the custom tibial and talar cutting guides 20, 80 thereby ultimately transforming the radiographic information or data 124 into the custom tibial and talar cutting guides 20, 80

In one embodiment, the known and computed criteria includes: choosing a proper prosthesis size 360 from a selection of prosthesis sizes 362 as a function of the virtual 3-dimensional ankle model 140. In one embodiment, the proper prosthesis size 360 is chosen from five different sizes of prosthesis currently available in the INBONE Total Ankle System wherein each size has an corresponding bone cutting guide template for use therewith and that is employed to define bone cutting data 364; determining the long central axis 302 (FIG. 4) of the tibia 300 of the patient as a function of the virtual 3-dimensional model 140 of the ankle 290; determining tibia and talar cut locations as a function of the chosen prosthesis size 360, the bone cutting data 364 correlative to the chosen prosthesis size, and the virtual 3-dimensional model 140 of the ankle 290 which includes utilizing the topography of the anterior border or surface 306 of the distal tibia 304 from the virtual 3-dimensional model 140 as a reference surface for the tibial cuts and utilizing the criteria that a plane of the superior tibial cut 310 (FIGS. 4 and 24) is substantially perpendicular to the central axis 302 of the tibia 300 and of a depth that is similar to the depth of the talar cut 340 (FIG. 5), that the medial malleolus cut 314 in the medial malleolus is no deeper than about one-third (⅓) of the interior depth of that bone, that an axis of the cut 314 (FIGS. 4 and 24) in the medial malleolus and the axis of the lateral cut 312 (FIGS. 4 and 24) of the tibia 300 each follow the "mortise"; that is, they are perpendicular to the internalleolar axis thereby forming a trapezoidally shaped opening, and that the center of the axis of the cut 314 in the medial malleolus and the axis of the lateral cut 312 pass through the central axis of the tibia; determining a distance 322 (FIG. 5) defined as the distance from the central axis 302 of the tibia 300 to the anterior border or surface 306 of the distal portion 304 of the tibia 300 at the level of the superior tibial cut 310 and a distance 324 (FIG. 4) defined as the distance from the central axis 302 of the tibia 300 to the medial edge of the tibial cut at its superior surface wherein distance 322 and 324 define the position of the central axis 302 of the tibia 300 relative to the custom tibial cutting guide 20 on the anterior surface portion 306 of the distal portion 304 of the tibia 300; determining the depth of the reaming guide locator notch 46 formed in the posterior surface 40 of the custom tibial cutting guide 20 by utilizing the formula $D=D1-D2$ wherein D=the depth of the notch, D1 equals the distance from the central axis of the tibia to the anterior surface of the tibia (distance 322) at the superior tibial cut 310, and D2 equals the distance, parallel to the distance D1, from an anterior or front face 174 of a reamer body 162 of the tibial reaming guide 160 to the center of a channel 178 in the reamer body 162 (FIG. 10) and wherein the width of the locator notch 46 is determined by a predefined size 158 of the tibial reaming guide 160 corresponding to the chosen prosthesis 360 and determined by the computer modeling system 130; determining a location and depth of a blind bore 328 (FIG. 29) of the tibia 300 reamed along the central axis 302 of the tibia 300, the plane and parameters of the talar or dome cut 340 (FIGS. 4 and 24) of the talus 330, and a location, depth, and angularity of a reamed blind bore 344 (FIG. 23) of the talus 330 as a function of the chosen prosthesis size 360 and the virtual 3-dimensional ankle model 140 and by utilizing the criteria that the plane of the cut in the dorsum of the talus is parallel to the plane of the bottom of the foot, that the depth of this cut will be similar to the depth of the cut in the distal tibia 304, that a position of the dome of the talus and the central axis 302 of the tibia 300 are used to determine the placement of talar dome component 388 of a talar prosthesis component (FIG. 30) and the position of reaming for a stem 390 of the talar prosthesis component is referenced off the topography of the neck 336 of the talus 330 (FIG. 5), and wherein the width of the talus at the level of the cut equals distance 354 plus distance 356 and the position of the dome of the talus is determined by distances 326, 354, and 356 (FIGS. 4 and 5) which are utilized to determine the placement of the fixation holes 114, 116 in the custom talar cutting guide 80 (FIG. 6) wherein distance 326 is defined as the distance from the central axis 302 of the tibia 300 to the dorsum of the talar neck at the level of the of the cut 340 (FIG. 5) when the tibia and talus are properly aligned.

Accordingly, the analyses of the virtual 3-dimensional model 140 of the ankle 290 as a function of known and computed criteria results in the tibial guide machine control data 142 comprising information or data correlative to the anterior topography of the anterior surface 306 of the distal tibia 304 of the patient, the location and size of the tibia fixation holes 60, the location and size of the tibia saw cutting slits 54, 56, and 58, the location and size of tibial blind bore 328, the location and size of the tibial reaming guide locator notch 46, the location and size of the tibial reaming guide fixation holes 62, and the location and size of the outrigger alignment guide locator notch 64.

Additionally, the analyses of the virtual 3-dimensional ankle model 140 as a function of known and computed criteria results in the talar guide machine control data 144 comprising information or data correlative to information on the topography of the dome 332 of the talus 330 or the topography of dome surface 334 and the topography of the dorsum of the talar neck 336 or the topography of dorsum surface 338; the location and size of the fixation holes 114, 116; the location and size of the talus cutting slit 112; and the size, location, and angularity of the angled reaming channel or bore 100.

After obtaining tibial guide machine control data 142 and talar guide machine control data 144, the system 120 performs a step of communicating the tibial guide machine control data 142 and the talar guide machine control data 144 to the computer or numerically controlled machine system 150 via the interconnected network 128 and/or the removable memory storage medium 126.

Figure 30:
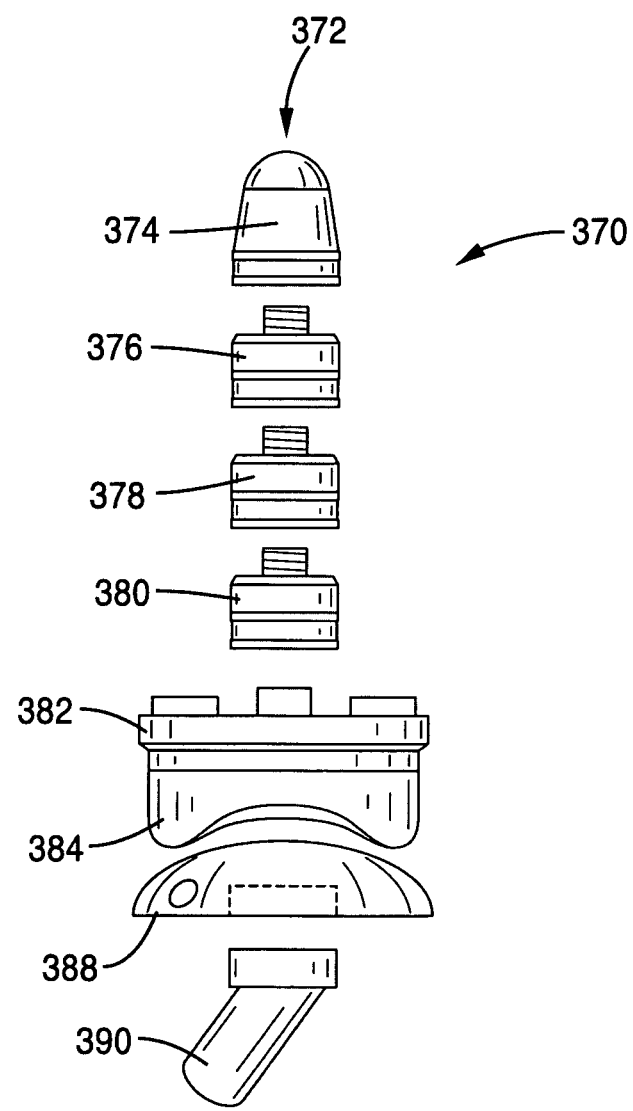
FIG. 30 is an exploded parts view of one size of one embodiment of the ankle prosthesis.

And, a further step of utilizing the computer or numerically controlled machine system 150 as a function of the tibial guide machine control data 142 and the talar guide machine control data 144 for respectively molding and milling the custom tibial cutting guide 20 and the custom talar cutting guide 80. As a result of the above utilizing step, the molded and milled custom tibial cutting guide 20 is comprised of the first posterior surface portion 42 which is the inversion of the anterior topography or surface 306 of the distal tibia 304, the reaming guide locator notch 46, the saw cutting slits 54, 56, 58, the tibia fixation holes 60, the reaming guide fixation holes 62, and the outrigger alignment guide locator notch 64 all precisely shaped, sized, and located as a function of the radiographic information or data 124 of the ankle 290 of the patient and the chosen size 360 of the prosthesis 370 (FIG. 30). Additionally, and a result of the above utilizing step, the molded and milled custom talar cutting guide 80 is comprised of the dome member 82 having the inferior surface 96 which is the inversion of the topography of the dome 332 of the talus 330 or of the topography of the dome surface 334; the angled reaming channel 100; the neck member 102 having the posterior surface 108 which is the inversion of the topography of the dorsum of the talar neck 336 or the topography of the dorsum surface 338; the talus cutting slit 112; and the talar fixation holes 114, 116 all precisely shaped, sized, and located as a function of the radiographic information or data 124 of the ankle 290 of the patient and the chosen size 360 of the prosthesis 370 (FIG. 30).

Tibial Reaming guide 160 and Cannulated Reaming Bit 190

Figure 10:
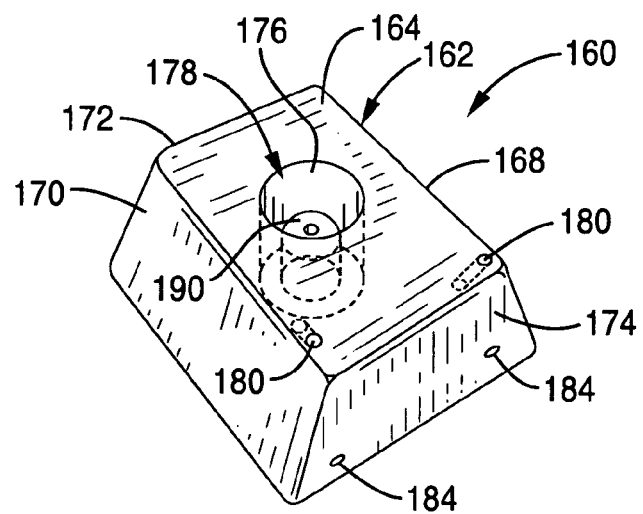
FIG. 10 is a top, front, and side perspective view of the tibial reaming guide having a central body channel circumscribing the removable, cannulated reaming bit, and further illustrating fixation holes for removably attaching the tibial reaming guide to the custom tibial cutting guide and the C-shaped outrigger alignment guide.
Figure 11:
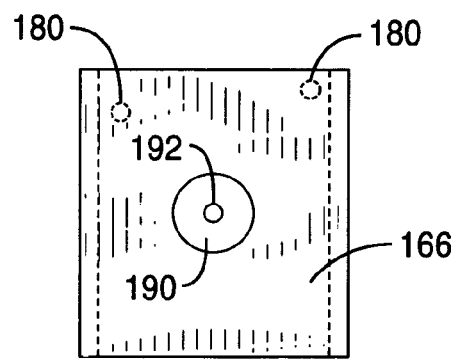
FIG. 11 is a bottom elevational view of the tibial reaming guide illustrated in FIG. 10.
Figure 12:
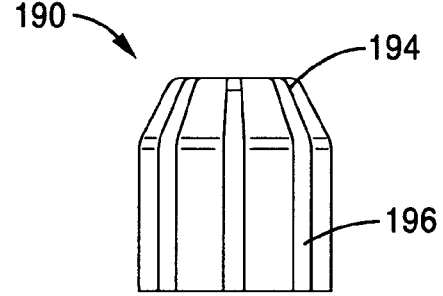
FIG. 12 is a side elevational view of the cannulated reaming bit.

Referring to FIGS. 10 through 12, and in one embodiment, the system 10 is further comprised of the tibial reaming guide 160 and the cannulated reaming bit 190 having a central opening or axial passage 192 for use in preparing the tibia 300 for an intramedullary stem that is in the form of a modular tibial stem component 372 of the chosen prosthesis 370 (FIG. 30). The tibial reaming guide 160 is designed come in a range of sizes that correspond to the different selection of prosthesis sizes 362.

In one embodiment, the tibial reaming guide 160 is comprised of a generally pyramidal frustum shaped reamer body 162 that is designed to fit into the tibial-talar space 342 defined as the space between the tibia 300 and the talus 330 after the resected tibial and talar bone segments have been removed. Accordingly, and as noted above, the reamer body 162 corresponds to the size of the chosen prosthesis 370 to be used, so if there are five different prosthesis sizes to choose from then there are five different tibial reaming guide sizes for providing a one to one correspondence between the two.

Referring to FIGS. 10 and 11, the generally pyramidal frustum shaped reamer body 162 is comprised of six faces: a superior face 164, an inferior face 166, an inner face 168, an outer face 170, a posterior face 172, and an anterior face 174. The superior and inferior faces 164 and 166 have a generally square or rectangular shape while the inner face 168, outer face 170, posterior face 172, and anterior face 174 have a generally trapezoidal shape. Additionally, the reamer body 162 of the tibial reaming guide 160 is comprised an open ended, interior cylindrical surface 176 that defines an open ended cylindrically shaped central channel 178 that runs from the superior face 164 to inferior face 166 of the reamer body 162 and that is substantially perpendicular to those faces. The open ended cylindrically shaped central channel 178 receives the cannulated reaming bit 190 comprised of the axial passage 192 extending through the interior of the cannulated reaming bit 190 and a bone reaming exterior surface comprised of front cutting threads 194 and side cutting threads 196.

Furthermore, the generally pyramidal frustum shaped reamer body 162 has a central axis that passes through the center of the central channel 178 and that aligns or is coincident with the central axis 302 of the tibia 300 when the trapezoidally shaped anterior face 174 of the reamer body 162 abuts against the trapezoidally shaped posterior surface portion 44 of the reaming guide locator notch 46 and when the custom tibial cutting guide 20 is placed against the anterior surface portion 306 of the distal portion 304 of the tibia 300 with a portion of the reamer body 162 received within the tibial-talar space 342. Thus, when the cannulated reaming bit 190 is received within central channel 178, the shape of the custom tibial cutting guide 20 and the depth of the locator notch 46 in its distal end combine to set the alignment of the axial passage 192 of the cannulated reaming bit 190 with the central axis 302 of the tibia 300 for reaming of the tibia 300 along its central axis 302 with the reaming exterior front and side cutting threads 194, 196 of the cannulated reaming bit 190 as will be further delineated below. The diameter of the central channel 178 of the reamer body 162 is sized to closely receive and temporarily hold the cannulated reamer bit 190 which, in turn, is of the size needed to ream the tibial blind bore 328 for the size of the tibial stem or, in one embodiment, the modular tibial stem components 372 of the size of the preoperatively chosen prosthesis 370.

Figure 26:
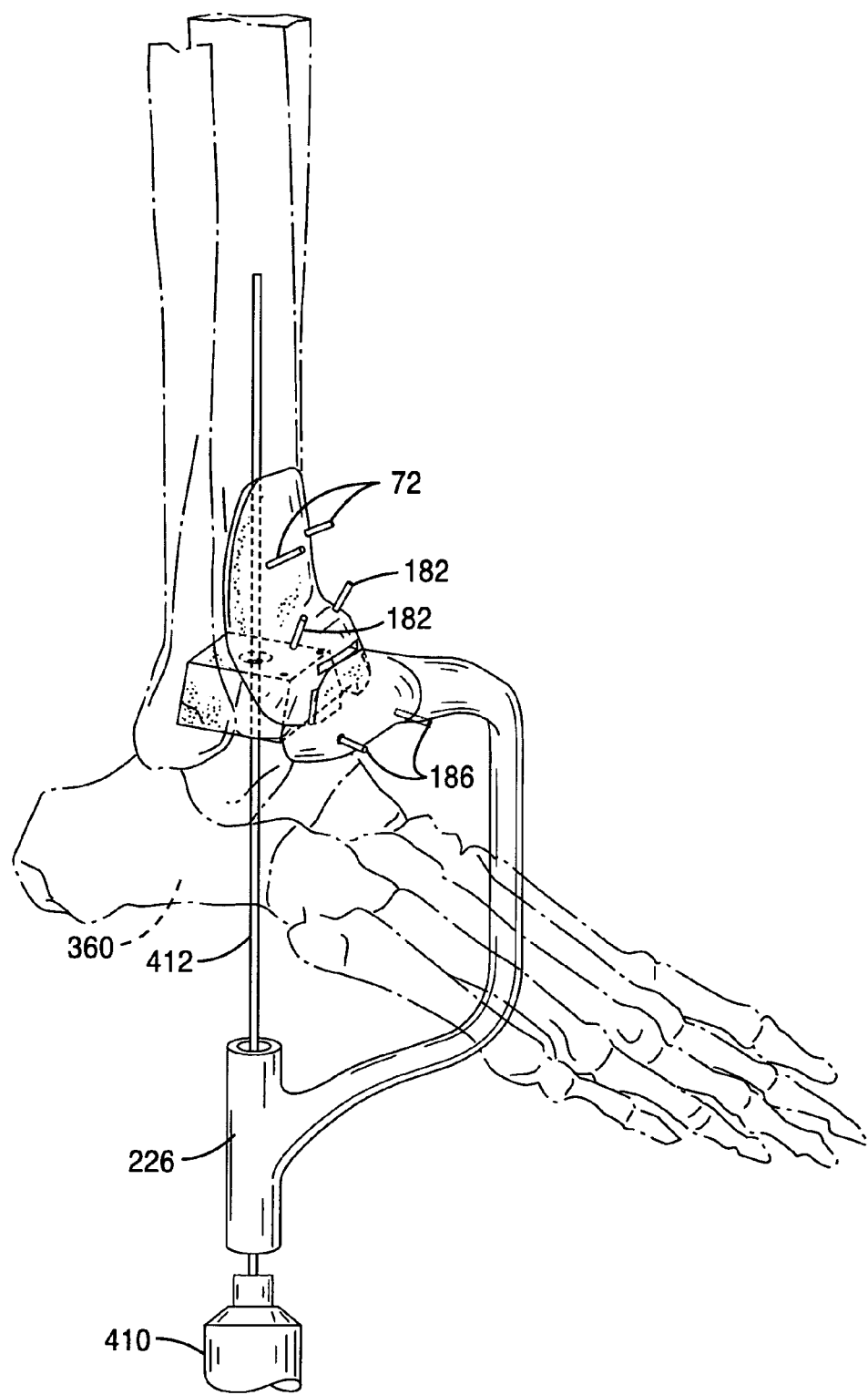
FIG. 26 is a front and side perspective view of the custom tibial cutting guide, the tibial reaming guide circumscribing the cannulated reaming bit, the C-shaped outrigger alignment guide, the K-wire, and the conventional surgical drill all relatively coupled together and to the prepared bone structure, and further illustrating the k-wire after being drilled up through the bottom of the calcaneus and the talus, through a central hole in the cannulated reaming bit, and then into the distal tibia for a predetermined distance along the central axis of the distal tibia.

Moreover, holes 180 in the body 162 of the tibial reaming guide 160 align with the reamer body fixation holes 62 (FIG. 2) disposed in the custom tibial cutting guide 20. Thin wires 182 are placed through the aligned holes to temporarily fix the custom tibial cutting guide 20 to the reamer body 162 (FIG. 26). Additionally, holes 184 disposed through the anterior face 174 of the reamer body 162 align with the fixation holes 211 disposed in the C-shaped outrigger alignment guide 200 for receiving thin wires 186 through the aligned holes to temporarily fix the C-shaped outrigger alignment guide 200 to the reamer body 162 anteriorly as illustrated in FIG. 26. Fixing the custom tibial cutting guide 20 to the anterior surface 306 of the distal portion 304 of the tibia 300 and to the reamer body 162 of the reaming guide 160, and then coupling the C-shaped outrigger alignment guide 200 to the custom tibial cutting guide 20 via the locator notch 64 and key 216 coupling and to the reamer body 162 via thin wires 186 provides stability for accurate reaming of the tibia 300 along its central axis as will be further delineated below.

In one embodiment, the tibial reaming guide 160 and the cannulated reaming bit 190 are made out of, but not limited to a metal material.

Outrigger Alignment Guide 200

Figure 13:
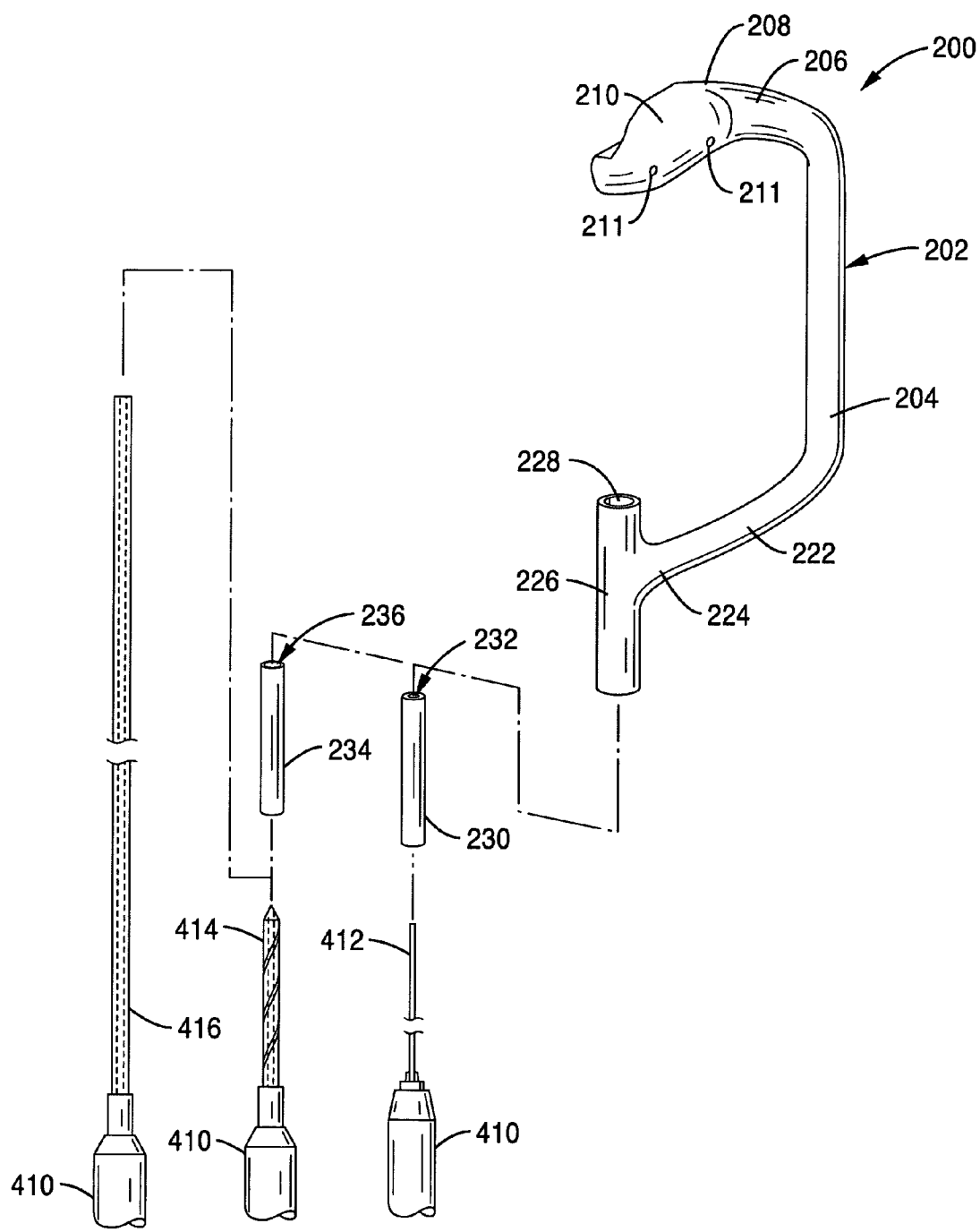
FIG. 13 is a front and side perspective view of the C-shaped outrigger alignment guide, the cylindrically shaped inner sleeve wire guide, the cylindrically shaped inner sleeve drill and driver bit guide, and further illustrating a thin wire or K-wire, a cannulated drill bit, and a cannulated reamer driver bit each coupled to a surgical drill.

Referring to FIG. 13, and in one embodiment, the system 10 is further comprised of the outrigger alignment guide 200. The outrigger alignment guide 200 is comprised of an arcuate or generally C-shaped body 202 comprised of a medial section 204 transitioning at one end to a superior section 206 and at the other end to an inferior section 222.

Figure 14:
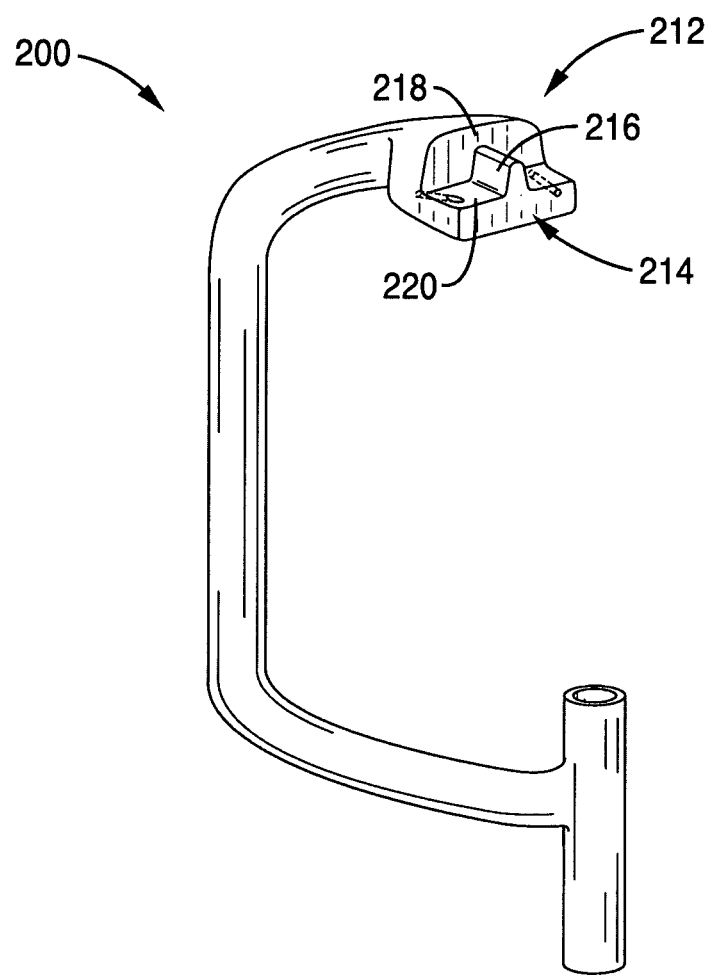
FIG. 14 is a back perspective view of the C-shaped outrigger alignment guide.

Referring to FIGS. 13 and 14, and in one embodiment, the superior section 206 generally perpendicularly extends away from the medial section 204 in substantially the same plane as the medial section 204, and then arches or bends out of the plane of the medial section 204 and transitions to a superior end 208 supporting an L-shaped bracket 210. In one embodiment, the L-shaped bracket 210 is integrally formed with the superior end 208 and is comprised of a superiorly extending sidewall 212 and a posteriorly extending base wall 214 that generally perpendicular extends from a distal end of the sidewall 212. The L-shaped bracket 210 is further comprised of a rectangular parallelepiped shaped ridge or key 216 that posteriorly extends from a posterior surface 218 of the sidewall 212 and superiorly extends from a superior surface 220 of the base wall 214. The rectangular parallelepiped shaped ridge or key 216 is sized to be received in the outrigger alignment guide locator notch 64 of the custom tibial cutting guide 20 for aligning the outrigger alignment guide 200 relative to the central long axis 302 of the tibia 300 when the custom tibial cutting guide 20 is coupled thereto. Additionally, the posterior surface 218 of the sidewall 212 is shaped to generally abut against a portion of the anterior surface 34 of the custom tibial cutting guide 20 that is generally below the superior tibial cutting slit 54 and generally between the lateral and medial cutting slits 56, 58 while the superior surface 220 of the base wall 214 is shaped to generally abut against the generally flat distal edge 26 of the generally half-bell-shaped body 22 of the custom tibial cutting guide 20.

The inferior section 222 generally perpendicularly extends away from the medial section 204 in substantially the same plane as the medial section 204, and then arches or bends out of the plane of the medial section 204 and transitions to an inferior end 224 supporting an inferior cylindrically shaped sleeve attachment 226 having an open ended cylindrically shaped bore 228 axially extending therethrough.

As illustrated in FIG. 13, the cylindrically shaped sleeve attachment 226 is integrally formed with and extends from both sides of the inferior end 224, and is spaced from and generally parallel with the medial section 204.

The open ended cylindrically shaped bore 228 of the sleeve attachment 226 is sized to closely receive two removable, alternate inner sleeve guides: the cylindrically shaped inner sleeve wire guide 230 having a open ended cylindrically shaped interior bore 232 extending therethrough and the cylindrically shaped inner sleeve drill and driver bit guide 234 having an open ended cylindrically shaped interior bore 236 extending therethrough.

The open ended cylindrically shaped interior bore 232 of the wire guide 230 is sized to closely receive and pass a thin wire such as a K-wire 412 therethrough and the open ended cylindrically shaped interior bore 236 of the drill and driver bit guide 234 is sized to closely receive and pass either a cannulated drill bit 414 or a cannulated driver bit 416 therethrough. The open ended cylindrically shaped interior bore 236 of the drill and driver bit guide 234 is of a larger diameter than the diameter of the open ended cylindrically shaped interior bore 232 of the wire guide 230.

In one embodiment, the outrigger alignment guide 200 is made out of, but not limited to a metal material and is constructed as, but not limited to, an integrally formed one piece instrument. Additionally, and in one embodiment, the wire guide 230 and the drill and driver bit guide 234 are made out of, but not limited to a metal material.

Skeleton Cage 240 and Double Fork Cage 260

In one embodiment, the system 10 is further comprised of two metal instruments that are used as internal frames for providing temporary stability and alignment between the tibia 300 and talus 330 during the construction of the tibial stem 372 of the chosen prosthesis 370. Both instruments can be easily removed and re-inserted as needed to allow for easier passage of the components into the tibial-talar space 342.

Figure 15:
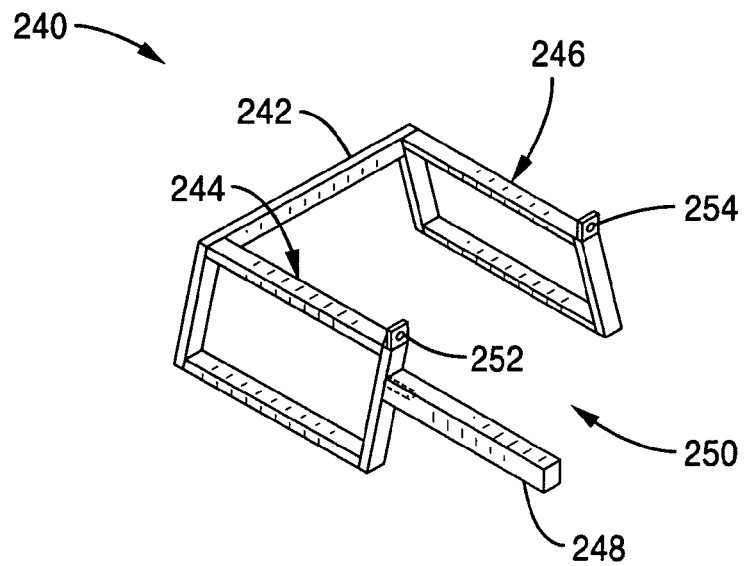
FIG. 15 is a perspective view of a skeleton cage or first frame that fits into a space between the prepared tibia and talus defining as a tibial-talar space for holding the bones apart with some stability while tibial stem components of a chosen prosthesis fit in place, and further illustrating a handle that aids in its insertion and removal and holes on its superior edges for use in temporary fixation to the tibia with wires or screws.

Referring to FIG. 15, a first internal frame is a skeleton cage 240 comprised of a posterior transverse member 242 rigidly connected between two superior portions of two spaced apart, rectangularly shaped, and inwardly slanting frames 244, 246 for providing the skeleton cage 240 with an external shape that is generally congruent with the generally pyramidal frustum shape of the tibial reaming guide 160 so as to fit snugly in the space between the tibia 300 and talus 330 defined as the tibial-talar space 342.

In one embodiment, the skeleton cage 240 has an external handle 248 operatively connected to and extending from an anterior edge of at least one of frame members 244, 246 to aid in manipulating the skeleton cage 240 into and out of position. FIG. 15 illustrates the operative coupling of the external handle 248 to the outer frame member 244.

Figure 16:
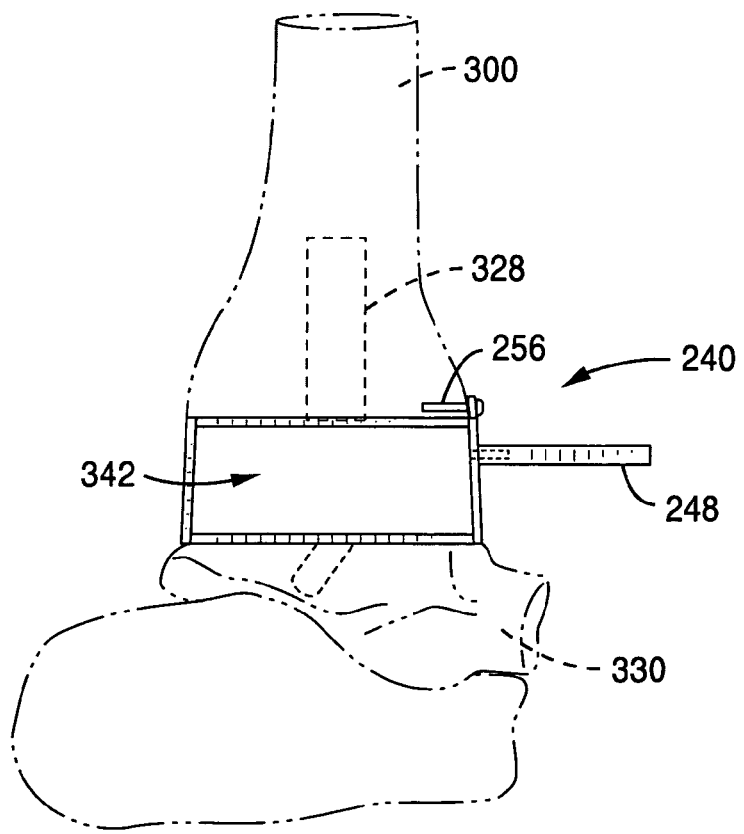
FIG. 16 is a side elevational view of the skeleton cage positioned into the tibial-talar space and removably attached to the tibia.

Referring to FIGS. 15 and 16, a central anterior open portion 250 of the skeleton cage or first frame 240 allows stem pieces of the modular tibial stem component 273 to be easily passed through skeleton cage 240 and into the tibial-talar space 342 for insertion into the blind bore 328 reamed in tibia 300. Additionally, the skeleton cage 240 is comprised of two perforated tabs 252, 254 that can be used to connect the skeleton cage 240 to the tibia via wires or screws 256.

Figure 17:
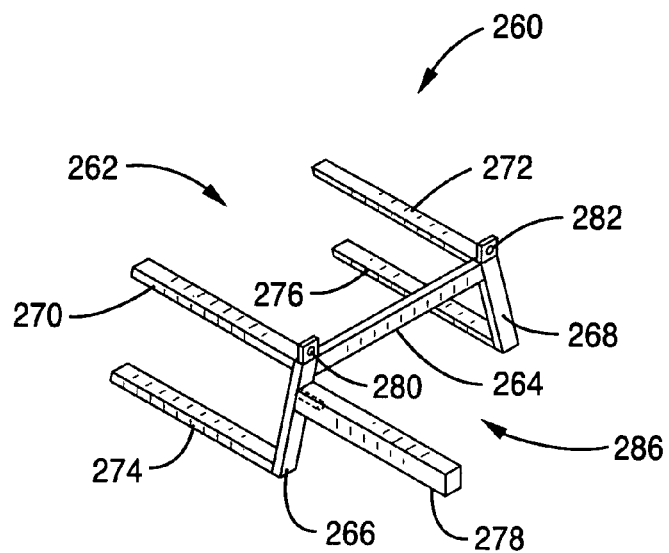
FIG. 17 is a perspective view of a double fork cage or second frame that fits into the tibial-talar space for holding the tibia and talus bones apart during the placement of a tibial tray, and further illustrating a handle that aids in its insertion and removal and holes on its superior edges for use in temporary fixation to the tibia with wires or screws.
Figure 18:
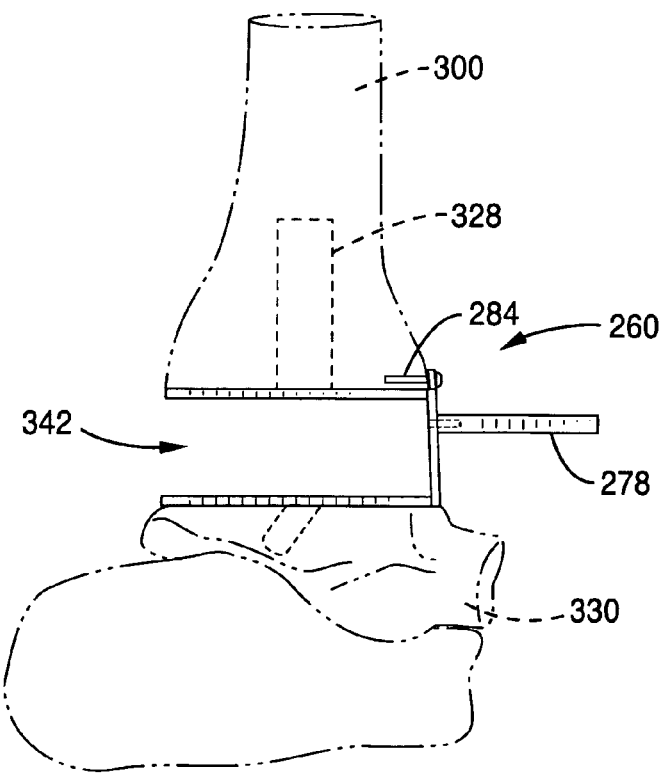
FIG. 18 is a side elevational view of the double fork cage positioned into the tibial-talar space and removably attached to the tibia.

Referring to FIGS. 17 and 18, a second internal frame is a double fork cage 260 comprised of an anterior frame 262 having three members outlining three sides of a trapezoid. Specifically, the anterior frame 262 is comprised of a superior base member 264 rigidly connected between superior ends of two spaced apart, non-parallel frame members 266, 268. The anterior frame 262 is substantially the size of the tibial-talar space 342. Additionally, the double fork frame 260 is comprised of four spaced apart, generally parallel tines 270, 272, 274, and 276 that are operatively coupled to and extend posteriorly off the anterior frame 262 into the superior medial, the superior lateral, the inferior medial and the inferior lateral edges of the tibial-talar space 342. The anterior frame 262 is further comprised of an external handle 278 that extends off an anterior face of one of three members 262, 264, or 266 to aid in manipulating the double fork frame 260 into and out of position. FIG. 17 illustrates the operative coupling of the external handle 278 to the frame member 266. Additionally, and in one embodiment, the double fork frame 260 is comprised of two perforated tabs 280, 282 that can be used to connect the frame 260 to the tibia via wires or screws 284.

In one embodiment, the double fork cage 260 is placed in the tibial-talar space 342 prior to coupling of the inferior tibial tray component 382 to the inferior stem piece 380 of the chosen prosthesis 370.

Next, the inferior tibial tray component 382 is passed through a central anterior open portion 286 of the double fork cage 260 and coupled to the inferior stem piece 380.

Then, the double fork cage 260 is removed prior to the tray 382 being seated into its final position.

Use and Operation

Preoperative Process

In use and operation, and referring to the drawings, the morphology of an ankle being replaced is preoperatively assessed radiographically using the computer imaging system 122 for obtaining radiographic information or data 124. This radiographic information or data is transformed into a virtual 3-dimensional copy or model 140 of the ankle with the existing 3-D modeling software 138 of the computer modeling system 130. The 3-D modeling software 138 then analyzes the virtual ankle model 140 and chooses one prostheses size 360 from a plurality of available sizes of existing prosthesis 362 and determines where the bones should be cut and reamed as a function of transformed radiographical preoperative analysis of the ankle and the chosen size of the prosthesis. Accordingly, the process of choosing one of a plurality of available sizes of existing prosthesis and determining the associated bone cuts correlative to the chosen size of the prosthesis is done preoperatively by utilizing the radiographic information or data 124 obtained by the computer imaging system 122 and the analysis provided by the computer modeling system 130.

Next, the computer or numerically controlled machine system 150 molds the custom tibial cutting guide 20 out of, for example, plastic and mills the guide 20 to fit precisely against the anterior surface portion 306 of the distal portion 304 of the tibia 300 as a function of the computer analysis. Additionally, and also as a function of the computer analysis, the computer or numerically controlled machine system 150 molds the custom talar cutting guide 80 out of, for example, plastic and mills the guide 80 to fit precisely on the talar dome 332 and against the dorsum of the talar neck 336. Furthermore, and as delineated in detail hereinabove, the custom cutting guides 20, 80 are milled with precisely oriented slits that guide the position of saw blades, and holes for drill bits, reamer bits, and fixation pins or screws so that when each guide 20, 80 is coupled to its respective bone in its unique position, the slits and holes are in the preoperatively defined position for each of them.

Tibia Cuts

In one embodiment, and referring to FIGS. 2 through 4, 19 and 20, the custom tibial cutting guide 20 is utilized first and, like a lock, the first posterior surface portion 42 of the custom tibial cutting guide 20 matches the anterior surface portion 306 of the distal portion 304 of the tibia 300 in one unique position. In this unique position, the cutting slits 54, 56, and 58 along with the bone fixation holes 60, the reaming guide locator notch 46, and the alignment guide locator notch 64 are in their preoperatively defined positions. In one embodiment, the custom tibial cutting guide 20 covers the distal 4-6 cm of the tibia 300 and spans the anterior ankle from the medial malleolus to the interior side of the lateral malleolus. Once the custom tibial cutting guide 20 is fitted to the distal portion 304 of the tibia 300, screws or wires 72 are passed through the plurality of fixation holes 62 in the guide 20 so that it can be temporarily fixed to the tibia bone 300. Then, the tibia saw blade 402 (FIG. 20) is placed through the precisely placed slits 54, 56, and 58 of the guide 20 and powered by the saw 400 for making the preoperatively defined cuts in the tibia 300. After the tibia bone cuts have been made, the screws or wires 72 are taken out, and the custom tibial cutting guide 20 is removed and saved for later use with the tibial reaming guide 160. The pieces of cut tibia bone are then removed.

Talus Cuts

Referring to FIGS. 5 through 7, and 21 through 23, the custom talar cutting guide 80 is utilized next and, like a lock, the inferior surface 96 of the cutting guide 80 matches, in one unique position, the surface 334 of the talar dome 332 and the posterior surface 108 of the cutting guide 80 matches, in one unique position, about three to four centimeters of the dorsum 338 of the talar neck 336. In this unique position, the angled reaming channel 100, the cutting slit 112 and the bone fixation holes 114, 116 are in their preoperatively defined positions. Once the custom talar cutting guide 80 is fitted to the talus 330, screws or wires 350 are passed through the plurality of fixation holes 116 in the guide 80 so that it can be temporarily fixed to the talus bone 330. Then, the talus saw blade 406 is placed through the precisely placed slit 112 of the guide 80 and powered by the saw 400 for making the preoperatively defined cut of the top of the talus bone 330.

After the top of the talus 330 is cut, screws or wires 346 can be passed through the plurality of fixation holes 114 in the guide 80 so that the cut top of the talus 330 is held in place.

Next, the drill or reamer bit 422 is placed through the angled reaming channel 100 and powered by drill 420 for reaming the talus 330 to a preoperatively determined depth achieved by utilizing, for example, a stop collar 424 disposed on the reaming bit 422 or a precisely sized reaming bit 422.

Then, the wires or screws 346, 350 are taken out, and the custom talar cutting guide 80 is removed, and the cut piece of talus bone taken away thereby forming the trapezoidally shaped tibial-talar space 342 (FIG. 24) between the tibia 300 and the talus 330.

Angular Deformity Correction

It is important to note that the two separate custom guides 20, 80 provide the means for correcting any angular deformity of the ankle and for preparing the bones of the ankle to receive a chosen prosthesis 370 in the proper orientation that precludes the prosthesis 370 from being angled one way or another and, as a result, precludes the patient from walking on one side or the other of the foot thereby abating stress in different areas of the prosthesis 370 that results in the components of the prostheses 370 failing or wearing out prematurely. The goal is for the prosthesis to last for decades. Accordingly, the two separate custom cutting guides 20, 80 can correct for any angular deformity of the ankle by making cuts in the tibia 300 and a cut in the talus 330 that are related to each respective bone itself and not one another. So when the cuts are made with the custom cutting guides 20, 80, the surfaces are substantially flat. Specifically, the custom cutting guides 20, 80 respectively dictate that the superior cut 310 on the tibia 300 is substantially perpendicular to the long central axis 302 of the tibia 300 and that the cut 340 of the talus is parallel to the bottom of the foot as it rest on the ground and also perpendicular to the long central axis 302 of the tibia 300.

Tibial Reaming Guide 160 & Outrigger Alignment Guide 200

Referring to FIGS. 3, 10, 25, and 26, the tibial reaming guide 160 is used next to prepare the tibia 300 for an intramedullary stem component which, in one embodiment, is the modular tibial stem component 372 of the prosthesis 370. The modular tibial stem component 372 is designed to fit in the center of the tibia 300, and is oriented along its long central axis 302.

As noted above, the size of the tibial reaming guide 160 is preoperatively selected to correspond to the size of the preoperatively chosen prosthesis 370 and has a predetermined size for fitting against the reaming guide locator notch 46 of the custom tibial cutting guide 20, which determines its proper placement for reaming the tibia 300 along its central axis 302. Additionally, the reamer body 162 of the tibial reaming guide 160 is designed to fit into the trapezoidally shaped tibial-talar space 342 after the resected tibial and talar bone segments have been removed.

The cannulated reamer bit 190 having a size that is needed to ream the distal tibia for the size of the chosen tibial stem 372 is removably fitted within the central channel 178 of the reamer body 162 of the tibial reaming guide 160. The reamer body 162 of the tibial reaming guide 160 is placed into the reaming guide locator notch 46 of the custom tibial cutting guide 20 such that the anterior face 174 of the body 162 fits against the second posterior surface portion 44 of the custom tibial cutting guide 20. The holes 180 in the body 162 align with holes 62 in the lower part of the custom tibial cutting guide 20. Thin wires 182 can then be placed through these holes to temporarily fix the custom tibial cutting guide 20 to the reamer body 162 (FIG. 26) of the tibial reaming guide 160.

Next, the tibial reaming guide 160 holding the cannulated reaming bit 190 is positioned into the trapezoidally shaped tibial-talar space 342 and the custom tibial cutting guide 20 is fixed to the distal tibia by wires or screws 72 passing through the bone fixation holes 60 of the guide 20 and into the holes 318 (FIG. 4) in the distal tibia. Positioning the tibial reaming guide 160 into the tibial-talar space 342 and fixing the custom tibial cutting guide 20 to the anterior distal tibia aligns the cannulated reaming bit 190 in the central channel 178 of tibial reaming guide 160 with the central axis 302 of the tibia 300. Thus, the shape of the custom tibial cutting guide 20 and the depth of the locator notch 46 in its distal end, combine to set the alignment of a central axis of central channel 178 coincident with the central axis 302 of the tibia 300.

Now, the bracket 210 of the outrigger alignment guide 200 is coupled to the custom tibial cutting guide 20 by frictionally fitting the generally rectangular parallelepiped shaped ridge or key 216 of the bracket 210 into the outrigger alignment guide locator notch or keyway notch 64 disposed in the distal end of the custom tibial cutting guide 20 and abutting the posterior surface 218 of the bracket 210 against the anterior surface 34 of the custom tibial cutting guide 20. Wire or screws 182 are then passed through bracket holes 211 into the reamer body 162 of the tibial reaming guide 160 via reamer body holes 184.

Once the C-shaped outrigger alignment guide 200 is in place, and by design, the inferior sleeve attachment 226 of the outrigger alignment guide 200 is located just off of the skin of the sole of the foot and the center of the inferior sleeve attachment 226 is aligned with the center of the channel 178 of the tibial reaming guide 160 as illustrated in FIG. 26.

Next, the inner sleeve wire guide 230 is placed through the bore 228 of the inferior sleeve attachment 226 (FIG. 13) and a thin wire 412 such as a k-wire is powered by drill 410 and drilled up through the inner sleeve wire guide 230, through a cut in the skin, then from the base of the calcaneus 360 through the talus 330 and through central opening 192 in the cannulated reamer bit 190 held in the central channel 178 of the tibial reaming guide 160. The wire 412 continues to pass proximally into the tibia 300. The passage of the thin wire 412 through the inner sleeve wire guide 230 supported in the inferior sleeve attachment 226 of the outrigger alignment guide 200 and then through the cannulated reamer bit 190 will guide the thin wire 412 proximally along the central axis 302 of the tibia 300.

Figure 27:
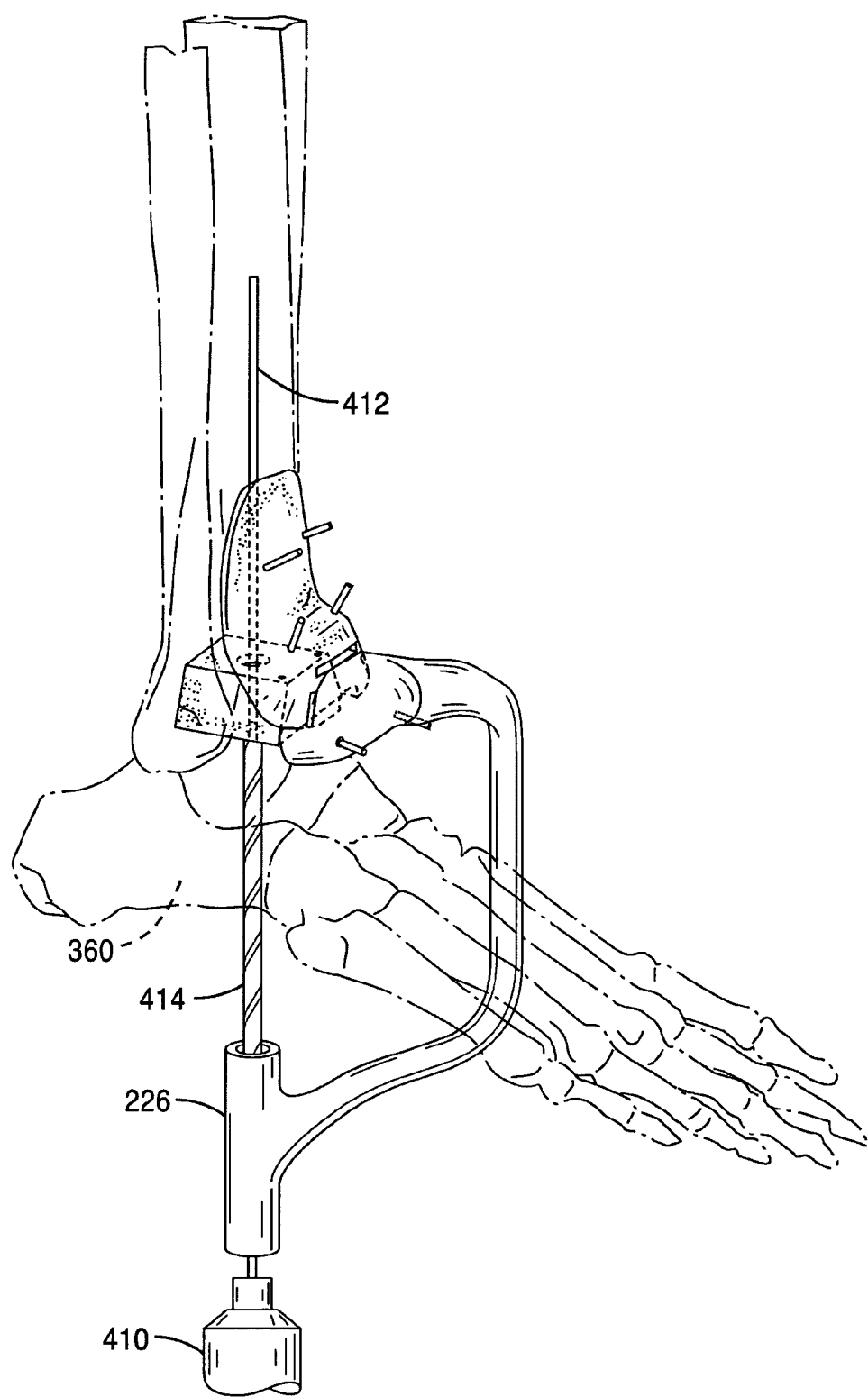
FIG. 27 is a front and side perspective view of the custom tibial culling guide, the tibial reaming guide circumscribing the cannulated reaming bit, the C-shaped outrigger alignment guide, the cannulated drill bit, and the conventional surgical drill all relatively coupled together and to the prepared bone structure, and further illustrating the cannulated drill bit after being drilled over the K-wire passing through the cannulated drill bit, up through the bottom of the calcaneus and the talus, and up to the central hole in the cannulated reaming bit along the central axis of the distal tibia.

Referring to FIG. 27, and with the thin wire 412 left in place, the inner sleeve wire guide 230 is removed, and the inner sleeve drill and driver bit guide 234 having the larger cylindrically shaped bore 236 is placed through the bore 228 of the inferior sleeve attachment 226 (FIG. 13) for guiding and allowing passage of the cannulated drill bit 414 through the inner sleeve drill and driver bit guide 234 for being powered by the drill 410 for drilling over the thin wire 412 through the inferior sleeve attachment 226, the calcaneus 360, and the talus 330 and then, up to the base of the cannulated reamer bit 190 in the central channel 178 of the tibia reaming guide 160.

Then, the cannulated drill bit 414 is removed, again leaving the thin wire 412 in place. The drilling of the calcaneus 360 and talus 330 leaves a wider passage through those bones.

Figure 28:
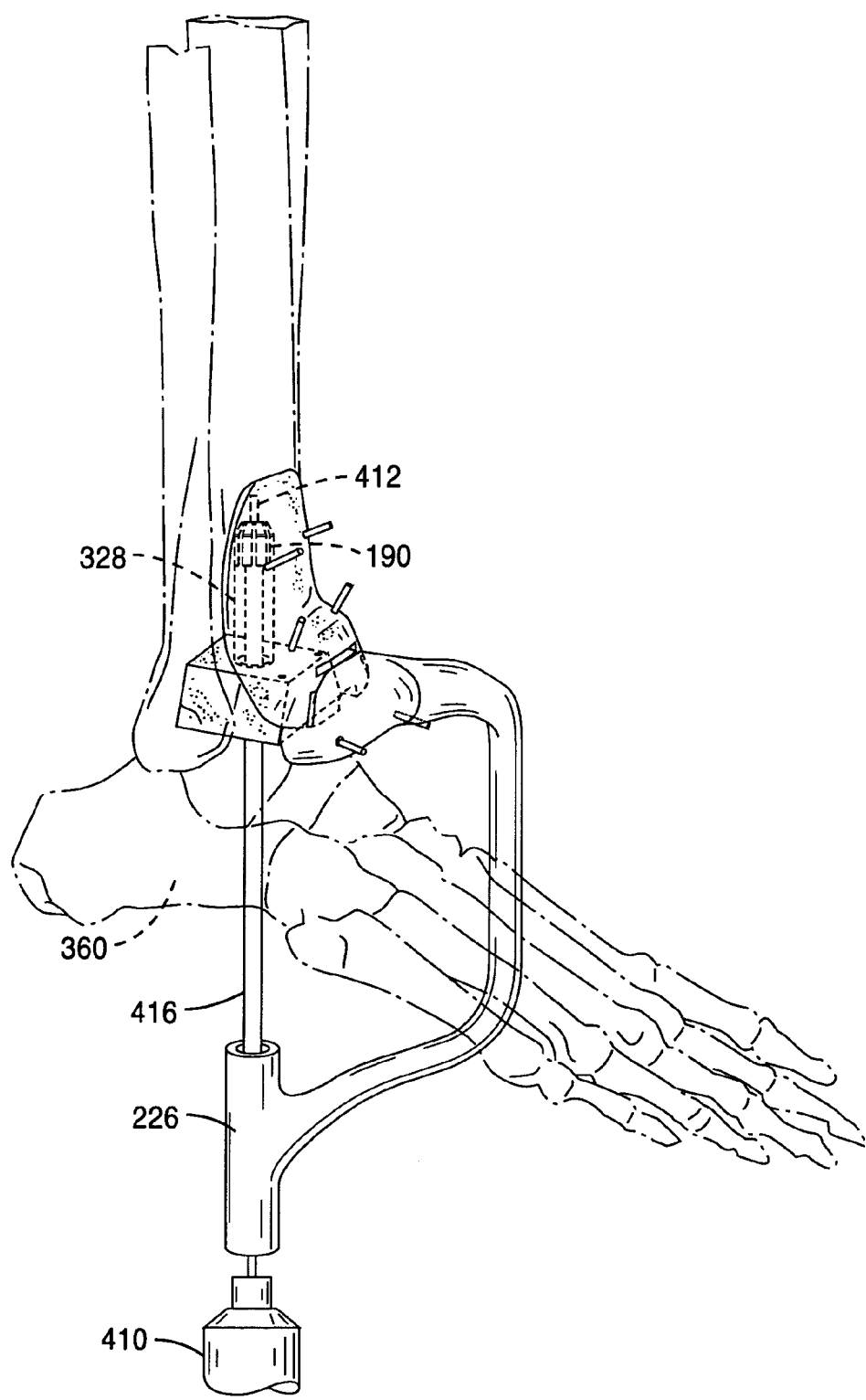
FIG. 28 is a front and side perspective view of the custom tibial cutting guide, the tibial reaming guide circumscribing the cannulated reaming bit, the C-shaped outrigger alignment guide, the cannulated reamer driver bit, and the conventional surgical drill all relatively coupled together and to the prepared bone structure, and further illustrating the cannulated reamer driver bit after being drilled over the K-wire passing through the cannulated drill bit, up through the bottom of the calcaneus and the talus, and after capturing and driving the cannulated reaming bit along the central axis of the distal tibia for forming a blind bore in the tibia for a tibial stem of a ankle prosthesis.

Finally, and referring to FIG. 28, the cannulated reamer shaft or drive 416 with diameter less than the drill bit is passed over the thin wire 412 and up through the inner sleeve drill and driver bit guide 234 in the inferior sleeve attachment 226, the calcaneus 360, and the talus 330 to capture the cannulated reamer bit 190 in the central channel 178 of the tibial reamer guide 160. The distal tibia 304 can then be reamed over the thin wire 412 and along the central axis 302 of the tibia 300 forming the tibia blind bore 328 sized to receive the tibial intramedullary stem 372 of the chosen prosthesis 370.

At the completion of the tibial reaming, the cannulated reamer shaft or drive 416 and thin wire 412 are removed, the temporary fixation wires or screws 72, 182, and 186 are removed, and the custom tibial cutting guide 20, the reaming guide 160, and the C-shaped outrigger alignment guide 200 are removed.

Figure 29:
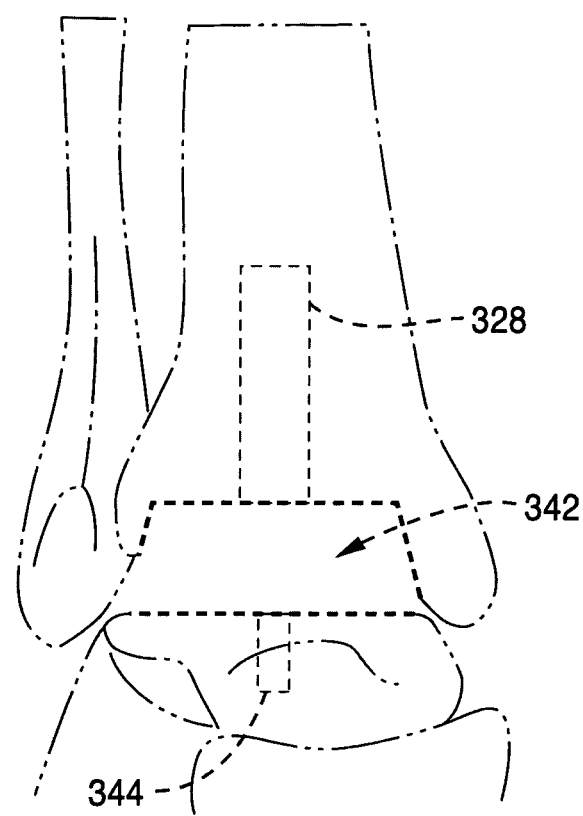
FIG. 29 is a front elevational view illustrating the bone cuts, the tibial blind bore, and the talar blind bore for a chosen size of ankle prosthesis.

At this point, and referring to FIG. 29, the tibia and talus cuts have been made for forming the tibial-talar space 342 and the tibia and talus have been reamed for forming the respective blind bores 328 and 344. Hence, the bones are prepared for placement of the preoperatively chosen total ankle prosthesis such as, but not limited to, the INBONE Total Ankle prosthesis 370 illustrated in FIG. 30. The INBONE Total Ankle prosthesis 370 is sold by Wright Medical Technology, Inc. (5677 Airline Road, Arlington, Tenn. 38002, USA) under the trademark INBONE Total Ankle System and is presently available in five sizes (number 2, 3, 4, 5, or 6), left and right.

In one embodiment, and referring to FIG. 30, the prosthesis 370 is comprised of modular tibial stem component 372, tibial tray component 382, poly insert component 384, talar dome component 388, and talar stem component 390. In one embodiment, the modular tibial stem component 372 is comprised of superior stem piece 374, first medial stem piece 376, second medial stem piece 378, and inferior stem piece 380. The stem pieces range from 14-18 mm in diameter with a typical 4-piece construct measuring 50 mm in length. This is completely customizable per individual patient need. The segmented design allows for a less invasive approach and more robust anchoring. The talar stem component 390 extends at a precise angle inferiorly away from the talar dome component 388 and has 10 mm diameter and is available in 10 and 14 mm lengths.

The general technique or algorithm that is used during surgery for the placement of the prosthesis 370 is as follows.

Figure 31:
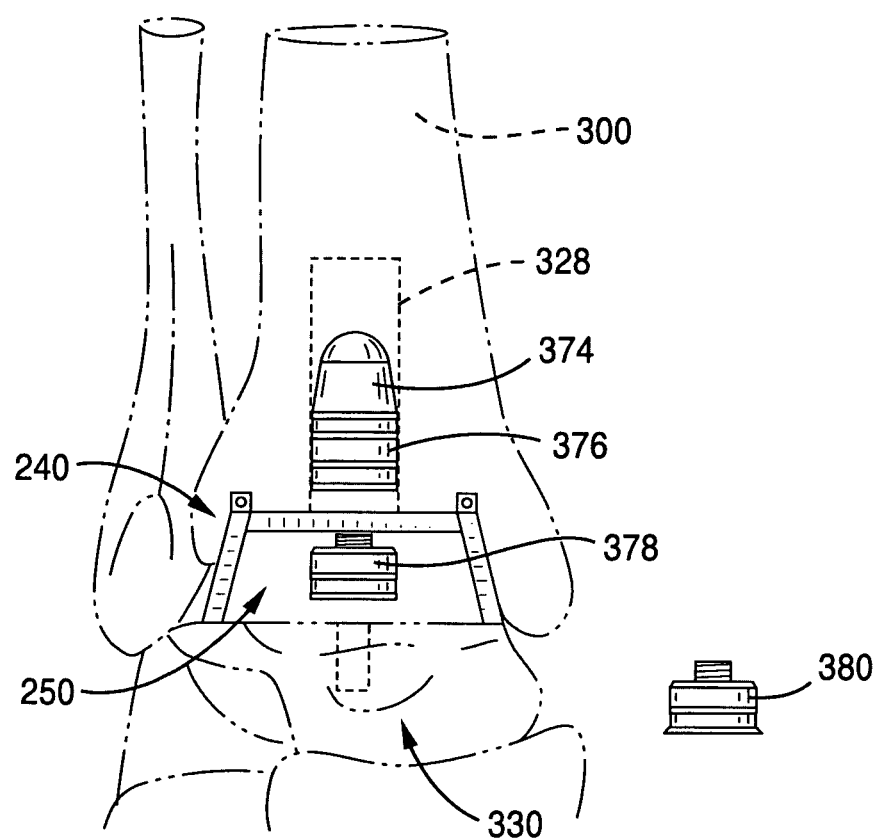
FIG. 31 is a front elevational view of the skeleton cage positioned into the tibial-talar space and removably attached to the tibia, and further illustrating its use during the placement of tibial stem components of the ankle prosthesis illustrated in FIG. 30.

Initially, and referring to FIGS. 30 and 31, the skeleton cage or first frame 240 having an external shape congruent with the tibial reaming guide 160 is fit snugly in the tibial-talar space 342 (FIG. 29) to keep the tibia 300 and talus 330 separated and stabilized. In one embodiment, the skeleton cage 240 employs external handle 248 (FIG. 16) to aid in manipulating it into and out of position and employs two perforated tabs 252, 254 to connect the skeleton cage 240 to the tibia via wires or screws 256. The central anterior open portion 250 of the skeleton cage 240 allows the superior stem piece 374, the first medial stem piece 376, the second medial stem piece 378, and the inferior stem piece 380, to be easily and successively passed therethrough and into the tibial blind bore 328 in the distal portion of the tibia 300 with each stem piece being screwed into the stem piece preceding it. Upon completion, the skeleton cage 240 is removed from the tibial-talar space 342.

Figure 32:
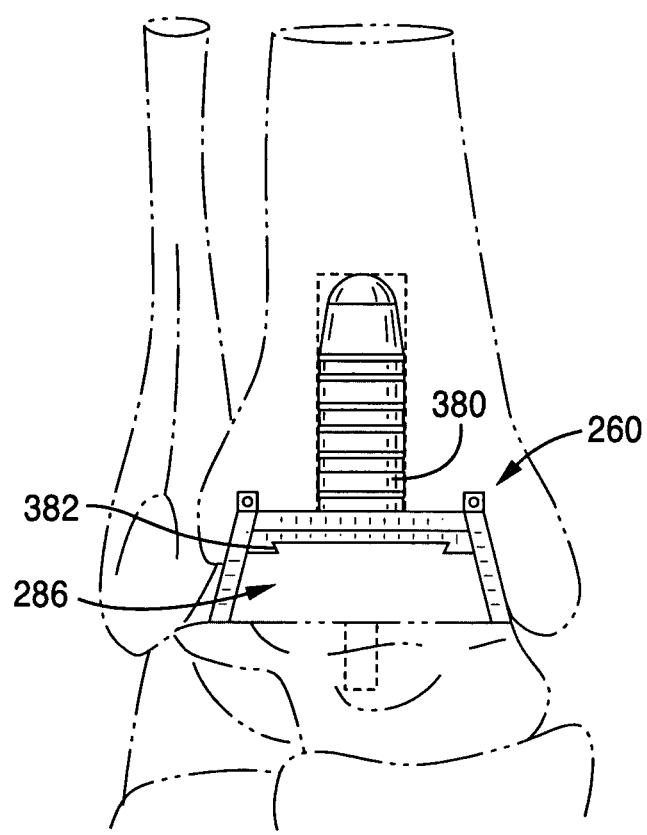
FIG. 32 a front elevational view of the double fork cage positioned into the tibial-talar space and removably attached to the tibia, and further illustrating its use during the placement of a tibial tray of the ankle prosthesis illustrated in FIG. 30.

Next, and referring to FIGS. 30 and 32, the double fork cage or second frame 250 having an external shape congruent with the tibial reaming guide 160 is fit snugly in the tibial-talar space 342 (FIG. 29) to keep the tibia and talus separated and stabilized. In one embodiment, the double fork cage 250 employs external handle 278 (FIG. 18) to aid in manipulating it into and out of position and employs two perforated tabs 280, 282 to connect the double fork cage 250 to the tibia via wires or screws 284. The central anterior open portion 286 of the double fork cage 250 allows the tibial tray component 382 to be easily passed therethrough and partially coupled to the inferior stem piece 380. Then, the double fork cage 250 is removed from the tibial-talar space 342 and the coupling of the tibial tray component 382 to the inferior stem piece 380 is completed.

Figure 33:
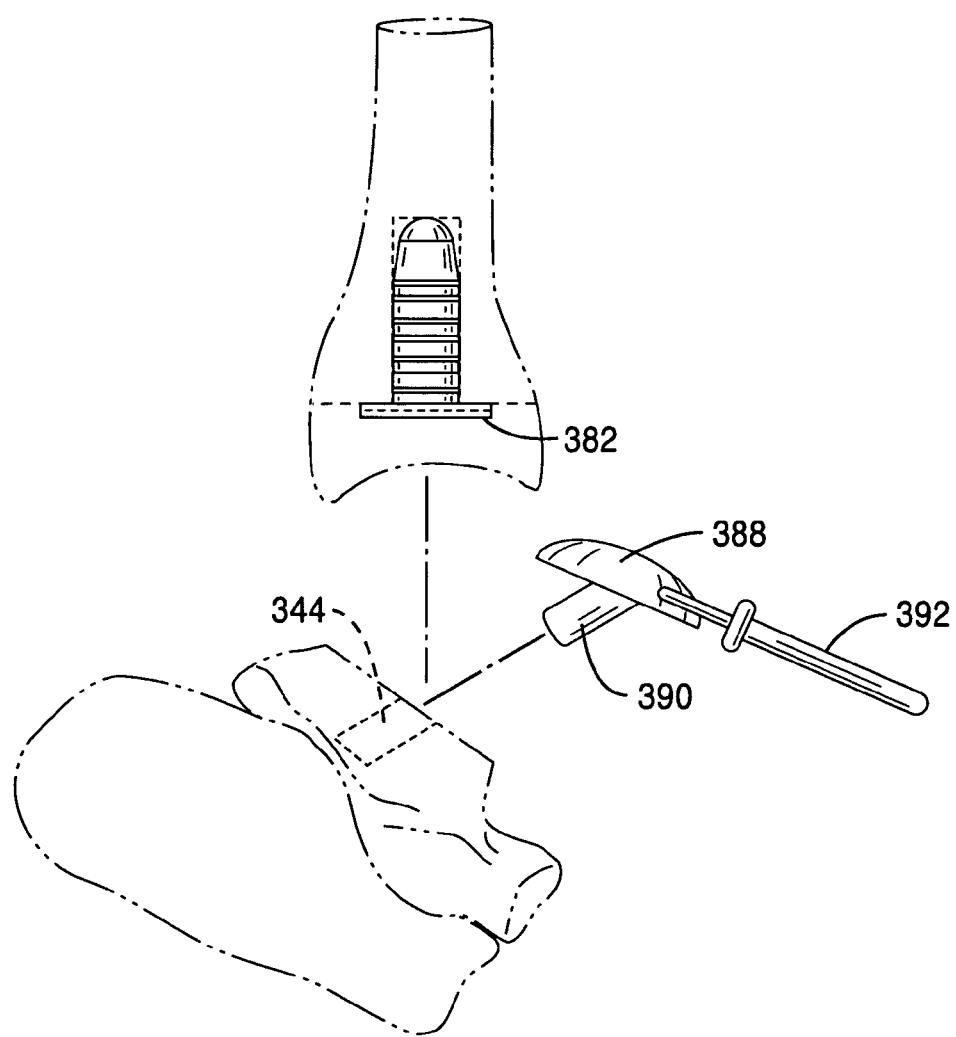
FIG. 33 is a side elevational view illustrating a method step of fitting the talus with the talar dome and stem of the ankle prosthesis illustrated in FIG. 30.

Now referring to FIGS. 30 and 33, the talar stem component 390 is coupled into the pre-drilled talar blind bore 344 followed by using a talar dome holding tool 392 along with a strike tool system to couple the talar dome component 388 to the talar stem component 390.

Figure 34:
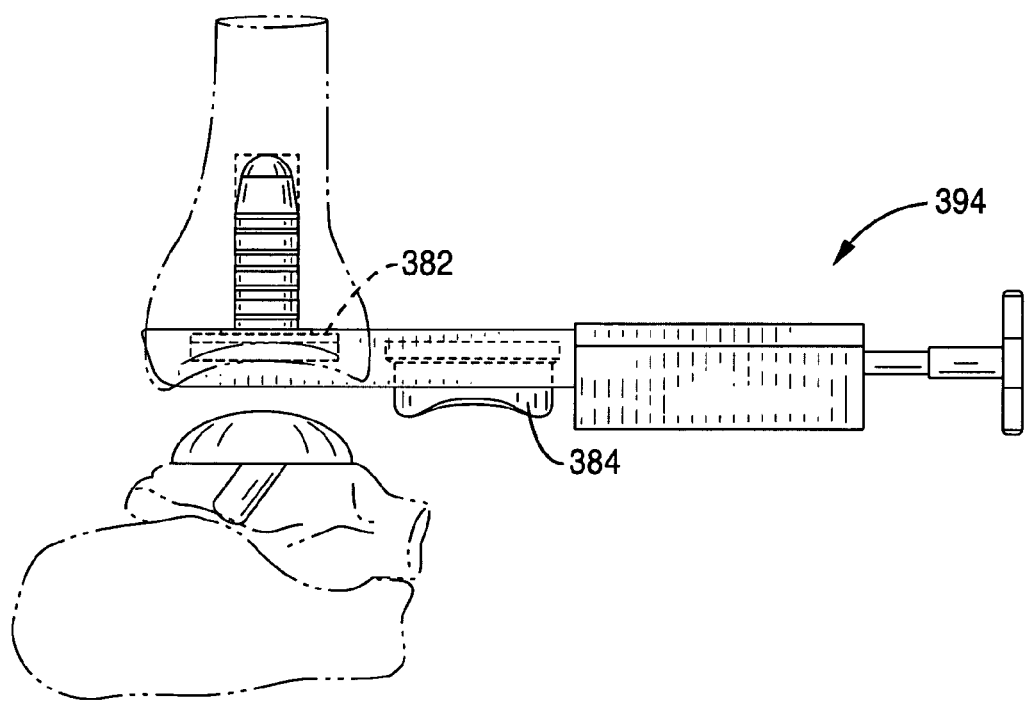
FIG. 34 is a side elevational view illustrating a method step of fitting a poly insert for completion of the replacement of a total ankle with the ankle prosthesis illustrated in FIG. 30.
Figure 35:
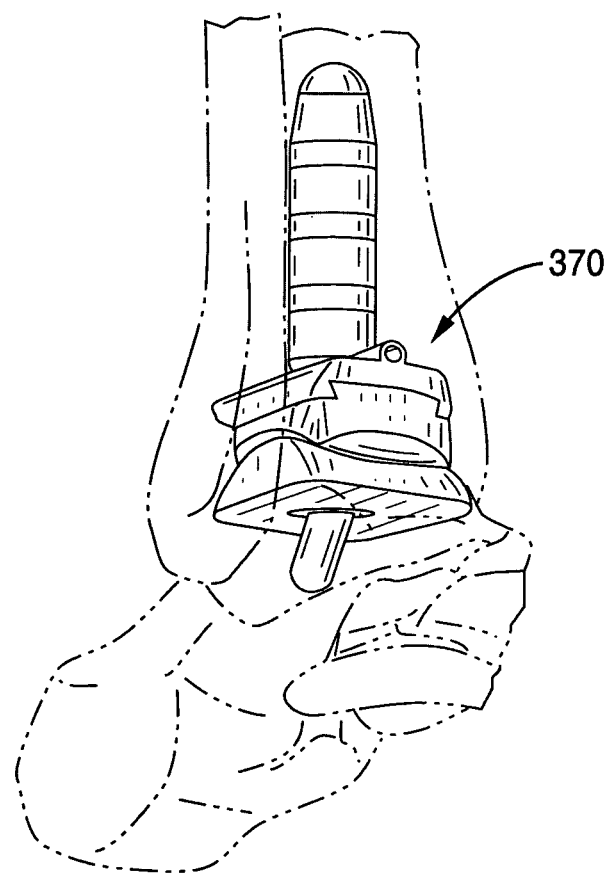
FIG. 35 is a side and front perspective view of the replacement of the total joint with the ankle prosthesis illustrated in FIG. 30.

Now referring to FIGS. 30 and 34, the poly insert component 384 is coupled to the tibial tray component 382 utilizing a poly insertion tool system 394 thereby completing the total ankle replacement with the prosthesis 370 as illustrated in FIG. 35.

Accordingly, and in one aspect, the system 10 improves the precision of bone cuts, eliminates the need for a large external frame to hold the ankle immobile, simplifies the operative procedure, decreases the operative time, minimizes the need for intra-operative fluoroscopy and allows better correction of deformities by independent bone cuts and reaming of the tibia and talus bones.

Additional Embodiments

Figure 36:
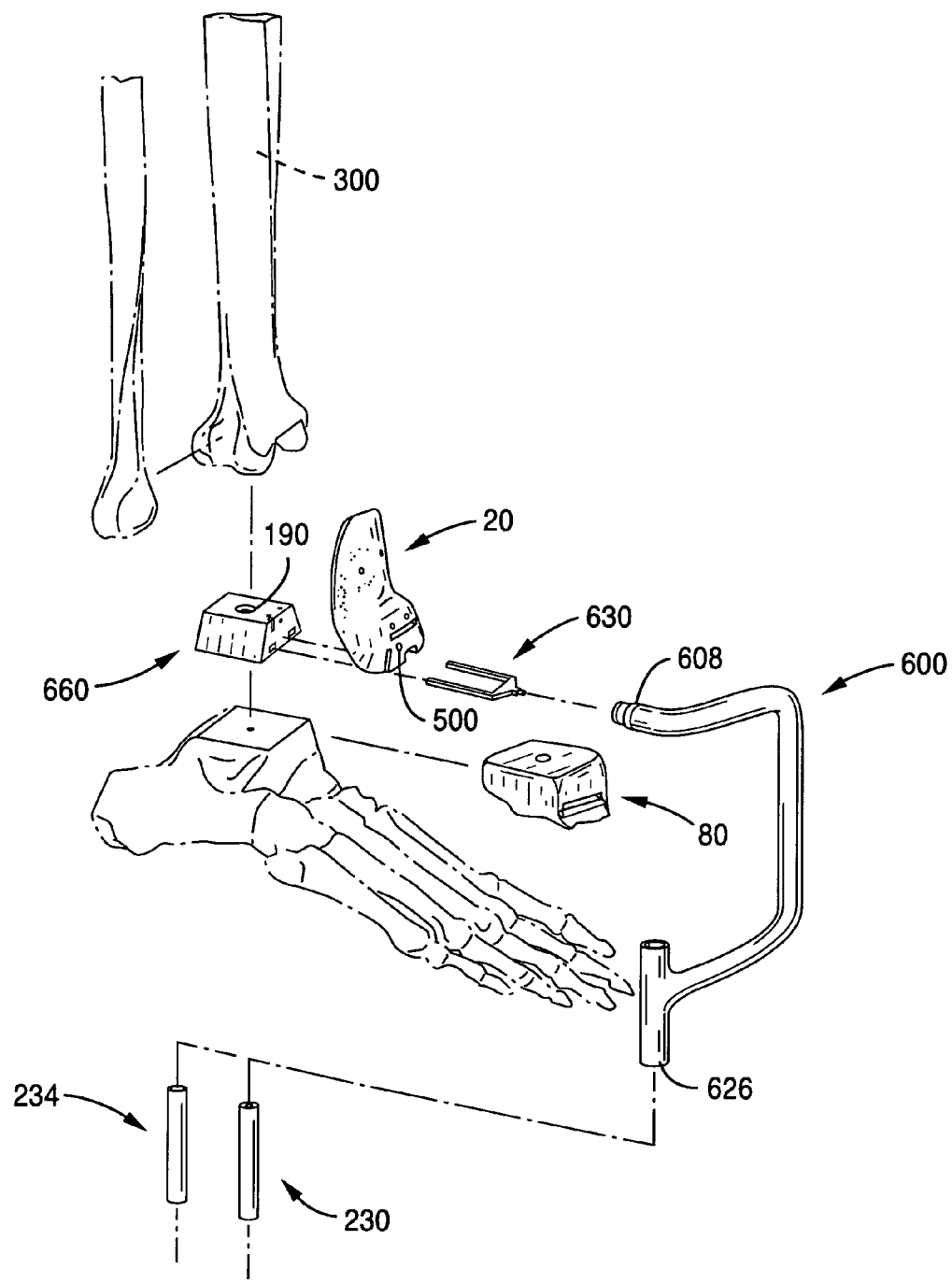
FIG. 36 is a front and side perspective view of another embodiment of a system for use in total ankle replacement surgery, the system comprising a custom tibial cutting guide, a custom talar cutting guide, a tibial reaming guide circumscribing a removable, cannulated reaming bit, a C-shaped outrigger alignment guide, a cylindrically shaped inner sleeve wire guide, an adaptor with body and extended members or a tuning fork shaped adaptor, and further illustrating a fragmentary front and side perspective view of a human leg and foot illustrating an ankle joint comprised of a fibula and a prepared tibia of the leg, and a prepared talus of the top of the foot.

FIGS. 36 through 90 illustrate further embodiments of the custom tibial cutting guide 20, the tibial reaming guide 160, and the C-shaped outrigger alignment guide 200 that are delineated in detail above.

For example, FIG. 36 illustrates an embodiment of the custom tibial cutting guide 20 further comprising a radiographic insert guide hole or alignment hole 500, a C-shaped outrigger alignment guide 600 having a general shape of the C-shaped outrigger alignment guide 200, and a custom tibial reaming guide 660 having a general shape of the custom tibial reaming guide 160.

Custom Tibial Guide 20 Having Radiographic Insert Guide Hole 500

Figure 37:
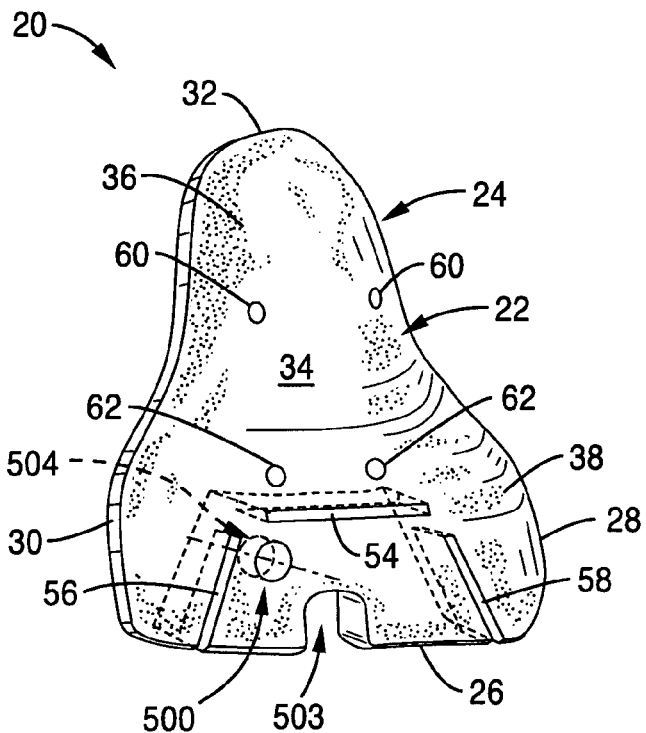
FIG. 37 is a front perspective view of another embodiment of a custom tibial cutting guide illustrating bone fixation holes, tibial reaming guide fixation holes, saw cutting guides, a notch for passage of a fixation pin into the tibial reaming guide, and a hole for placement of a radiographic guide device or an adjustment screw device.
Figure 38:
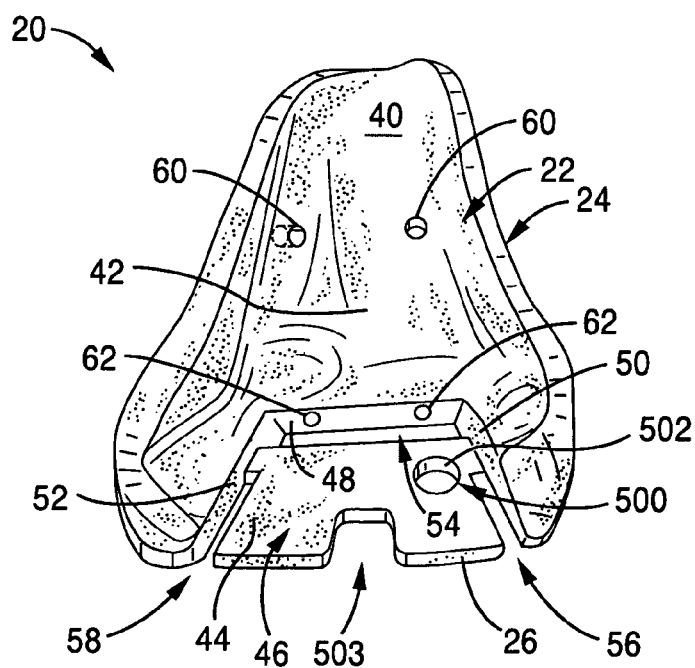
FIG. 38 is a back perspective view of the custom tibial cutting guide illustrated in FIG. 37 and showing bone fixation holes, tibial reaming guide fixation holes, saw cutting slits, the notch for passage of a fixation pin into the tibial reaming guide, and a posterior surface that has a patient specific topography that is a preoperatively defined negative or inversion of an anterior topography or surface of a distal portion of the patient's tibia.
Figure 39:
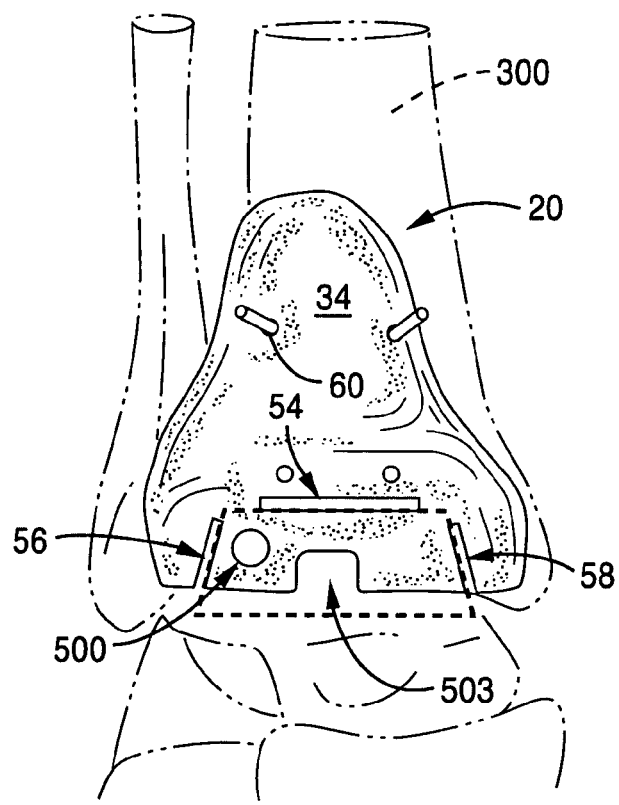
FIG. 39 is a front elevation view of the custom tibial cutting guide illustrated in FIG. 37 and shown fit in place against the anterior surface of the distal portion of the tibia and removeably secured thereto.

More specifically, and referring to FIGS. 37 through 39, one embodiment of the custom tibial guide 20 further comprises the radiographic insert guide hole 500 defined by a circumscribing interior surface 502 that extends from the anterior surface 34 through the guide 20 to the posterior surface 44 of the posterior locator notch 46, in the inferior portion of the guide 20. In one embodiment, the interior surface 502 is cylindrically shaped thereby defining a cylindrically shaped radiographic insert guide hole 500. Additionally, and in one embodiment, the radiographic insert guide hole 500 is located just inferior to the superior tibial cutting slit 54 and in the area defined by the bone cutting slits either along the lateral side adjacent to the lateral cutting slit 56 or along the medial side adjacent to the medial malleolus cutting slit 58. The cylindrically shaped interior surface 502 defining the cylindrically shaped radiographic insert guide hole 500 has a central axis 504 that is parallel to an anterior to posterior extending axes of the bone cutting slits 54, 56, and 58.

Radiographic Insert Guide 510

Figure 40:
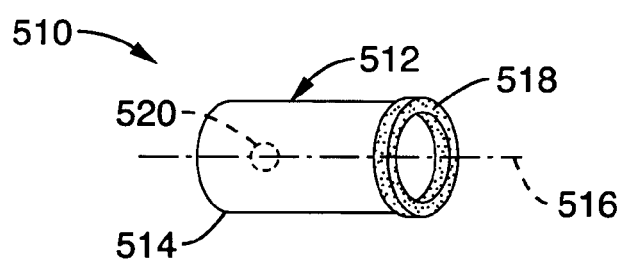
FIG. 40 is a front and side perspective view of a radiographic insert guide device comprised of a radiodense material that forms a circular anterior rim with a cylindrical body that is formed of radiolucent material, and a radiodense sphere embedded near the posterior end of the body, the cylindrical body is sized to will fit into a hole in the custom tibial guide.
Figure 41:
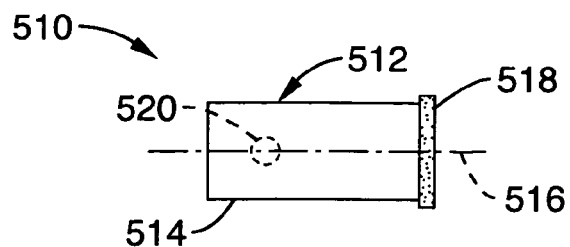
FIG. 41 is a side elevational view of the radiographic insert guide device illustrated in FIG. 40.

FIGS. 40 and 41 illustrate an embodiment of a radiographic insert guide 510 that is sized to be received at least partially within the radiographic insert guide hole 500 of the custom tibial guide 20 as illustrated in at least FIG. 41.

Figure 42:
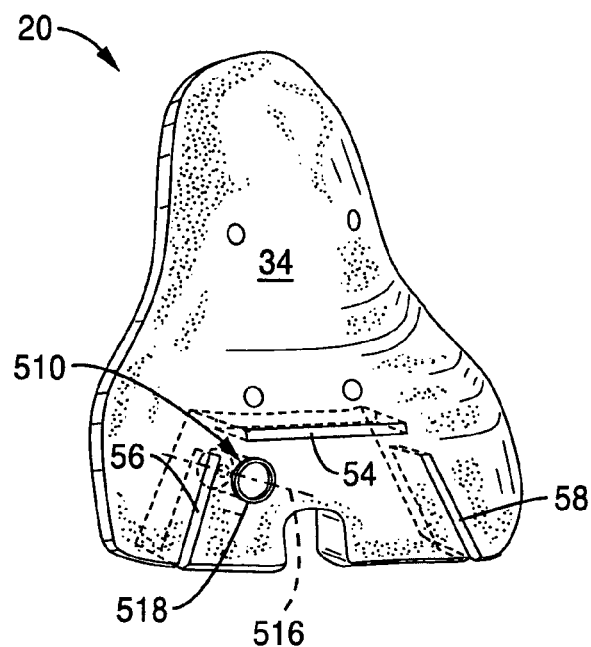
FIG. 42 is a front perspective view of the custom tibial cutting guide illustrated in, for example, FIG. 37 and showing the radiographic insert guide device in place in the hole for its placement.

More specifically and still referring to FIGS. 38 through 43, an embodiment of the radiographic insert guide 510 is comprised of a cylindrically shaped solid body 512 having a smooth exterior surface 514 and a central longitudinal axis 516. The radiographic insert guide 510 is also comprised of a radially outwardly extending anterior circular radiodense ring 518 disposed on an anterior end of the body 512 for acting as a radially outwardly extending rim that abuts or seats against the anterior surface 34 (FIG. 42) of the custom tibial guide 20 when the cylindrically shaped body 512 is complementally received within the radiographic insert guide hole 500. The radiographic insert guide 510 is further comprised of a small radiodense sphere 520 that is embedded within the cylindrically shaped solid body 512 at a location proximate a posterior end of the body 512. In one embodiment, the center of the small radiodense sphere 520 is substantially aligned along the central longitudinal axis 516 of the body 512 of the radiographic insert guide 510. The cylindrically shaped solid body 512 of the radiographic insert guide 510 is sized to frictionally fit snugly into the radiographic insert guide hole 500 having, in one embodiment, the interior surface 502 that is smooth as illustrated in FIG. 42. In one embodiment, the cylindrically shaped solid body 512 is formed from, but not limited to, a radiolucent plastic material.

Figure 44:
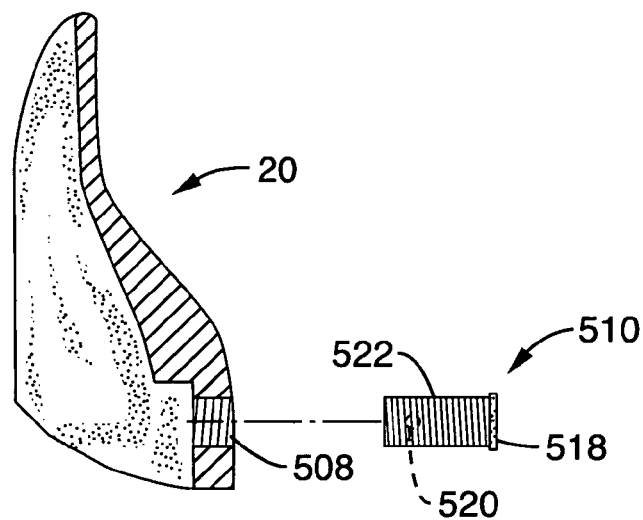
FIG. 44 is a side sectional view of custom tibial guide illustrated in, for example, FIG. 37 and showing threads in the hole, and a side elevational view of an embodiment of the radiographic guide insert device having corresponding threads on the cylindrical body thereof.

In another embodiment, and referring to FIG. 44, the interior surface 502 of the radiographic insert guide hole 500 includes interior threads 508 and the radiographic insert guide 510 includes exterior threads 522 for threadedly coupling the exterior threads 522 with the interior threads 508 such that the radiodense ring 518 disposed on the anterior end of the body 512 abuts or seats against the anterior surface 34 of the custom tibial guide 20.

Radiographic Insert Guide Use and Operation

In use and operation, and referring to FIGS. 37 through 44, the radiographic insert guide 510 is frictionally or threadedly coupled in the radiographic insert guide hole 500 so that the radiodense ring 518 disposed on the anterior end of the body 512 of the guide 510 abuts or seats against the anterior surface 34 of the custom tibial guide 20 prior to the custom tibial guide 20 being positioned over the anterior surface portion 306 of the distal portion 304 of the tibia 300. Then, the custom tibial guide 20 is positioned over the anterior surface portion 306 of the distal portion 304 of the tibia 300 and an intraoperative x-ray or fluoroscopy is used to verify the position of the custom tibial guide 20 relative to the ankle 290. In particular, with the custom tibial guide 20 in position, the x-ray or fluoroscopy should demonstrate that the custom tibial guide 20 is in the proper bone cutting alignment position by displaying the image of the radiodense sphere 520 in a centered relationship with respect to the anterior circular radiodense ring 518 (FIG. 43) when the x-ray beam shoots directly along the longitudinal axis 516 of the radiographic insert guide 510. That axis is also parallel to the axes of the bone cutting slits 54, 56, and 58. Therefore, the position of the bone cutting slits relative to the ankle bones can be assessed with fluoroscopy prior to the surgeon actually making the bone cuts. If the position is not satisfactory, the custom tibial guide could be repositioned, with the radiographic insert guide 210 being utilized for allowing the surgeon to determine the proper alignment intraoperatively.

C-shaped Outrigger Alignment Guide 600

As noted above with reference to FIG. 36, and in another embodiment, the system 10 further comprises the C-shaped outrigger alignment guide 600. The C-shaped outrigger alignment guide 600 has the general shape of the C-shaped outrigger alignment guide 200 with an exception of having a superior end or head 608 that is different than superior end or head 208 of alignment guide 200.

Figure 45:
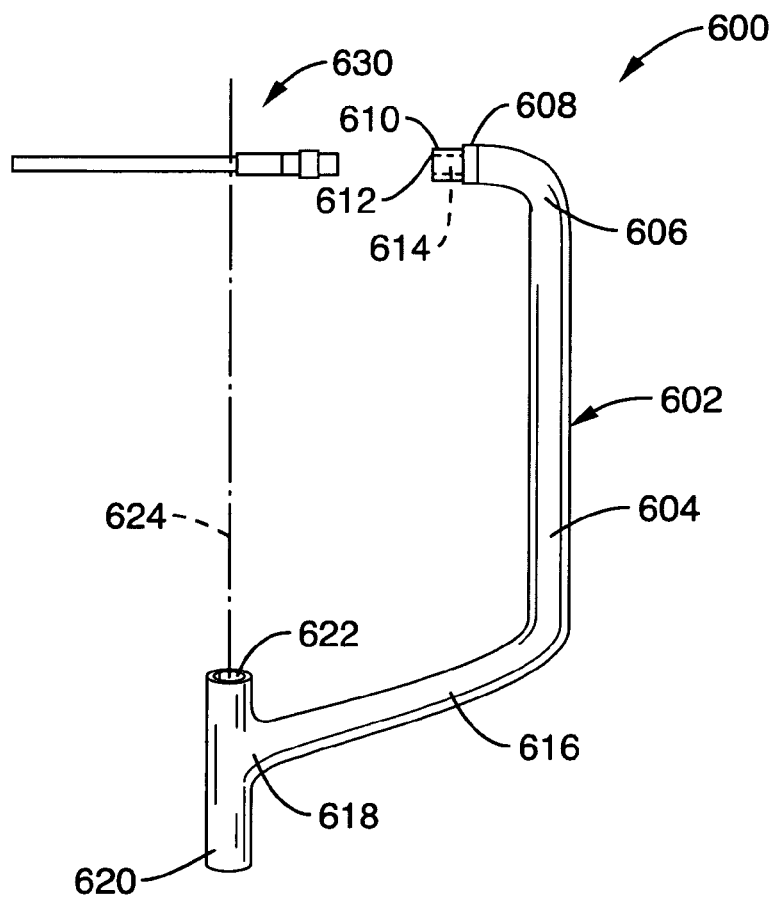
FIG. 45 is a side elevational view of another embodiment of a C-shaped outrigger guide comprising a tuning fork shaped adapter.

In particular, and referring to FIG. 45, the C-shaped outrigger alignment guide 600 is comprised of an arcuate or generally C-shaped body 602 comprised of a medial section 604 transitioning at one end to a superior section 606 and at the other end to an inferior section 616.

The superior section 606 generally perpendicularly extends away from the medial section 604 in substantially the same plane as the medial section 604, and then arches or bends out of the plane of the medial section 604 and transitions to the superior end or head 608 supporting a friction fitting 610. In one embodiment, the friction fitting 610 circumferentially steps down from and is integrally formed with the superior end 608. The friction fitting 610 is comprised of a posteriorly extending wall 612 circumscribing interior surface defining a blind bore 614. The blind bore 614 is sized to receive and frictionally fit with a complementally shaped end of a tuning forked shaped adaptor 630 which, in turn, is received by a custom tibial reaming guide for aligning the C-shaped outrigger alignment guide 600 in a stable position relative to the central long axis 302 of the tibia 300 as will be further delineated below.

The inferior section 616 generally perpendicularly extends away from the medial section 604 in substantially the same plane as the medial section 604, and then arches or bends out of the plane of the medial section 604 and transitions to an inferior end 618 supporting an inferior cylindrically shaped inferior sleeve attachment or distal sleeve 620 having an open ended cylindrically shaped bore 622 axially extending therethrough and having a central axis 624.

The distal sleeve 620 is integrally formed with and extends from both sides of the inferior end 618, and is spaced from and generally parallel with the medial section 604. The open ended cylindrically shaped bore 622 of the distal sleeve 620 is sized to closely receive two removable, alternate inner sleeve guides: the cylindrically shaped inner sleeve wire guide 230 (FIG. 13) having a open ended cylindrically shaped interior bore 232 extending therethrough and the cylindrically shaped inner sleeve drill and driver bit guide 234 (FIG. 13) having open ended cylindrically shaped interior bore 236 extending therethrough.

As described above, the open ended cylindrically shaped interior bore 232 of the wire guide 230 is sized to closely receive and pass a thin wire such as the K-wire 412 therethrough and the open ended cylindrically shaped interior bore 236 of the drill and driver bit guide 234 is sized to closely receive and pass either the cannulated drill bit 414 or the cannulated driver bit 416 therethrough. The open ended cylindrically shaped interior bore 236 of the drill and driver bit guide 234 is of a larger diameter than the diameter of the open ended cylindrically shaped interior bore 232 of the wire guide 230.

In one embodiment, the C-shaped outrigger alignment guide 600 is made out of, but not limited to, a metal material and is constructed as, but not limited to, an integrally formed one piece instrument.

Tuning Forked Shaped Adaptor 630

Figure 46:
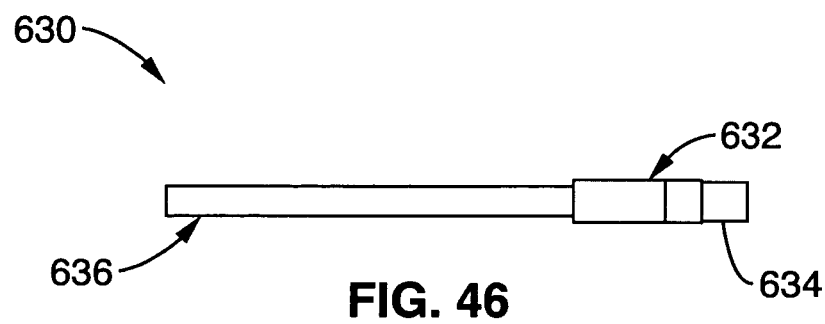
FIG. 46 is a side elevational view of the tuning fork shaped adapter illustrated in, for example, FIG. 45.
Figure 47:
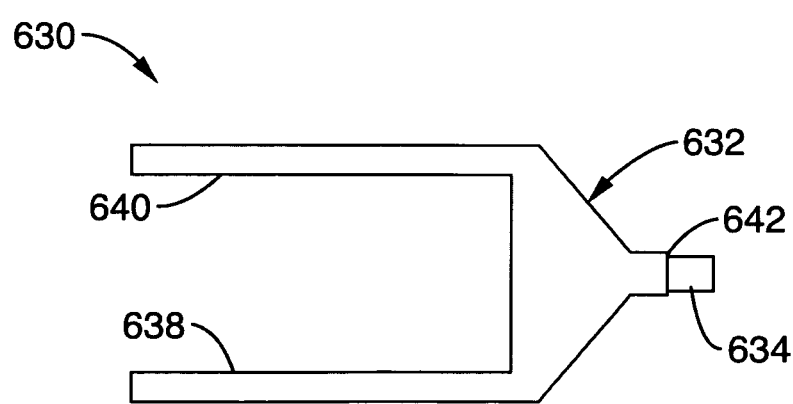
FIG. 47 is a top elevational view of the tuning fork shaped adapter illustrated in, for example, FIGS. 45 and 46.

Referring now to FIGS. 46 and 47, an embodiment of the system 10 comprises the tuning fork shaped adapter 630 comprised of a body 632 having a friction fitting end portion 634 sized and shaped to be received and frictionally fit within the blind bore 614 of the C-shaped outrigger alignment guide 600 and an opposing forked end portion 636 comprised of spaced apart furcations or tines 638, 640 having a specific length for attaching or coupling to a tibial reaming guide as will be further delineated in detail below. The tuning fork shaped adapter 630 further comprises a stop portion 642 disposed at a distal end of the friction fitting end portion 634 for abutting against a front face of the circumscribing wall 612 of the C-shaped outrigger alignment guide 600 for precisely locating the tuning fork shaped adapter 630 onto the C-shaped outrigger alignment guide 600.

In one embodiment, a specific tuning fork shaped adapter can be provided for each different size of each tibial reaming guide. For example, the tuning fork shaped adapter 630 is sized to be received by reaming guide 660 as illustrated in FIG. 36. Accordingly, a specific tuning fork shaped adapter can be provided for each tibial reaming guide size such that for each matching set of adapter and reaming guide a width between the tines on the adaptor matches a width between corresponding channels of the reaming guide. The length of the tines can also be specific to each matching set of adapter and reaming guide.

In one embodiment, each tuning fork shaped adapter is made out of, but not limited to, a metal material and is constructed as, but not limited to, an integrally formed one piece instrument.

Tibial Reaming Guide 660

As noted above, and as illustrated in FIG. 36, the custom tibial reaming guide 660 is another embodiment of the tibial reaming guide 160 and generally follows the same manufacturing protocol as the tibial reaming guide 160 for providing a range of sizes that correspond to the different selection of prosthesis sizes 362. Accordingly, the custom tibial reaming guide 660 has a shape that is generally analogous to tibial reaming guide 160.

Figure 48:
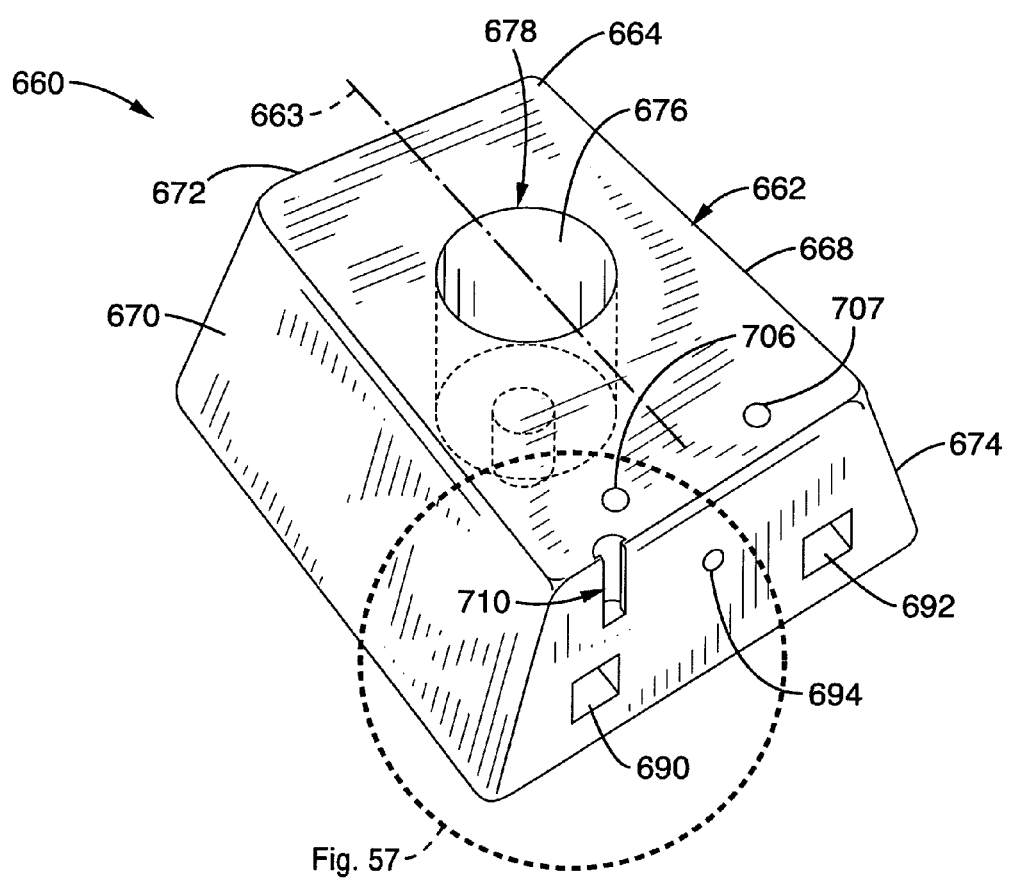
FIG. 48 is a top, front, and side perspective view of another embodiment of a tibial reaming guide having a central body channel circumscribing the removable, cannulated reaming bit, and further a hole for a fixation pin passing through the anterior face to the central channel, fixation holes for removeably attaching the tibial reaming guide to the custom tibial guide, channels that pass through the anterior face in the inferior half of the body for attachment of the tuning fork shaped adaptor, and a vertical channel in the superior anterior face for attachment of the adjustment screw device.
Figure 49:
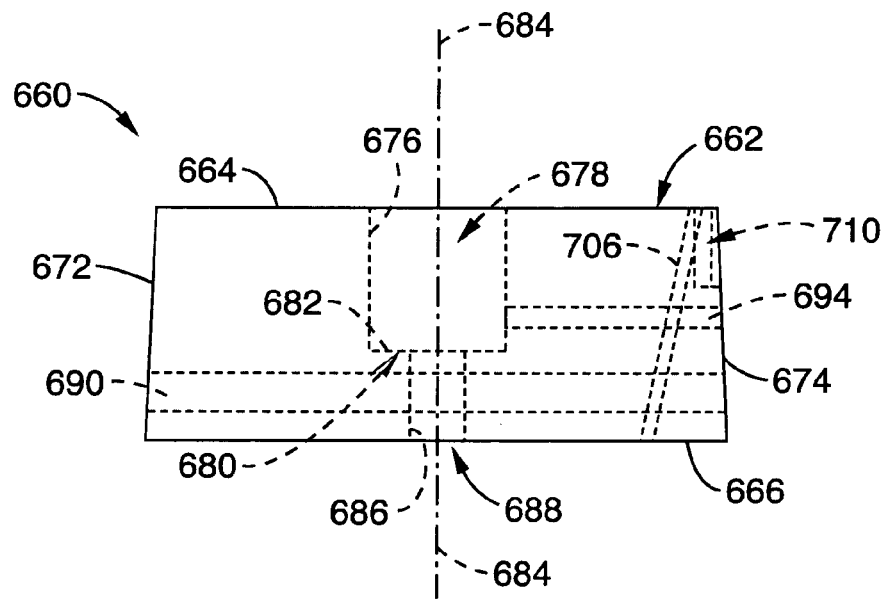
FIG. 49 is a side view of the tibial reaming guide illustrated in FIG. 48 and showing in phantom lines the central channel having an annular shoulder, a channel for a fixation pin passing through the anterior face to the central channel, oblique fixation holes for removeably attaching the tibial reaming guide to the custom tibial guide, channels that pass through the anterior face in the inferior half of the body for attachment of the tuning fork shaped adapter, and a vertical channel in the superior anterior face for attachment of the adjustment screw.
Figure 50:
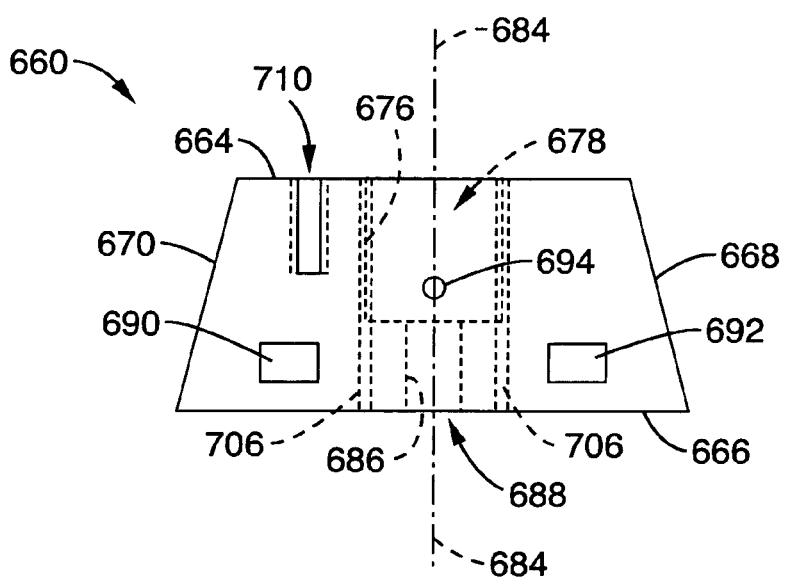
FIG. 50 is a front elevational view of the tibial reaming guide illustrated in FIGS. 48 and 49.

Referring to FIGS. 48 through 50, and in particular, the custom tibial reaming guide 660 is comprised of a generally pyramidal frustum shaped reamer body 662 that is designed to fit into the tibial-talar space 342 defined as the space between the tibia 300 and the talus 330 after the resected tibial and talar bone segments have been removed. Accordingly, the reamer body 662 corresponds to the size of the chosen prosthesis 370 to be used, so if there are five different prosthesis sizes to choose from then there are five different tibial reaming guide sizes for providing a one to one correspondence between the two.

Additionally, the generally pyramidal frustum shaped reamer body 662 is comprised of six faces: a superior face 664, an inferior face 666, an inner face 668, an outer face 670, a posterior face 672, and an anterior face 674. The superior and inferior faces 664 and 666 have a generally square or rectangular shape while the inner face 668, outer face 670, posterior face 672, and anterior face 674 have a generally trapezoidal shape.

Furthermore, the reamer body 662 of the tibial reaming guide 660 is comprised of a first interior cylindrical surface 676 that has a first inside circumference that defines a first cylindrically shaped central channel 678 that extends from an opening in the superior face 664 to an annular stepped shoulder 680 disposed substantially parallel to the superior face 664. The annular stepped shoulder 680 forms an axially directed stop surface 682. A central longitudinal axis 684 of the first cylindrically shaped central channel 678 is substantially perpendicular to both the superior face 664 and the annular stepped shoulder 680. The open ended cylindrically shaped central channel 678 is sized to receive the cannulated reaming bit 190 (FIGS. 11 and 12) comprised of the axial passage 192 extending through the interior of the cannulated reaming bit 190 and a bone reaming exterior surface comprised of front cutting threads 194 and side cutting threads 196.

Moreover, a second interior surface 686 has a second inside circumference less than the first inside circumference of the first interior cylindrical surface 676 and defines a second central channel 688 that extends from an opening in the annular stepped shoulder 680 to an opening in the inferior face 666. Accordingly, the first cylindrically shaped central channel 678 and the second central channel 688 are in open communication with one another and in open communication between the openings in the superior face 664 and the inferior face 666. Additionally, the central longitudinal axis 684 of the first cylindrically shaped central channel 678 is also the central longitudinal axis of the second central channel 688. Furthermore, and in one embodiment, the second central channel 688 comprises a cylindrically shaped second interior surface 686 or a conically shaped second interior surface 686 with an inferior end having a wider diameter and tapering to a narrower diameter at the level of the annular stepped shoulder 680, with the conical shape guiding the reamer driver 416 to the opening at the annular stepped shoulder 680 having a diameter large enough to allow passage therethrough.

In one situation, the central longitudinal axis 684 aligns or is coincident with the central axis 302 of the tibia 300 when the trapezoidally shaped anterior face 674 of the reamer body 662 abuts against the trapezoidally shaped posterior surface portion 44 of the reaming guide locator notch 46 and when the custom tibial cutting guide 20 is placed against the anterior surface portion 306 of the distal portion 304 of the tibia 300 with a portion of the reamer body 662 received within the tibial-talar space 342. Thus, when the cannulated reaming bit 190 is received within the first cylindrically shaped central channel 678, the shape of the custom tibial cutting guide 20 and the depth of the locator notch 46 in its distal end combine to set the alignment of the axial passage 192 of the cannulated reaming bit 190 with the central axis 302 of the tibia 300 for reaming of the tibia 300 along its central axis 302 with the reaming exterior front and side cutting threads 194, 196 of the cannulated reaming bit 190. The diameter of the first cylindrically shaped central channel 678 of the reamer body 662 is sized to closely receive the cannulated reamer bit 190 and the annular stepped shoulder 680 forms the axially directed stop surface 682 for supporting the cannulated reamer bit 190. The cannulated reamer bit 190 is of the size needed to ream the tibial blind bore 328 for the size of the tibial stem or, in one embodiment, the modular tibial stem components 372 of the size of the preoperatively chosen prosthesis 370.

Attachment Channels 690, 692

Figure 51:
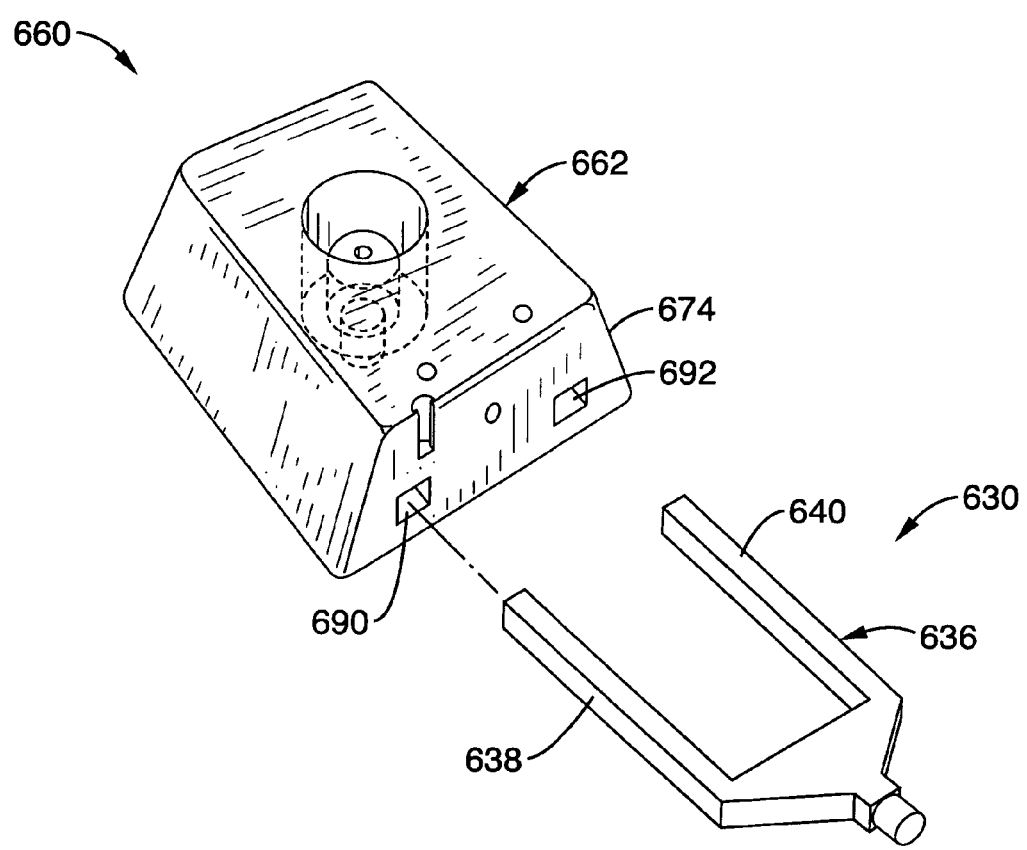
FIG. 51 is a top, front, and side perspective view of the tibial reaming guide illustrated in FIGS. 48 through 50 and showing tines of the tuning fork shaped adapter aligned with the channels that open through the anterior face of the tibial reaming guide.

Referring now to FIG. 51, the reamer body 662 of the custom tibial reaming guide 660 is comprised of two attachment channels 690, 692 for respectively receiving the spaced apart furcations or tines 638, 640 of the forked end portion 636 of the tuning forked shaped adapter 630 (FIG. 51).

The two attachment channels 690, 692 pass from the anterior surface 674 of the custom tibial reaming guide 660, and pass through the inferior half of the body 662 of the tibial reaming guide 660, and may pass through the entire body, but at least to a depth to accommodate the length of the tines 638, 640 on the tuning forked shaped adapter 630 of the length corresponding to that tibial reaming guide, and with a width of separation between the channels 690, 692 corresponding to the width of separation between the tines 638, 640 on the corresponding tuning fork adapter 630.

Use and Operation of Attachment Channels and Tines

Figure 52:
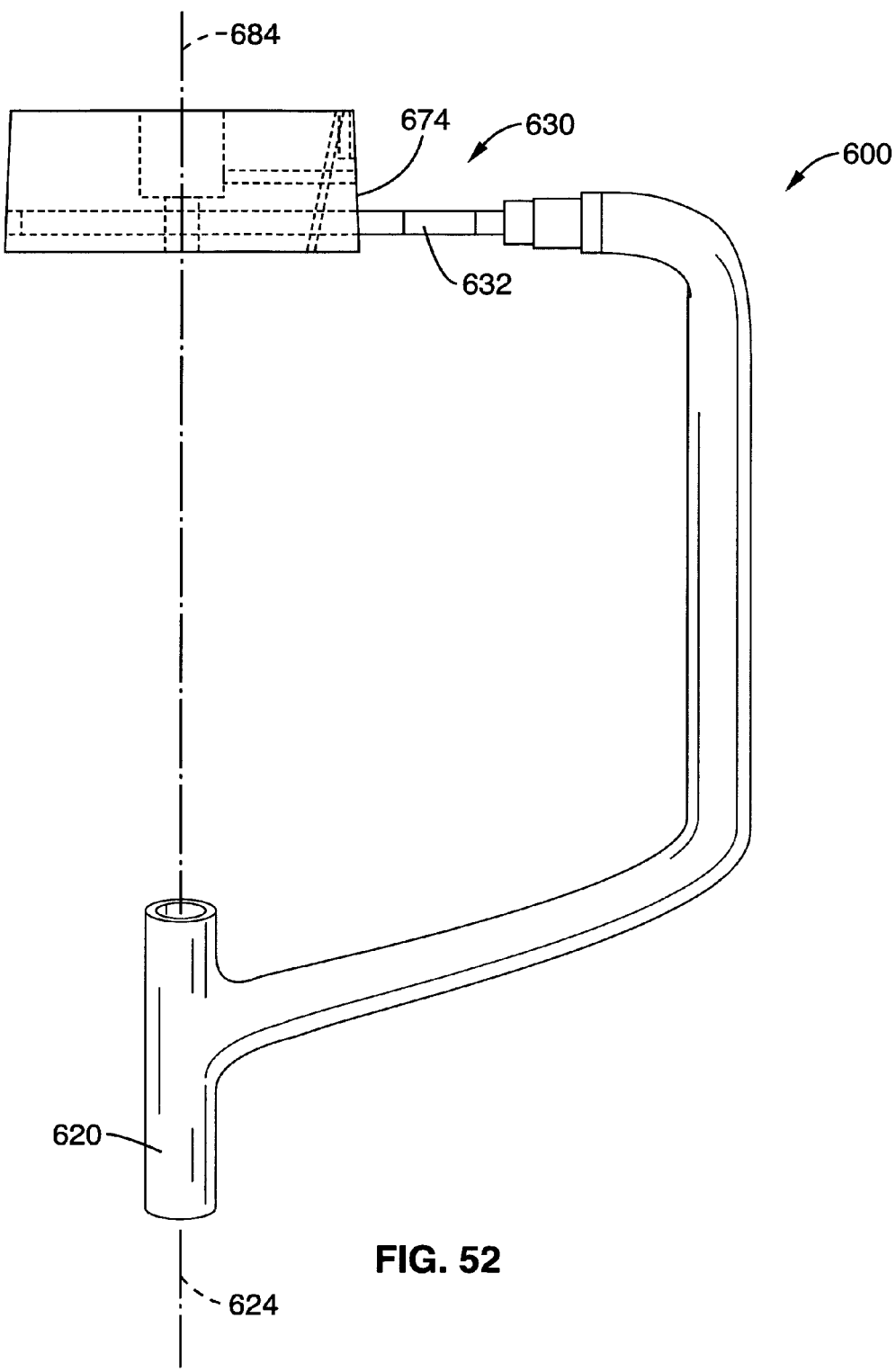
FIG. 52 is a side sectional view of the tibial reaming guide illustrated in FIGS. 48 through 51 being supported by the tuning fork shaped adapter of the C-shaped outrigger guide illustrated in, for example, FIG. 45 by the tines of the tuning fork shaped adapter fitting into their corresponding channels in the inferior body of the tibial reaming guide and further illustrating the tuning fork adapter fixed to the superior head of the C-shaped outrigger guide through a friction fitting, and the alignment of the central axis of the central channel of the tibial reaming guide with the axis of a distal sleeve of the C-shaped outrigger guide.
Figure 55:
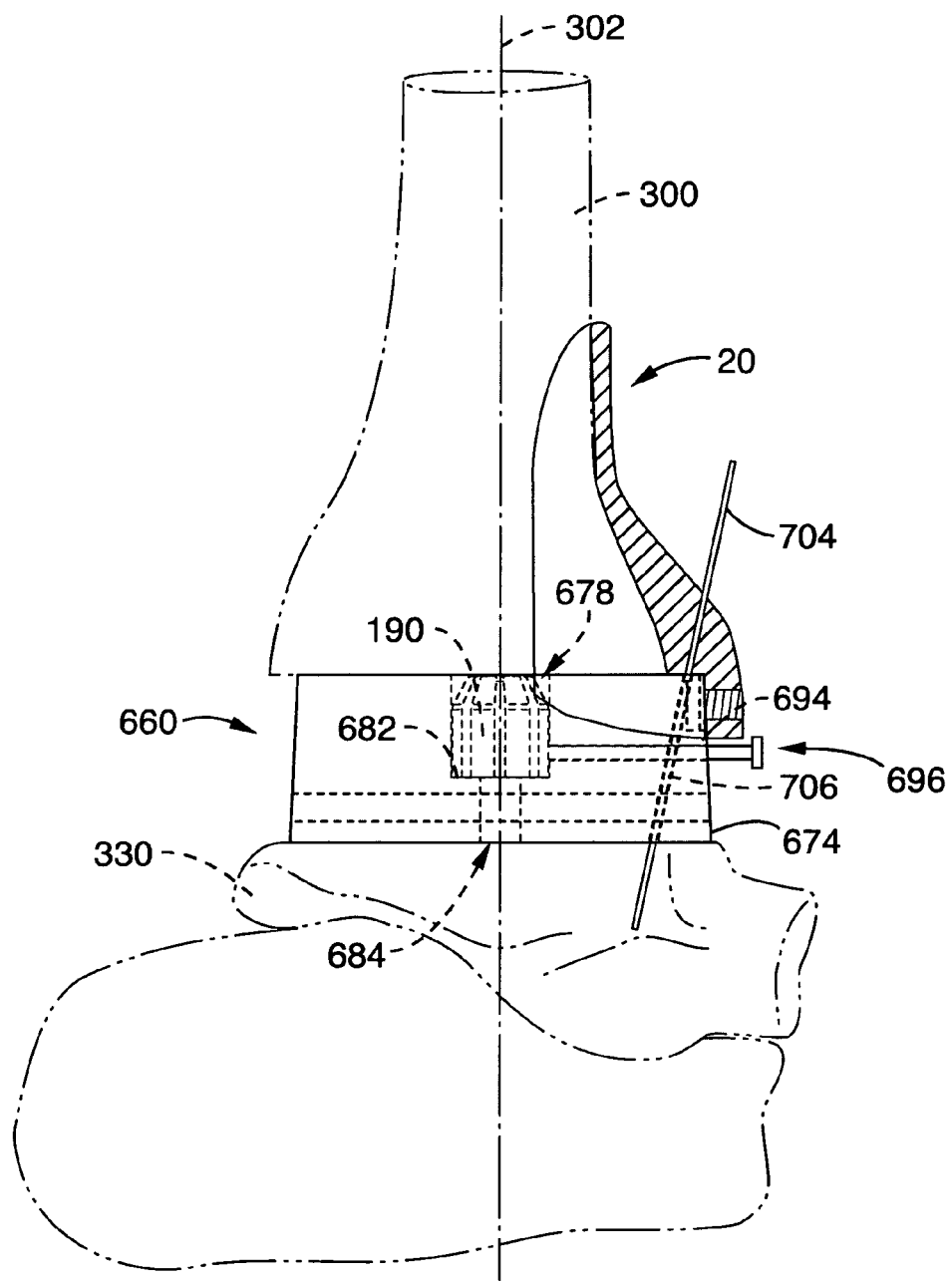
FIG. 55 is a side sectional view of the tibial reaming guide as illustrated in FIGS. 48 through 54, in place between the tibia and talus bones after the bone cuts have been made, set into position to align the axis of the central channel with the axis of the distal tibia by the relationship with the posterior notch of the custom tibial guide, and removeably fixed to the custom tibial guide and the talus.

Referring to FIGS. 51 and 52, tines 638, 640 of the tuning fork shaped adapter 630 fit into the respective channels 690, 692 disposed in the tibial reaming guide 660. In particularly, and as illustrated in FIG. 55, when the anterior surface 674 of the tibial reaming guide 660 is completely seated against the body 632 of the tuning fork shaped adapter 630, and the friction fitting 634 of the tuning fork shaped adapter 630 has engaged the friction fitting 610 (FIG. 45) of the C-shaped outrigger alignment guide 600, the axis 684 of the first and second central channels of tibial reaming guide 660 will align with the axis 624 of the distal sleeve 620 of the C-shaped outrigger alignment guide 600.

Fixation Pin and Hole for Reamer Bit Fixation

Figure 53:
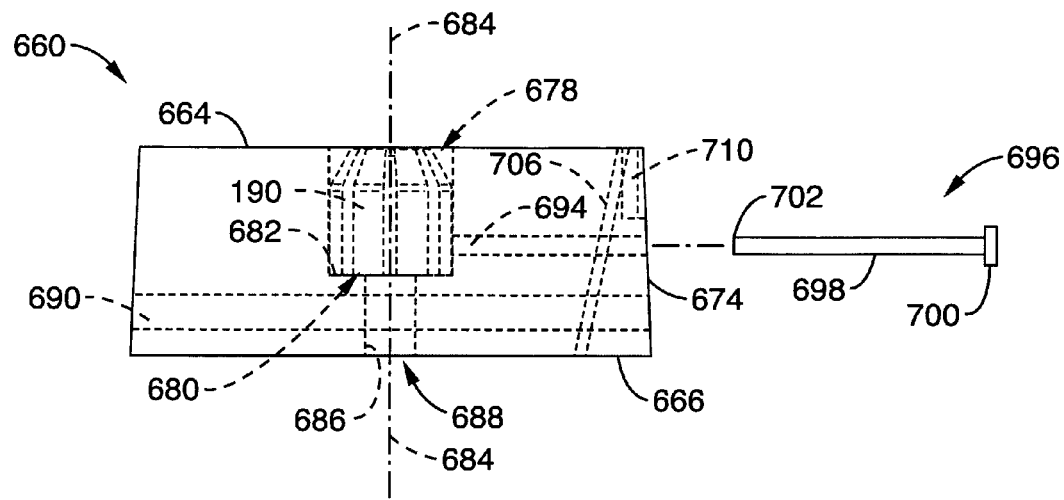
FIG. 53 is a side sectional view of the tibial reaming guide illustrated in FIGS. 48 through 52 and showing the tibial reaming bit in the central channel with a fixation pin aligned with the anterior hole in the reaming guide for the channel that communicates with the central channel.
Figure 54:
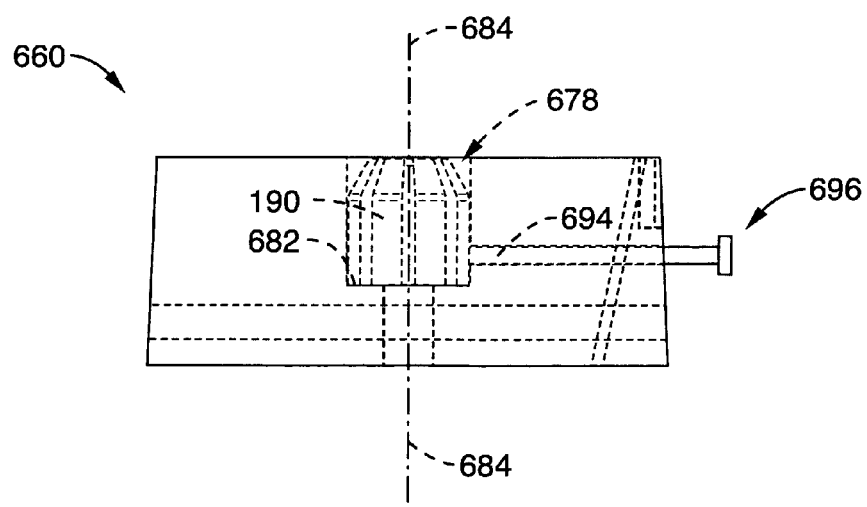
FIG. 54 is a side sectional view of the tibial reaming guide illustrated in FIGS. 48 through 53, with a fixation pin in the channel that communicates from the anterior border of the reaming guide and fixes into the tibial reamer bit to stabilize it in the central channel.

Referring to FIGS. 53 and 54, and in another embodiment, the tibial reaming guide 660 comprises a fixation pin hole or channel 694 that passes from the anterior surface 674 of the tibial reaming guide 660 into the central channel 678 with a diameter large enough to allow passage of a fixation pin 696. The fixation pin 696 comprises a body 698 that is sized to pass through fixation pin hole or channel 694 in tibial reaming guide 660, a head 700 at one end of the body, and a working end 702 at the other end of the body 698 that engages the tibial reaming bit 190 when it sits on the stop surface or ledge 682 in the central channel 678 of the tibial reaming guide 660 as illustrated in FIG. 54. This engagement stabilizes the tibial reaming bit 190 within the central channel 678.

In use and operation, and referring to FIGS. 53 through 56 the tibial reaming bit 190 is placed within the central channel 678 and is axially stopped by and sits upon stop surface or ledge 682. The fixation pin 696 is passed through the notch 503 (FIG. 37) in the custom tibial guide 20 and through the channel 690 from the anterior face 674 of the tibial reaming guide 660 and into the central channel 678, where the working end 702 of the pin 696 engages the tibial reaming bit 190 for stabilizing the tibial reaming bit 190 in the central channel 678. Then, the tibial reaming guide 660 with the tibial reaming bit 190 stabilized within the central channel 678 by the fixation pin 696 is nestled within locator notch 46 (FIG. 38) of the custom tibial guide 20, and a stabilization pin 704 is drilled through each of the oblique channels 706 from the inferior surface 666 of the tibial reaming guide 660, exiting the guide at the superior surface 664, and then drilling up through the custom tibial cutting guide 20. The custom tibial cutting guide 20 is applied to the anterior distal tibia 300 in its unique position with the tibial reaming guide 660 inside the space between the distal tibia 300 and talus 330. The stabilization pin 704 is then drilled down into the talus 330.

Figure 56:
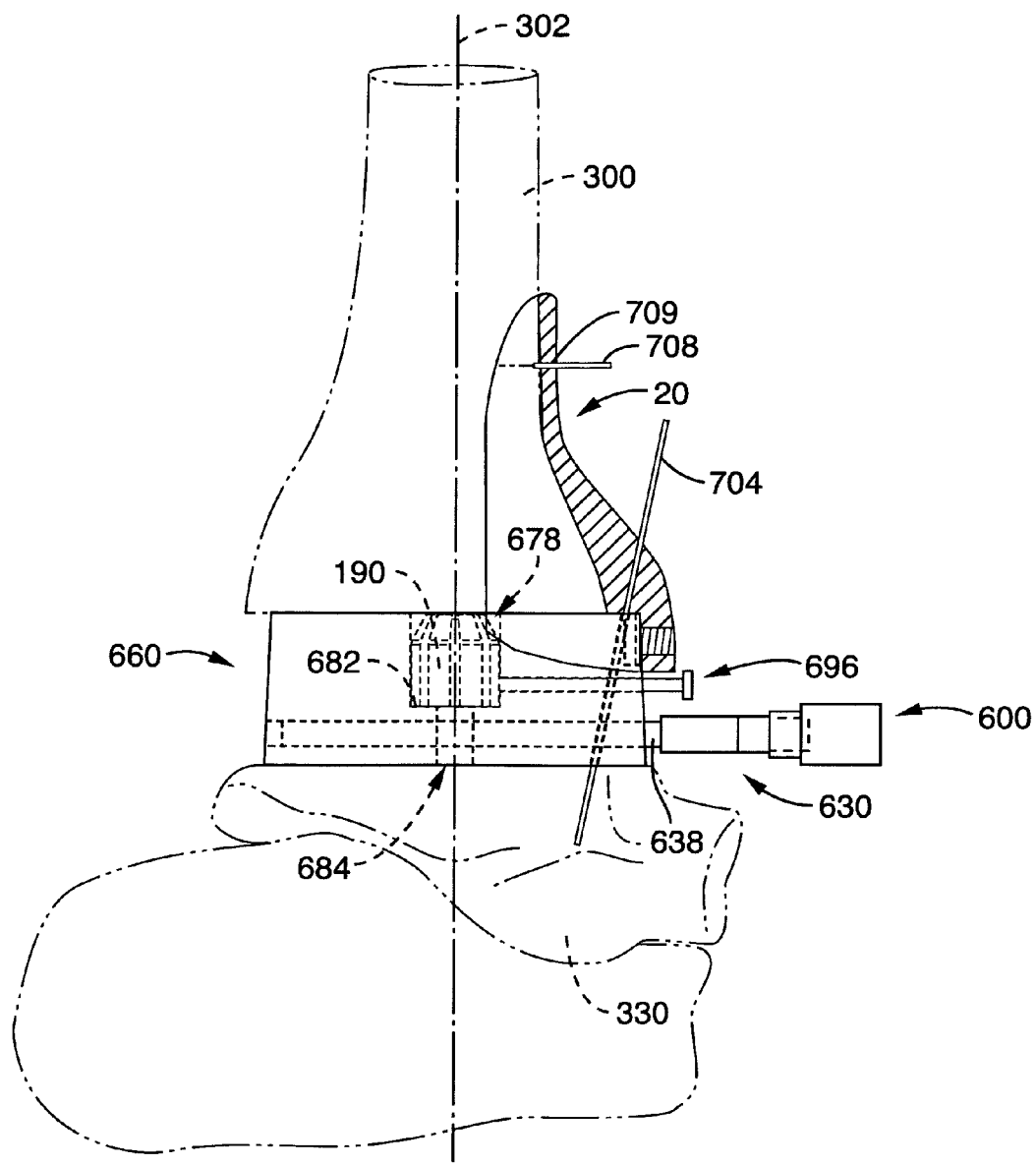
FIG. 56 is a side sectional view of the tibial reaming guide as shown in FIG. 55, with the tuning fork shaped adapter of the C-shaped outrigger guide fixed to the tibial reaming guide and showing the alignment of the central axis of the distal sleeve, the central axis of the central channel of the tibial reaming guide, and the central axis of the tibia to be in line.

As shown in FIG. 56, a fixation pin 708 is also placed through a hole 709 in the custom tibial guide 20 into the tibia 300 and the tuning fork adapter 630 is attached to the custom tibial reaming guide 660 inferior to the custom tibial cutting guide 20 through the channels 690, 692 in the tibial reaming guide 660 as delineated above. Also as delineated above, the axis 624 of the distal sleeve 620 of the C-shaped outrigger guide 600 will then align with the axis 684 of the central channel 678 and the axis 302 of the tibia 300. Now, utilizing the C-shaped outrigger guide 600 in the same manner as described above for the C-shaped outrigger guide 200, the reamer driver 416 engages the tibial reaming bit 190 and the fixation pin 696 is then withdrawn, allowing the distal tibia reaming to occur. At the completion of the reaming, the tibial reaming bit 190 is drawn back into the central channel 678 of the tibial reaming guide 660. The fixation pin 696 is then advanced so that the working end 702 of the pin 696 again engages the tibial reaming bit 190.

Adjustment

In another situation, the central longitudinal axis 684 of the custom tibial reaming guide 660 does not align or is not coincident with the central axis 302 of the tibia 300 when the trapezoidally shaped anterior face 674 of the reamer body 662 abuts against the trapezoidally shaped posterior surface portion 44 of the reaming guide locator notch 46 and when an embodiment of the custom tibial cutting guide 20 having radiographic insert guide hole 500 is placed against the anterior surface portion 306 of the distal portion 304 of the tibia 300 with at least a portion of the reamer body 662 received within the tibial-talar space 342. In this situation, adjustment is necessary.

Vertical Groove 710

Accordingly, and referring to FIG. 48, an embodiment of the tibial reaming guide 660 comprises a vertically elongated groove 710 in the anterior face 674 of the tibial reaming guide 660 that is utilized for adjusting the alignment of the central longitudinal axis 684 of the custom tibial reaming guide 660 so that it is coincident with the central axis 302 of the tibia 300.

Figure 57:
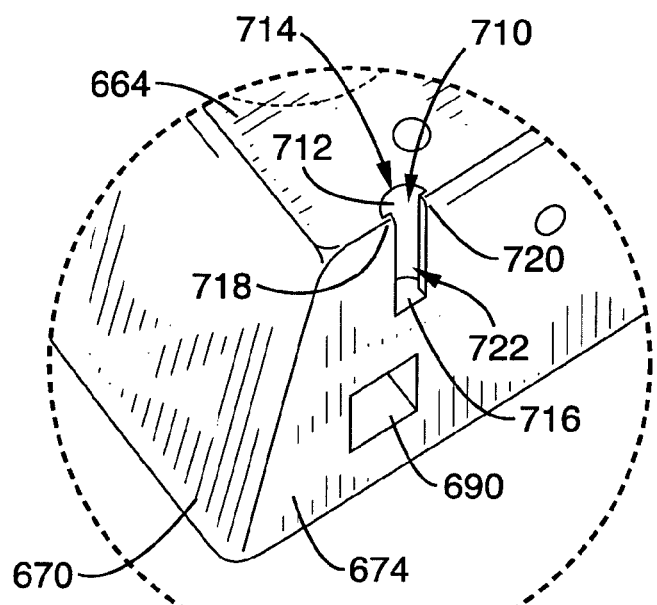
FIG. 57 is an exploded view of a portion of FIG. 48 illustrating a top, front, and side perspective view of the anterior lateral edge of the tibial reaming guide illustrated in FIG. 48 with a vertical groove in the anterior face and with lateral and central or opposing anterior flanges at the edges of the groove and further illustrating one of the channels for attachment of a tine of the tuning fork shaped adaptor.

More specifically, and referring to FIG. 57, the vertically elongated groove 710 comprises a vertically extending domed shaped interior sidewall surface 712 vertically extending between a superior arcuate shaped opening 714 in the superior face 664 to an interior arcuate shaped closed end 716. The vertically extending domed shaped interior sidewall surface 712 transitions into a vertically extending base comprised of a lateral anterior flange 718 and a central anterior flange 720 extending toward, but spaced from one another for defining an anterior rectangular opening 722 extending between the superior arcuate shaped opening 714 and the interior arcuate shaped closed end 716. The lateral anterior flange 718 and the central anterior flange 720 make the anterior rectangular opening 722 of the vertically elongated groove 710 narrower than the interior depths or, in other words, narrower than the interior diameter of the vertically extending domed shaped interior sidewall surface 712 at the base location. The function of this narrowing will be further delineated below after a detailed description of an adjustment screw 730.

Figure 58:
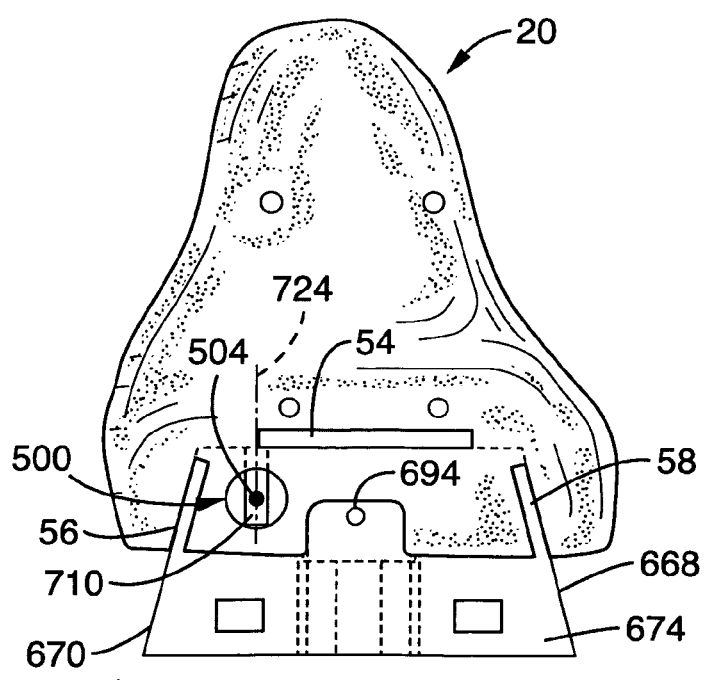
FIG. 58 is a front elevational view of the tibial reaming guide illustrated in, for example, FIG. 48 shown nestled in the notch in the posterior surface of the custom tibial guide illustrated in, for example, FIGS. 36 through 38, and showing the center of the hole in the custom tibial guide aligned with the vertical axis of the vertical groove in the tibial reaming guide, further showing the alignment of the superior, inner and outer faces of the tibial reaming guide with the superior, medial and lateral cutting slits on the custom tibial guide, further showing the hole in the anterior face of the tibial reaming guide for the pin that fixates the tibial reamer bit within the notch in the inferior surface of the custom tibial guide.

As illustrated in FIG. 58, and when in use and operation, the central axis 504 of the radiographic insert guide hole 500 aligns with a vertically extending central axis 724 of the vertically elongated domed shaped groove 710. In other embodiments delineated below, the central axis 504 of the radiographic insert guide hole 500 aligns with a central axis of a vertical groove 910 on an anterior face 874 of a custom truncated tibial reaming guide 860, a central axis of a vertical groove 1010 on an anterior face 974 of a custom reversible tibial reaming guide 960, or a central axis of a vertical groove 1110 on a posterior face 972 of the custom reversible tibial reaming guide 960.

Adjustment Screw 730

Figure 59:
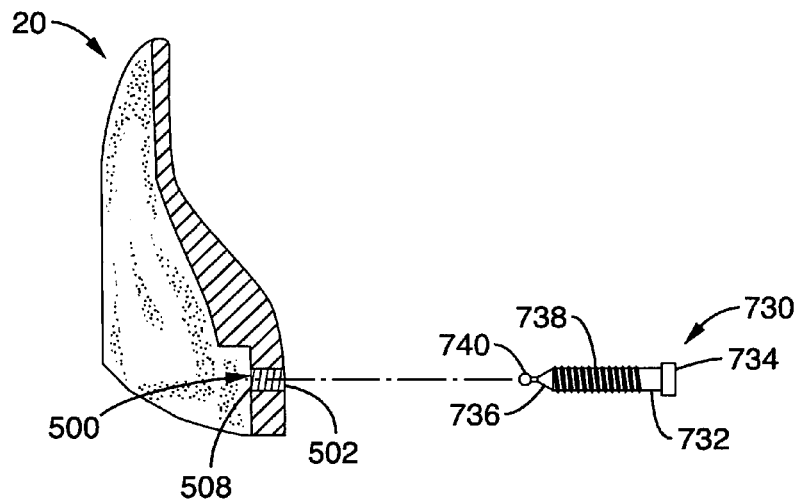
FIG. 59 is a side sectional view through the custom tibial guide illustrated in FIG. 44 and showing threads in the hole in the custom tibial guide, and a side elevational view of the adjustment screw showing corresponding threads on the cylindrical body of the radiographic guide insert device and further illustrating a head, shank, narrow neck and bulbous end or tip of the adjustment screw.

Referring now to FIG. 59, the adjustment screw 730 is comprised of an elongated shank 732 having a drive head 734 at a first end and a narrow neck 736 at a second end. The elongated shank 732 includes exterior threads 738 that extend between an area below the drive head 734 and the narrow neck 736 and that match the threads 508 on the interior surface 502 of the hole 500 disposed in the custom tibial cutting guide 20. In turn, the narrow neck 736 extends away from the threaded elongated shank 732 and transitions into a bulbous end or tip 740.

Figure 60:
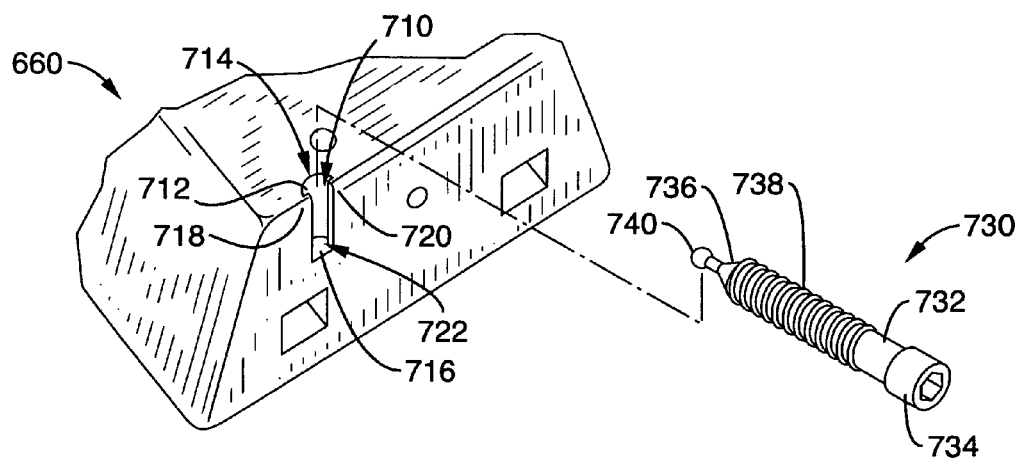
FIG. 60 is a top, front, and side perspective view of the anterior lateral edge of the tibial reaming guide illustrated in, for example, FIG. 57 and further showing the adjustment screw aligning with the vertical groove in the anterior face of the tibial reaming guide, and showing the lateral and central anterior flanges at the edges of the vertical groove.
Figure 61:
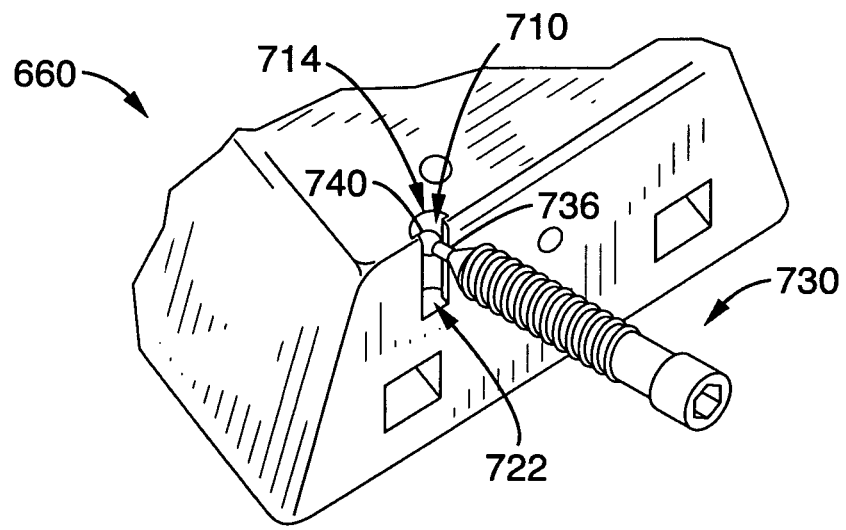
FIG. 61 is a top, front, and side perspective view of the anterior lateral edge of the tibial reaming guide illustrated in, for example, FIG. 57 and further showing the bulbous end or tip of the adjustment screw within the vertical groove in the anterior face of the tibial reaming guide and the neck of the adjustment screw interposed between the lateral and central anterior flanges at the edges of the vertical groove.

Referring to FIGS. 60 and 61, the bulbous end 740 of the adjustment screw 730 is sized to fit into the vertically elongated domed shaped groove 710 by way of the superior arcuate shaped opening 714 while the narrow neck 736 is sized to pass between the respective lateral and central anterior flanges 718, 720 via the anterior rectangular opening 722 thereby allowing the adjustment screw to be inferiorly passed from the superior arcuate shaped opening 714 while the bulbous end is retained within the vertical groove by the flanges 718, 720. In other words, the superior opening 714 of the vertical groove 710 is large enough to allow passage of the bulbous end 740 of the adjustment screw 730 therethrough while the interior of the vertical groove 710 is large enough to contain the bulbous end 740 with the anterior rectangular opening 722 between the lateral and central anterior flanges 718, 720 wide enough to allow the narrow neck 736 of the adjustment screw 730 to pass therethrough but too narrow to allow the bulbous end 740 to pass therefrom such that bulbous end 740 is captured within the vertical groove 710.

Cylinder Inserts for Adjustment Screw when Cylinder Hole is Smooth

Figure 62:
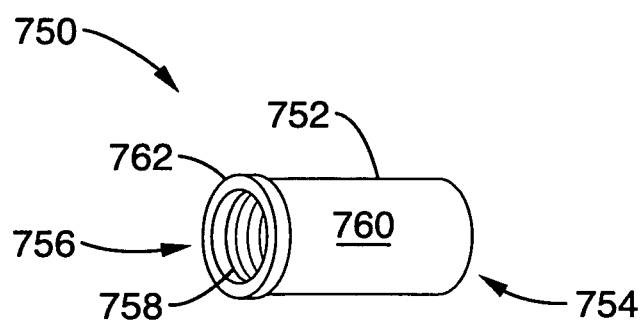
FIGS. 62 and 63 are side elevational views of the outer and inner cylinders, respectively wherein the outer and inner cylinders screw together and wherein the combination is sized to frictionally fit into the smooth hole in the custom tibial guide illustrated in FIGS. 37 and 38 to provide threads for the adjustment screw to engage.
Figure 63:
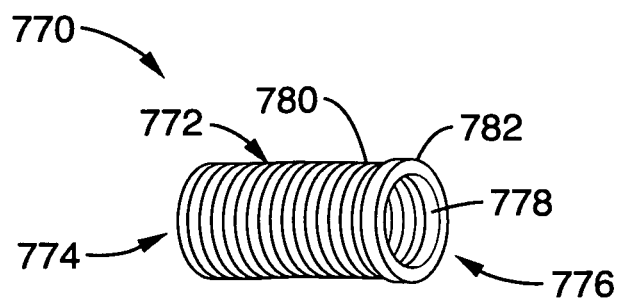
Figure 64:
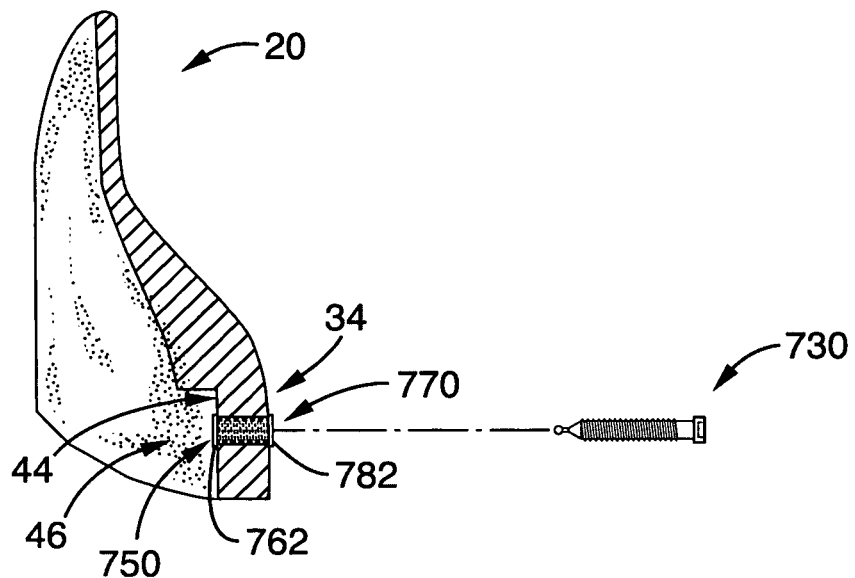
FIG. 64 is a side sectional view of the custom tibial guide illustrated in FIGS. 37 and 38 with the inner and outer cylinders screwed together in place in the hole of the custom tibial guide and a side elevational view of the adjustment screw anteriorly aligned therewith.

Referring to FIGS. 62 through 64, and in another embodiment, the adjustment screw 730 is utilized with an outer cylindrical sleeve 750 and an inner cylindrical sleeve 770 when the cylindrically shaped interior surface 502 of the guide hole 500 comprises a smooth surface.

Outer cylindrical sleeve 750 is comprised of an elongated cylindrical sidewall 752 extending between an open first end 754 and an open second end 756. The elongated cylindrical sidewall 752 includes a cylindrical interior threaded surface 758 extending between the open first and second ends 754, 756 and a cylindrical exterior surface 760 extending between the open first end 754 and an annular rim 762 circumscribing the second open end 756. Additionally, the elongated cylindrical sidewall 752 of the outer cylindrical sleeve 750 has an outer diameter sized to fit snugly into the guide hole 500 in the custom tibial cutting guide 20.

Similar to the outer cylindrical sleeve 750, the inner cylindrical sleeve 770 is comprised of an elongated cylindrical sidewall 772 extending between an open first end 774 and an open second end 776. The elongated cylindrical sidewall 772 includes a cylindrical interior threaded surface 778 extending between the open first and second ends 774, 776 and a cylindrical exterior threaded surface 780 extending between the open first end 774 and an annular rim 782 circumscribing the second open end 776. The cylindrical exterior threaded surface 780 of the inner cylindrical sleeve 770 is complementary to the cylindrical interior threaded surface 758 of the outer cylindrical sleeve 750 for mating with one another. Hence, if the guide hole 500 in the custom tibial guide 20 is smooth, the two interlocking cylinders, inner cylinder 770 and outer cylinder 750, can be screwed together from each side of the hole 500 in the custom tibial guide 20 as illustrated in FIG. 64.

Adjustment of Position of Tibial Reaming Guide 660

In use and operation, and referring to FIGS. 62 through 64, the outer cylindrical sleeve 750 is fitted into the guide hole 500 until the annular rim 762 abuts or seats against the posterior surface portion 44 of the locator notch 46. In turn, the inner cylindrical sleeve 770 is threadedly coupled to the outer cylindrical sleeve 750 by treading the exterior threaded surface 780 of the inner cylindrical sleeve 770 into interior threaded surface 758 of the outer cylindrical sleeve 750 until the annular rim 782 of the inner cylindrical sleeve 770 abuts or seats against the anterior surface 34 of the custom tibial cutting guide 20.

Figure 65:
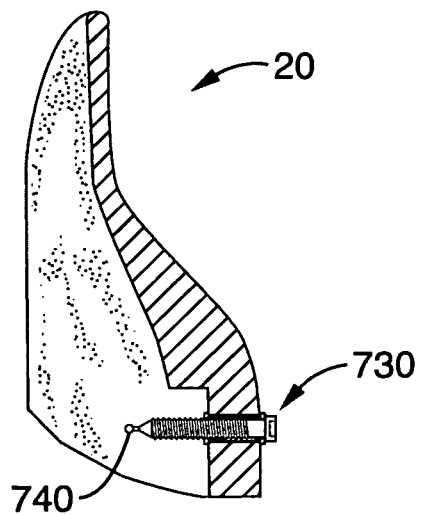
FIG. 65 is a side sectional view of the adjustment screw threadedly coupled through the cylinders disposed in the hole of the custom tibial guide illustrated in FIG. 64 with the bulbous end or tip protruding at the posterior surface.

Then, as shown in FIG. 65, the adjustment screw 730 is threadedly coupled with and screwed through the cylindrical interior threaded surface 778 of the elongated cylindrical sidewall 772 of the inner cylindrical sleeve 770 until the bulbous end 740 of the screw 730 emerges therethrough.

Figure 66:
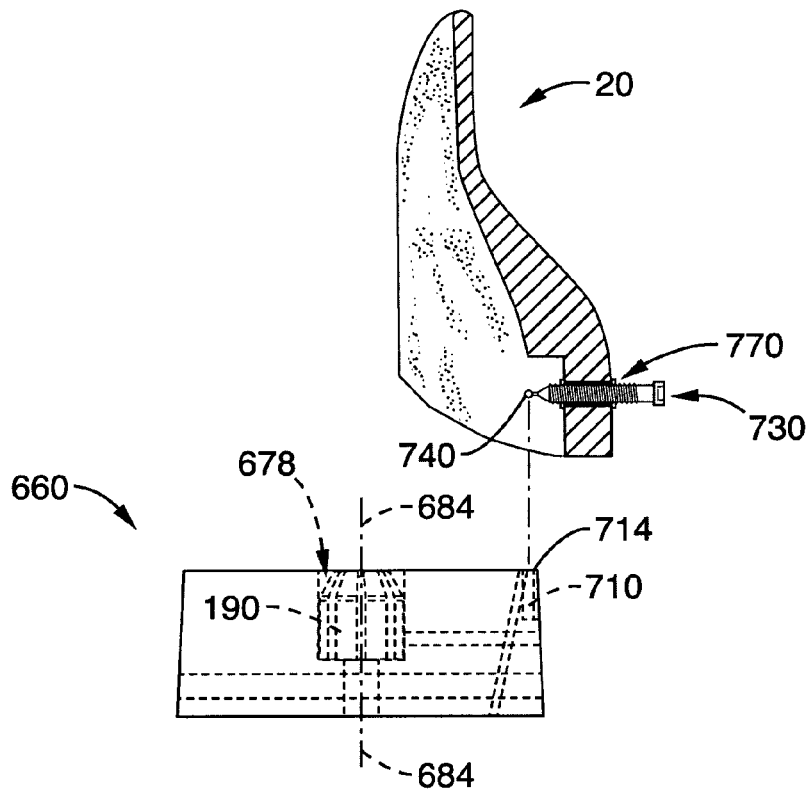
FIG. 66 is a side sectional view of the tibial reaming guide illustrated in, for example, FIG. 48 and positioned just inferior to the custom tibial guide and adjustment screw illustrated in FIG. 65 wherein the bulbous end of the adjustment screw is shown aligned just superior to the superior opening of the vertical groove in the anterior face of the tibial reaming guide.
Figure 67:
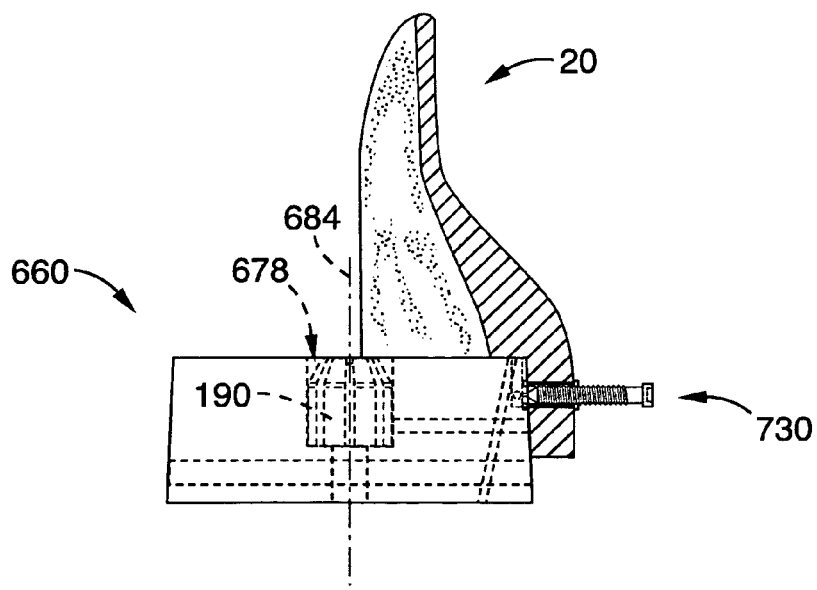
FIG. 67 is a side sectional view of the tibial reaming guide and the custom tibial guide as illustrated in FIG. 66, and further illustrating the coupling of the two by way of the bulbous end of the adjustment screw being disposed within the vertical groove of the anterior face of the tibial reaming guide, and further illustrating the central axis of the central channel of the tibial reaming guide.
Figure 68:
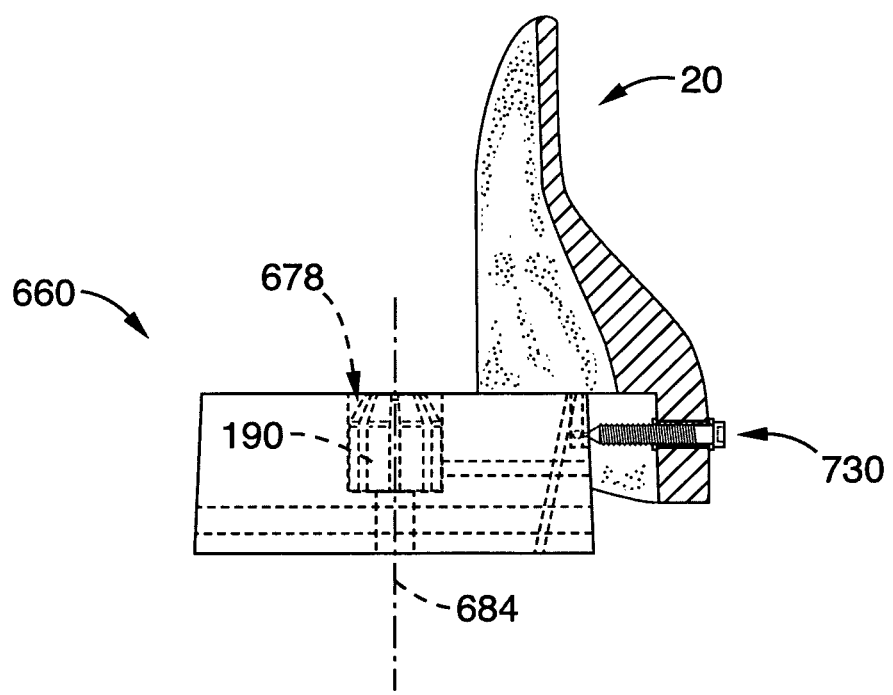
FIG. 68 is a side sectional view of the tibial reaming guide coupled to the custom tibial guide through the adjustment screw as shown in FIG. 67, and further illustrating the adjustment screw mechanism having displaced the tibial reaming guide posteriorly, and further illustrating the displacement of the central axis of the central channel of the tibial reaming guide.

Next, and referring to FIGS. 66 through 68, the bulbous end 740 is first aligned with the superior arcuate shaped opening 714 (FIG. 60) and then fitted into the vertically elongated domed shaped groove 710 of the custom tibial reaming guide 660 for allowing posterior adjustment of the custom tibial reaming guide 660 by turning the adjustment screw 730 within the inner cylindrical sleeve 770 (FIG. 63).

Figure 69:
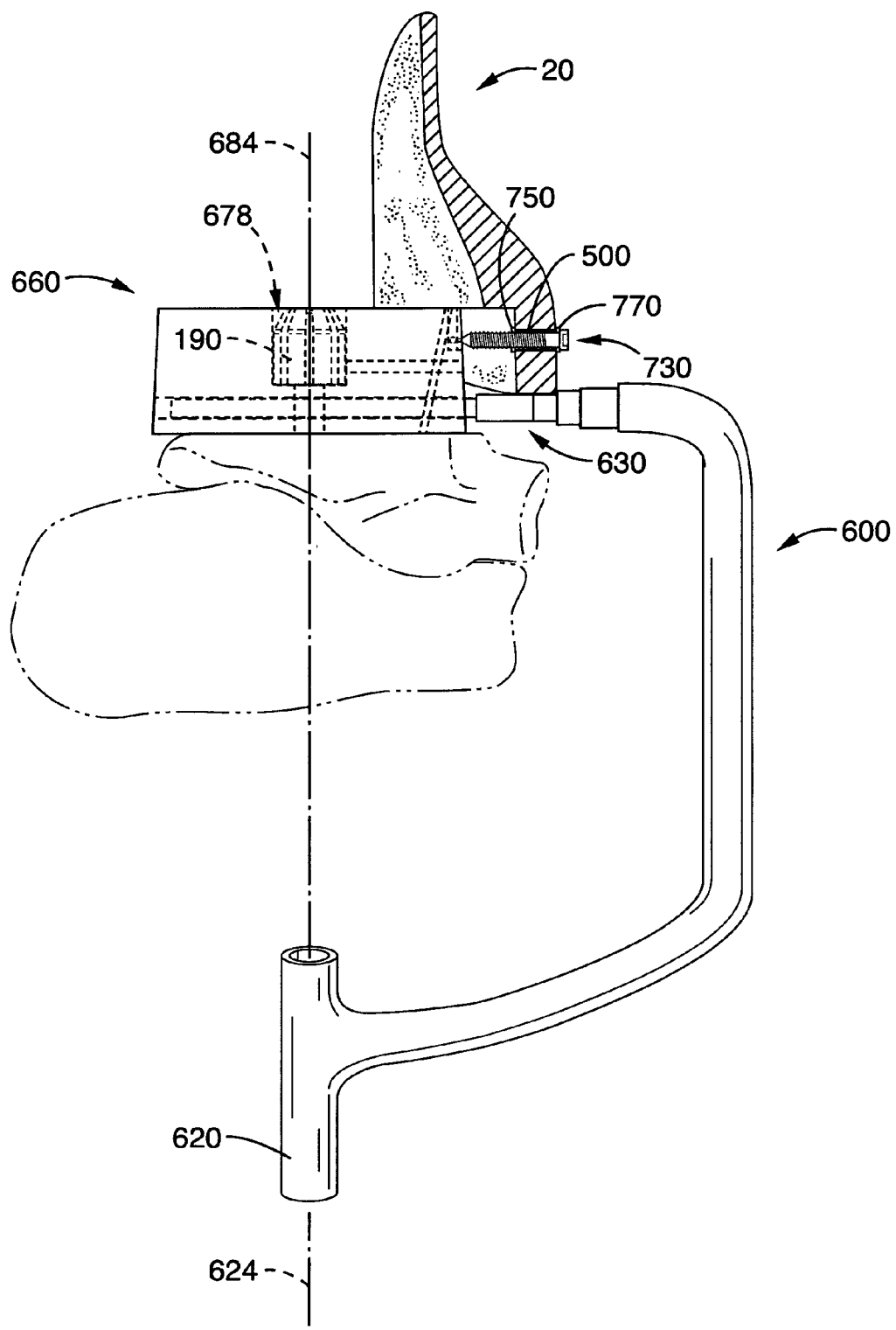
FIG. 69 is a side view of the tibial reaming guide and adjustment screw illustrated in FIG. 68 with the tibial reaming bit held in the central channel with the fixation pin, and further illustrating a side elevational view of the C-shaped outrigger guide illustrated in, for example, FIG. 45, coupled to the tibial reaming guide through the tuning fork shaped adaptor, and further illustrating the alignment of the central axis of the central channel of the tibial reaming guide with the axis of the distal sleeve of the C-shaped outrigger.

Accordingly, the posterior position of tibial reaming can be adjusted intraoperatively if the surgeon determines that the alignment provided by the custom tibial reaming guide 660 is not proper. In particular, the axis 684 of the central channel 678, with the tibial reaming bit 190 inside, can be posteriorly adjusted intraoperatively to a different position such as from a first position illustrated in FIG. 67 to a second a different position posterior as illustrated in FIGS. 68 and 69. The tibial reaming guide 660 cannot be brought more anterior, because it will impinge against the custom tibial guide 20. To correct the position of reaming anteriorly, a custom anteriorly truncated tibial reaming guide 860 and a reversible tibial reaming guide 960 are provided and delineated in detail below.

Referring to FIG. 69, it is preferred that during these maneuvers the alignment of the distal sleeve 620 of the C-shaped outrigger alignment guide 600 with the reamer bit 190 in the tibial reaming guide 660 remains constant. In other words, the central axis 684 of a tibial reaming guide 660 and the center of the tibial reaming bit 190 remains aligned with a central axis 624 of the distal sleeve 620 of the C-shaped outrigger alignment guide 600 when it is attached through the tuning fork shaped adapter 630, even when the tibial reaming guide 660 is pushed posteriorly via the threaded adjustment provided by the adjustment screw 730 threadedly coupling with the inner cylindrical sleeve 770 which, in turn, is threadedly coupled with the outer cylindrical sleeve 750 fitted within the guide hole 500 disposed in the custom tibial cutting guide 20.

Lateral Radiographic Marker and Alignment Guide

When adjusting the position of a tibial reaming guide anteriorly or posteriorly, it is preferred to have a marker on the guide that will indicate the position of the central axis of the central channel, so that can be aligned by the surgeon against known bone landmarks with intra-operative fluoroscopy.

Figure 70:
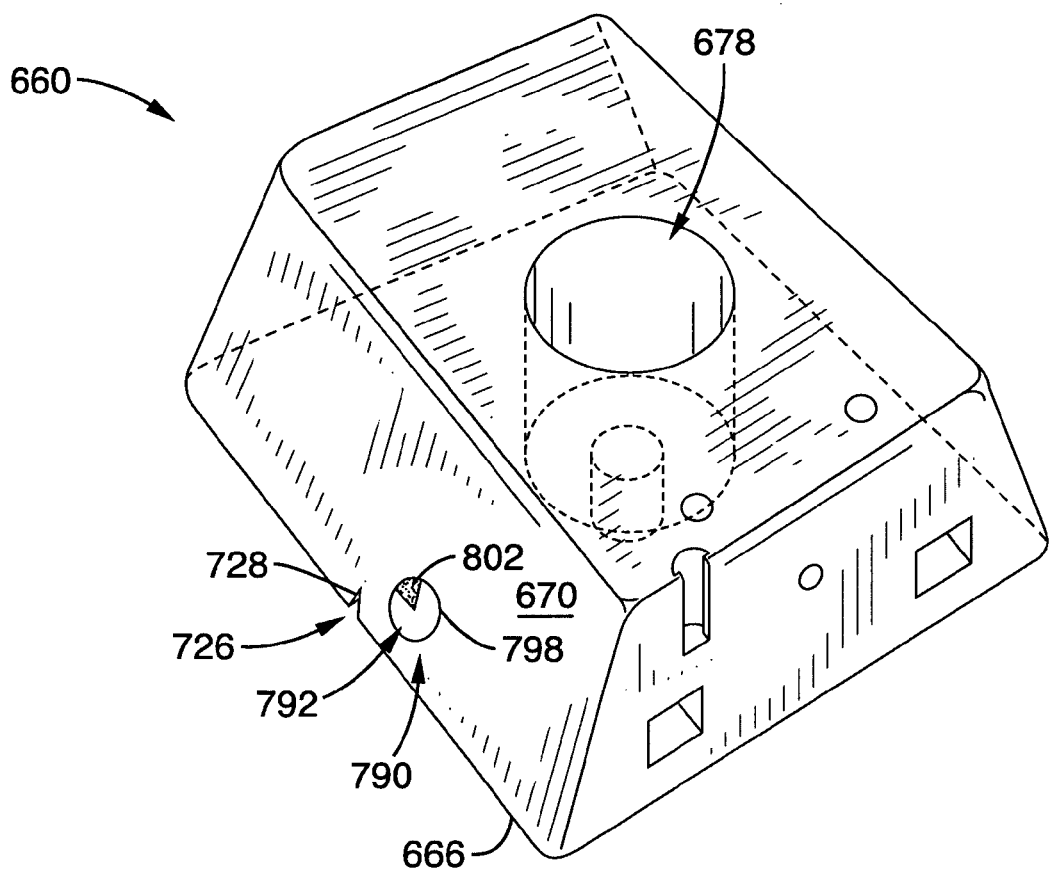
FIG. 70 is a top, front, and side perspective view of the tibial reaming guide illustrated in, for example, FIG. 48 and further including a notch in the lateral and inferior surfaces, and a lateral radiographic alignment marker cylinder hole with a radiodense quadrant in the outer surface.
Figure 71:
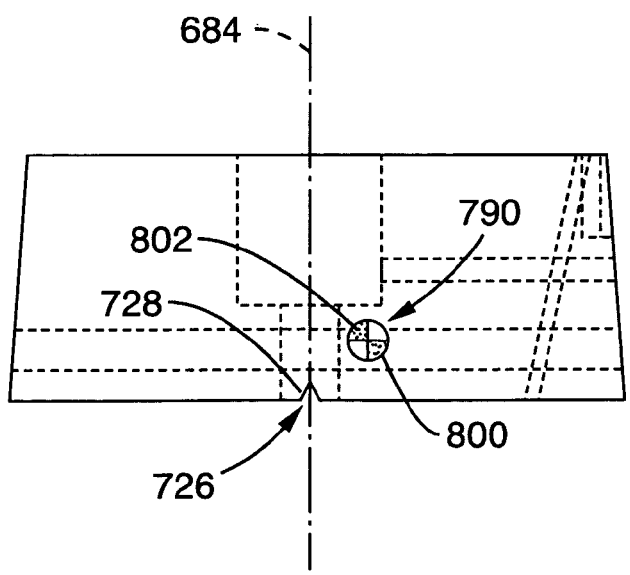
FIG. 71 is a side elevational view of the embodiment of the tibial reaming guide illustrated in FIG. 70 and illustrating the notch in the inferior surface and with the lateral radiographic alignment marker cylinder hole with the radiodense markers on the inner and outer surfaces.
Figure 72:
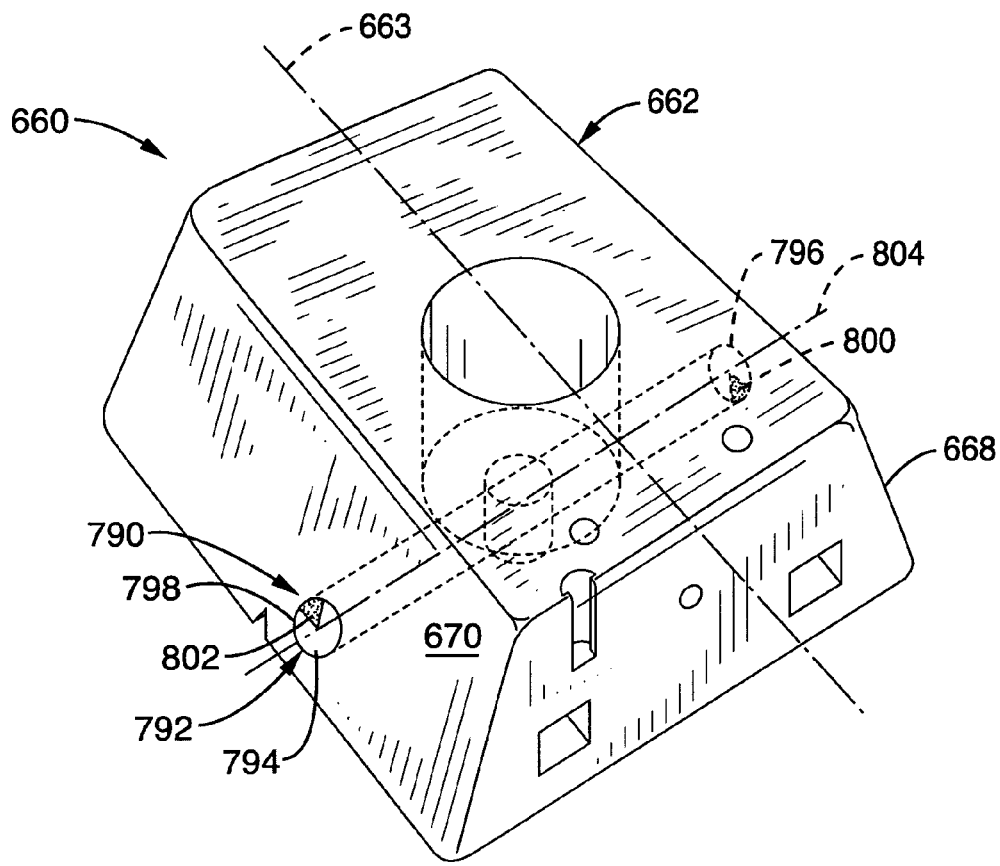
FIG. 72 is a top, front, and side perspective view of the tibial reaming guide illustrated in FIGS. 70 and 71 with the lateral radiographic alignment marker cylinder hole shown in phantom lines and with the radiodense markers on the inner and outer surfaces in the form of a radiodense quadrant on the inner surface and a radiodense quadrant on the outer surface.

As shown in FIGS. 70 and 71, an embodiment of the custom tibial reaming guide 660 comprises a lateral radiographic marker in the form of, for example, a notch or groove 726 disposed in the inferior face 666 of the tibial reaming guide 660 with a cleft 728 in the outer face 670 and one in the inner face 668 that can be identified with an intra-operative fluoroscopy to identify the position of the axis 684 of the central channel 678 of the tibial reaming guide 660, so the surgeon can verify that it is properly aligned with the radiographic appearance of the distal tibia in the proper position for reaming.

As shown in FIGS. 70 through 73, and in another embodiment, the custom tibial reaming guide 660 comprises a lateral radiographic alignment guide 790. In one embodiment, and referring to FIG. 72, the lateral radiographic alignment guide 790 is comprised of a cylindrical radiographic alignment guide hole 792 defined by an elongated cylindrical interior surface 794. The cylindrical hole 792 passes through the reamer body 662 of the tibial reaming guide 660 with the longitudinal axis 804 perpendicular to a long axis 663 (FIG. 48) of the tibial reaming guide and includes an inner face opening 796 in the inner face 668 the tibial reaming guide 660 and an outer face opening 798 in the outer face 670 of the tibial reaming guide 660. The lateral radiographic alignment guide 790 is further comprised of a first flange or other radiodense marker 800 at the inner face opening 796 and a second flange or other radiodense marker 802 at the outer face opening 798. When viewed with fluoroscopy, with the fluoroscopy beam aligned with a longitudinal axis 804 of the cylindrical hole 792, the two radiodense markers 800, 802 will appear to align with a regular pattern as illustrated in FIG. 71. In other words, when a true lateral alignment of the fluoroscopy beam is obtained, as shown in FIG. 71, the radiographic appearance will be of the radiodense quadrants 800, 802 aligned as a cross.

Figure 43:
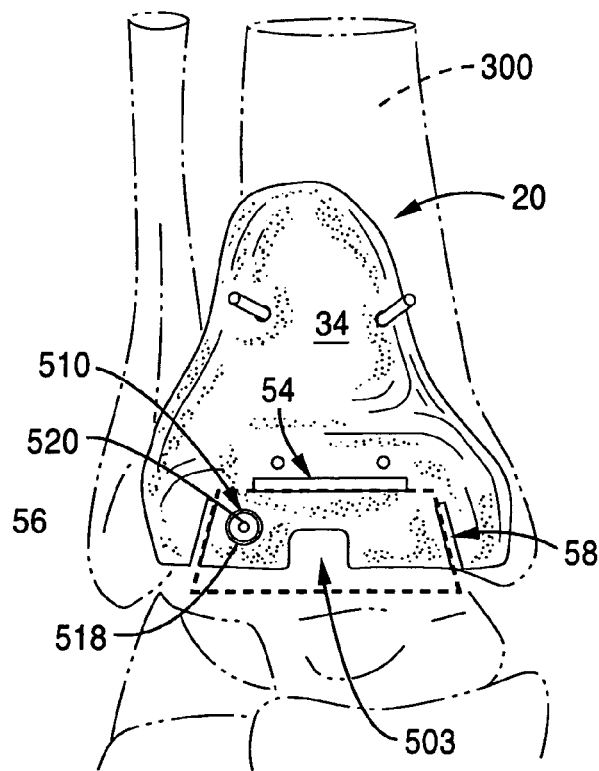
FIG. 43 is a front elevational view of the custom tibial cutting guide illustrated in, for example, FIG. 37 and shown fit in place against the anterior surface of the distal portion of the tibia, removeably secured thereto, with the radiographic insert guide device in place demonstrating the alignment of the guide coaxial with the view of the illustration.
Figure 73:
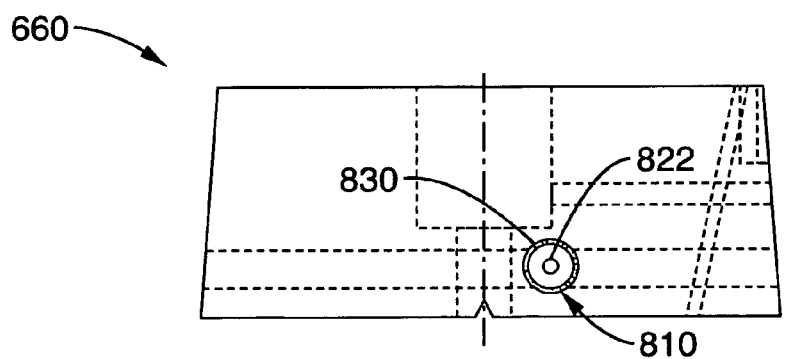
FIG. 73 is a side elevational view of the embodiment of the tibial reaming guide illustrated in, for example, FIG. 48 with a lateral radiographic alignment guide insert disposed in a cylindrical radiographic alignment guide hole and a notch in the lateral and inferior surfaces of the tibial reaming guide.
Figure 74:
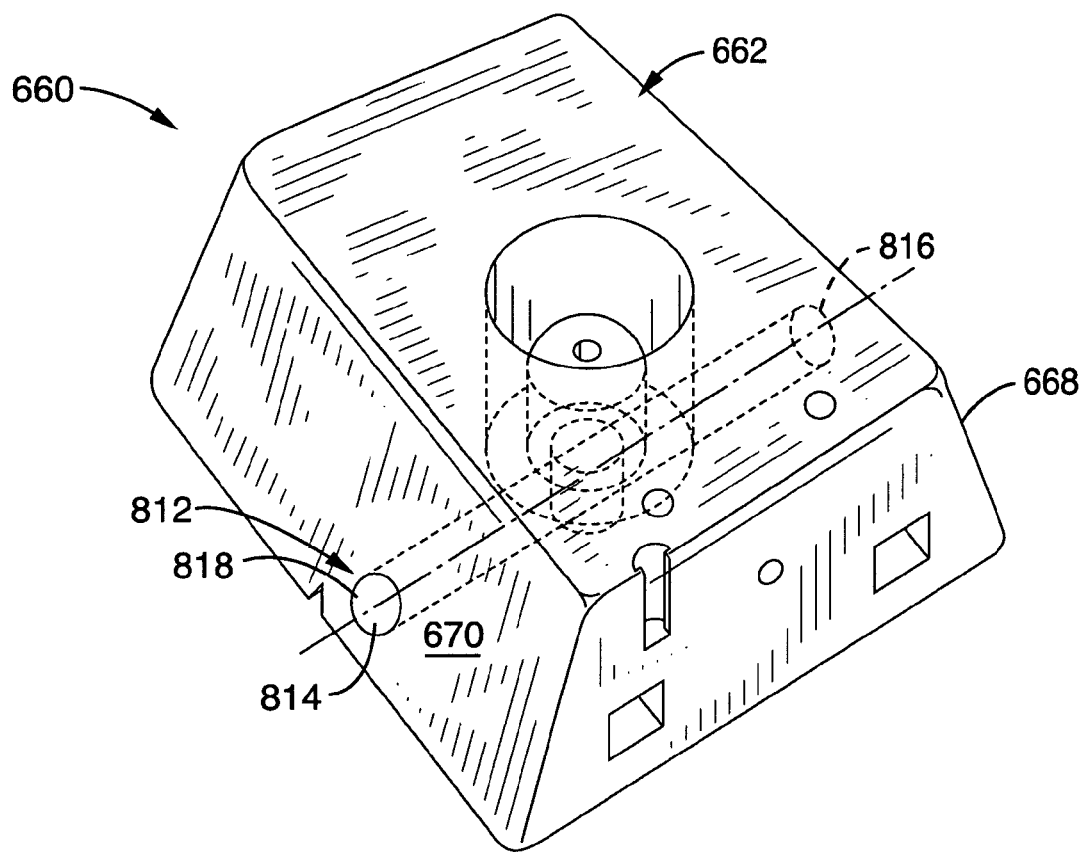
FIG. 74 is a top, front, and side perspective view of the tibial reaming guide illustrated in FIG. 73 with the cylindrical radiographic alignment guide hole shown in phantom lines.
Figure 75:
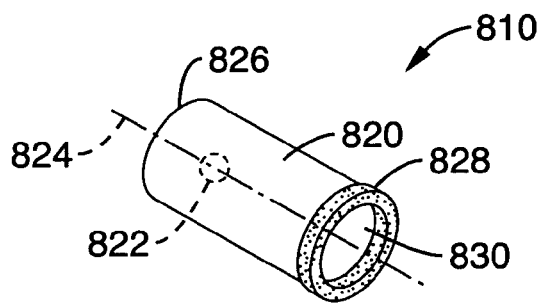
FIGS. 75 and 76 respectively illustrate a perspective view and a side elevational view of the lateral radiographic insert showing the radiodense sphere embedded in the radiolucent cylinder with the sphere close to one end, and having its center lie along the longitudinal axis of the cylinder.
Figure 76:
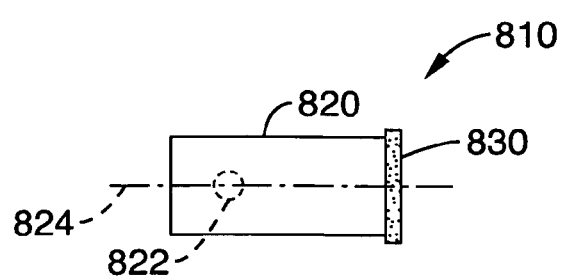

In another embodiment, and referring to FIGS. 73 through 76, the custom tibial reaming guide 660 comprises a lateral radiographic alignment guide 810 which, in one embodiment, is removable from a cylindrical radiographic alignment guide hole 812 defined by an elongated cylindrical interior surface 814. Analogous to the cylindrical radiographic alignment guide hole 792, the cylindrical radiographic alignment guide hole 812 passes through the reamer body 662 of the tibial reaming guide 660 and includes an inner face opening 816 in the inner face 668 of the tibial reaming guide 660 and an outer face opening 818 in the outer face 670 of the tibial reaming guide 660. The lateral radiographic alignment guide 810 is comprised of a translucent cylinder 820 sized to be closely and removeably received within the cylindrical radiographic alignment guide hole 812. The translucent cylinder 820 includes a marker in the form of, for example, a sphere 822 centered on a longitudinal axis 824 of the translucent cylinder 820 at a location closer to one end or a rear end 826 of the translucent cylinder 820 than the other end or front end 828. The sphere 822 will appear centered within a circular rim 830 circumscribing the front end 828 of the translucent cylinder 820 when a fluoroscopy beam emanates from in front of the front end 828 and is aligned with the longitudinal axis 824 of the cylinder 820 as illustrated in FIG. 73, similar to the pattern shown with the alignment of the radiographic beam with the longitudinal axis 516 of the radiographic insert 510 used with the custom tibial guide 20 as shown in FIG. 43. In other words, when a true lateral alignment of the fluoroscopy beam is obtained, as shown in FIG. 73, the radiographic appearance will be of a radiodense sphere 822 centered within a circle formed by the circular rim 830.

Anteriorly Truncated Tibial Reaming Guide 860

Figure 77:
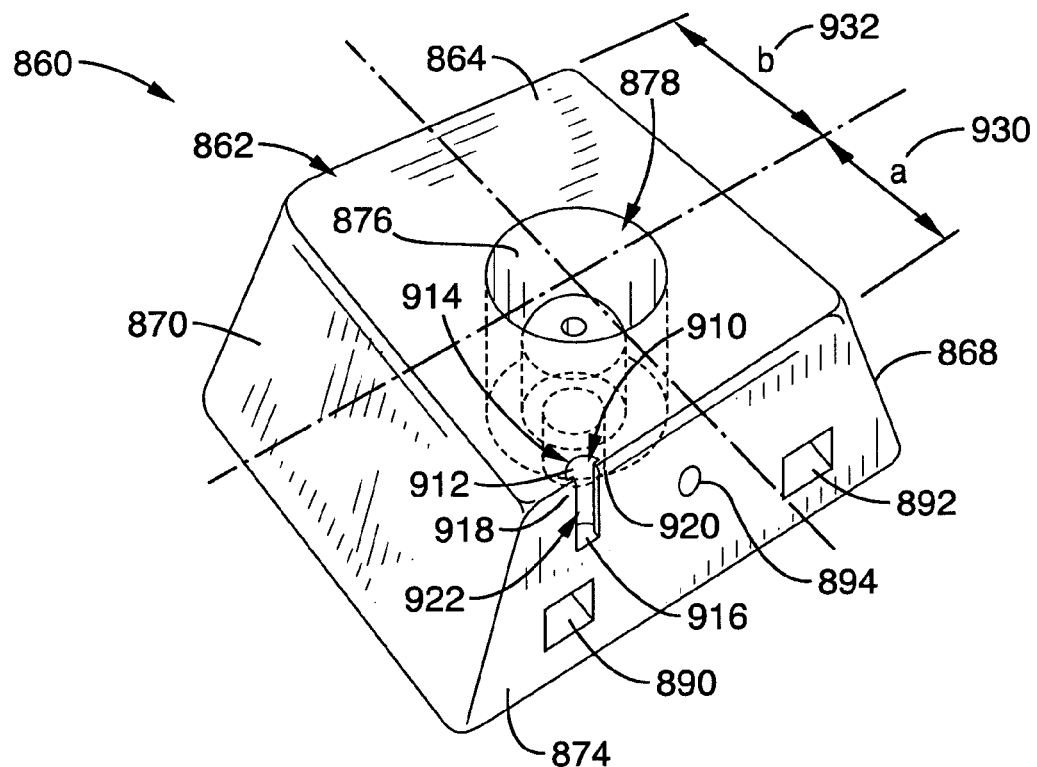
FIG. 77 is a top, front, and side perspective view of a truncated tibial reaming guide, with a general shape congruent with the tibial reaming guide shown in FIG. 45, with at least one exception that the anterior body is shortened so that the center of the central body channel is offset anteriorly, and further showing the long axis of the body and a perpendicular axis to this through the diameter of the central channel.
Figure 78:
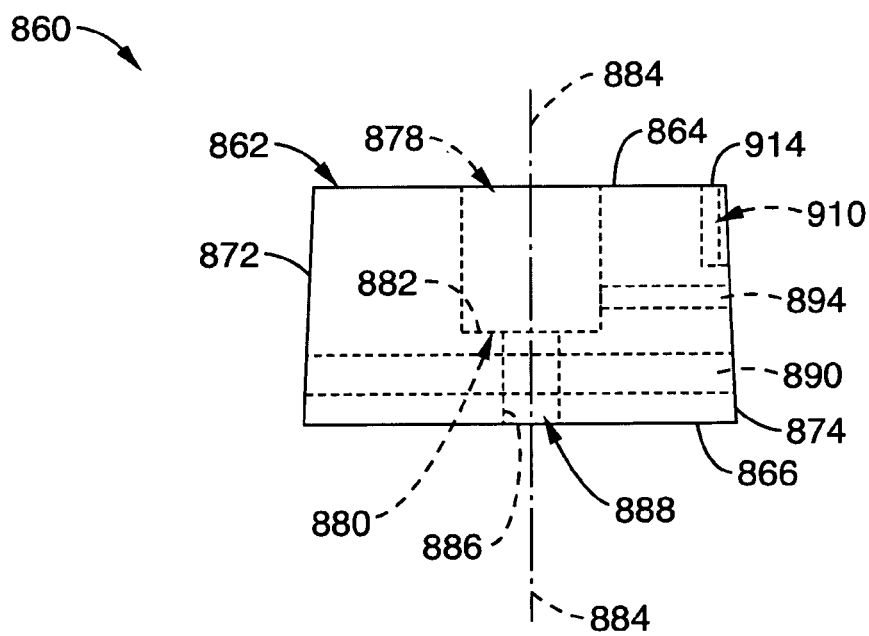
FIG. 78 is a side sectional view of the truncated tibial reaming guide showing in phantom lines the channels that pass through the anterior face in the inferior half of the body for attachment of the tuning fork shaped adaptor, the channel extending from the anterior face to the central channel for passage of the fixation pint, and a vertical channel in the superior anterior face for attachment of the adjustment screw.

Referring to FIGS. 77 and 78, and in another embodiment, the tibial reaming guide is in a form of a custom anteriorly truncated tibial reaming guide 860 comprising an anteriorly truncated reamer body 862. The shape of the truncated reamer body 862 is otherwise congruent with the bodies 162 and 662 of the respective tibial reaming guides 160 and 660 and generally follows the same manufacturing protocol for providing a range of sizes that correspond to the different selection of prosthesis sizes 362.

In particular, and still referring to FIGS. 77 and 78, the anteriorly truncated tibial reaming guide 860 is comprised of the anteriorly truncated reamer body 862 having a generally pyramidal frustum shape that is designed to fit into the tibial-talar space 342 defined as the space between the tibia 300 and the talus 330 after the resected tibial and talar bone segments have been removed. Accordingly, the truncated reamer body 862 corresponds to the size of the chosen prosthesis 370 to be used, so if there are five different prosthesis sizes to choose from then there are five different tibial reaming guide sizes for providing a one to one correspondence between the two.

Additionally, the truncated reamer body 862 is comprised of six faces: a superior face 864, an inferior face 866, an inner face 868, an outer face 870, a posterior face 872, and an anterior face 874. The superior and inferior faces 864 and 866 have a generally square or rectangular shape while the inner face 868, outer face 870, posterior face 872, and anterior face 874 have a generally trapezoidal shape.

Furthermore, the reamer body 862 of the tibial reaming guide 860 is comprised of a first interior cylindrical surface 876 that has a first inside circumference that defines a first cylindrically shaped central channel 878 that extends from an opening in the superior face 864 to an annular stepped shoulder 880 disposed substantially parallel to the superior face 864. The annular stepped shoulder 880 forms an axially directed stop surface 882. A central longitudinal axis 884 of the first cylindrically shaped central channel 878 is substantially perpendicular to both the superior face 864 and the annular stepped shoulder 880. The open ended cylindrically shaped central channel 878 is sized to receive the cannulated reaming bit 190 (FIGS. 11 and 12) comprised of the axial passage 192 extending through the interior of the cannulated reaming bit 190 and a bone reaming exterior surface comprised of front cutting threads 194 and side cutting threads 196.

Moreover, a second interior surface 886 has a second inside circumference less than the first inside circumference of the first interior cylindrical surface 876 and defines a second central channel 888 that extends from an opening in the annular stepped shoulder 880 to an opening in the inferior face 866. Accordingly, the first cylindrically shaped central channel 878 and the second central channel 888 are in open communication with one another and in open communication between the openings in the superior face 864 and the inferior face 866. Additionally, the central longitudinal axis 884 of the first cylindrically shaped central channel 878 is also the central longitudinal axis of the second central channel 888. Furthermore, and in one embodiment, the second central channel 888 comprises a cylindrically shaped second interior surface 886 or a conically shaped second interior surface 886 with an inferior end having a wider diameter and tapering to a narrower diameter at the level of the annular stepped shoulder 880, with the conical shape guiding the reamer driver 416 to the opening at the annular stepped shoulder 880 having a diameter large enough to allow passage therethrough.

Accordingly, the anteriorly truncated reamer body 862 of the tibial reaming guide 860 is defined by having a distance (930 or a) from the superior edge of the anterior face 874 to the center of the central channel 878 shorter than the distance (932 or b) from the superior edge of the posterior face 872 to the center of the central channel 878 as illustrated in FIG. 77.

In one situation, the central longitudinal axis 884 aligns or is coincident with the central axis 302 of the tibia 300 when the trapezoidally shaped anterior face 874 of the reamer body 862 abuts against the trapezoidally shaped posterior surface portion 44 of the reaming guide locator notch 46 and when the custom tibial cutting guide 20 is placed against the anterior surface portion 306 of the distal portion 304 of the tibia 300 with a portion of the reamer body 862 received within the tibial-talar space 342. Thus, when the cannulated reaming bit 190 is received within the first cylindrically shaped central channel 878, the shape of the custom tibial cutting guide 20 and the depth of the locator notch 46 in its distal end combine to set the alignment of the axial passage 192 of the cannulated reaming bit 190 with the central axis 302 of the tibia 300 for reaming of the tibia 300 along its central axis 302 with the reaming exterior front and side cutting threads 194, 196 of the cannulated reaming bit 190. The diameter of the first cylindrically shaped central channel 878 of the reamer body 862 is sized to closely receive the cannulated reamer bit 190 and the annular stepped shoulder 880 forms the axially directed stop surface 882 for supporting the cannulated reamer bit 190. The cannulated reamer bit 190 is of the size needed to ream the tibial blind bore 328 for the size of the tibial stem or, in one embodiment, the modular tibial stem components 372 of the size of the preoperatively chosen prosthesis 370.

Attachment Channels 890, 892

Still referring to FIGS. 77 and 78, and analogous to reamer body 662, the reamer body 862 of the custom tibial reaming guide 860 is comprised of two attachment channels 890, 892 for respectively receiving the spaced apart furcations or tines 638, 640 of the forked end portion 636 of the tuning forked shaped adapter 630 illustrated in FIG. 36. The two attachment channels 890, 892 pass from the anterior surface 874 of the custom tibial reaming guide 860, and pass through the inferior half of the body 862 of the tibial reaming guide 860, and may pass through the entire body, but at least to a depth to accommodate the length of the tines 638, 640 on the tuning forked shaped adapter 630 of the length corresponding to that tibial reaming guide, and with a width of separation between the channels 890, 892 corresponding to the width of separation between the tines 638, 640 on the corresponding tuning fork adapter 630.

Also analogous to reamer body 662, the reamer body 862 of the custom tibial reaming guide 860 also comprises a fixation pin hole or channel 894 that passes from the anterior surface 874 of the tibial reaming guide 860 into the central channel 878 with a diameter large enough to allow passage of the fixation pin 696. The fixation pin 696 engages the tibial reaming bit 190 when it sits on the ledge 882 in the central channel 878 of the tibial reaming guide 860. This engagement stabilizes the tibial reaming bit 190 within the central channel 878. Accordingly, the use and operation of the fixation pin 696 with the tibial reaming bit 190 when placed within the central channel 878 is analogous to that which has been delineated above with respect to the use and operation of the fixation pin 696 with the tibial reaming bit 190 when placed within the central channel 678.

Furthermore, and analogous to reamer body 662, the reamer body 862 of the custom tibial reaming guide 860 can also employ stabilization pins 704 as delineated above with respect to reamer body 662.

Vertical Groove 910

Moreover, and analogous to reamer body 662, the reamer body 862 of the custom tibial reaming guide 860 comprises a vertically elongated groove 910 in the anterior face 874 of the tibial reaming guide 860. The vertically elongated groove 910 comprises a vertically extending domed shaped interior sidewall surface 912 vertically extending between a superior arcuate shaped opening 914 in the superior face 864 to an interior arcuate shaped closed end 916. The vertically extending domed shaped interior sidewall surface 912 transitions into a vertically extending base comprised of a lateral anterior flange 918 and a central anterior flange 920 extending toward, but spaced from one another for defining an anterior rectangular opening 922 extending between the superior arcuate shaped opening 914 and the interior arcuate shaped closed end 916. The lateral anterior flange 918 and the central anterior flange 920 make the anterior rectangular opening 922 of the vertically elongated groove 910 narrower than the interior depths or, in other words, narrower than the interior diameter of the vertically extending domed shaped interior sidewall surface 912 at the base location. The function of this narrowing is as described above following the above detailed description of the adjustment screw 730.

Anteriorly Truncated Tibial Reaming Guide Adjustment

Figure 79:
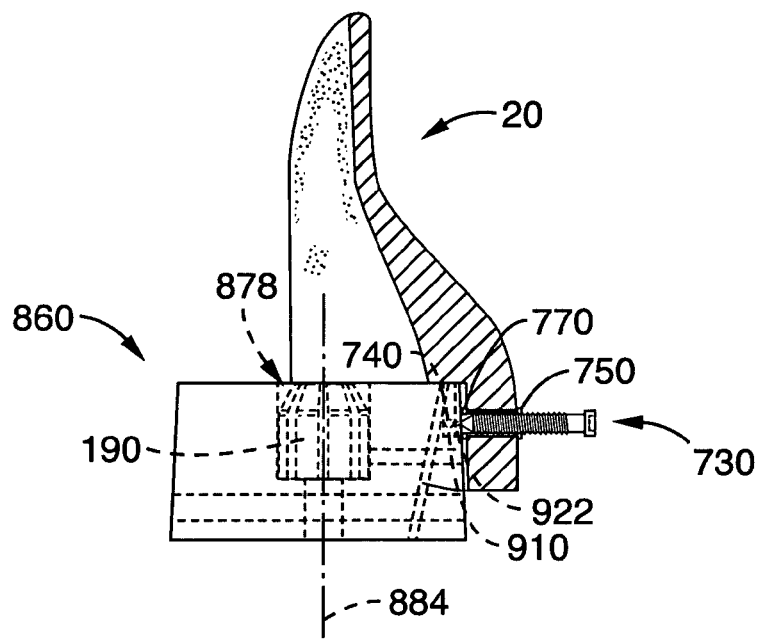
FIG. 79 is a side elevational view of the truncated tibial reaming guide coupled to the adjustment screw and abutting the posterior locator notch of the custom tibial guide illustrated in, for example, FIGS. 37 and 38.
Figure 80:
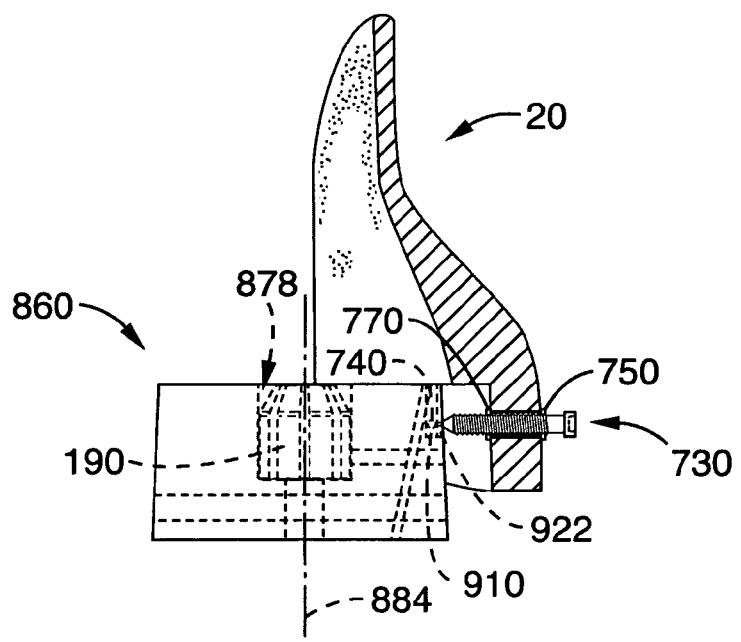
FIG. 80 is a side elevational view of the truncated tibial reaming guide coupled to the adjustment screw and posteriorly adjusted relative to the custom tibial guide illustrated in, for example, FIGS. 37 and 38.
Figure 81:
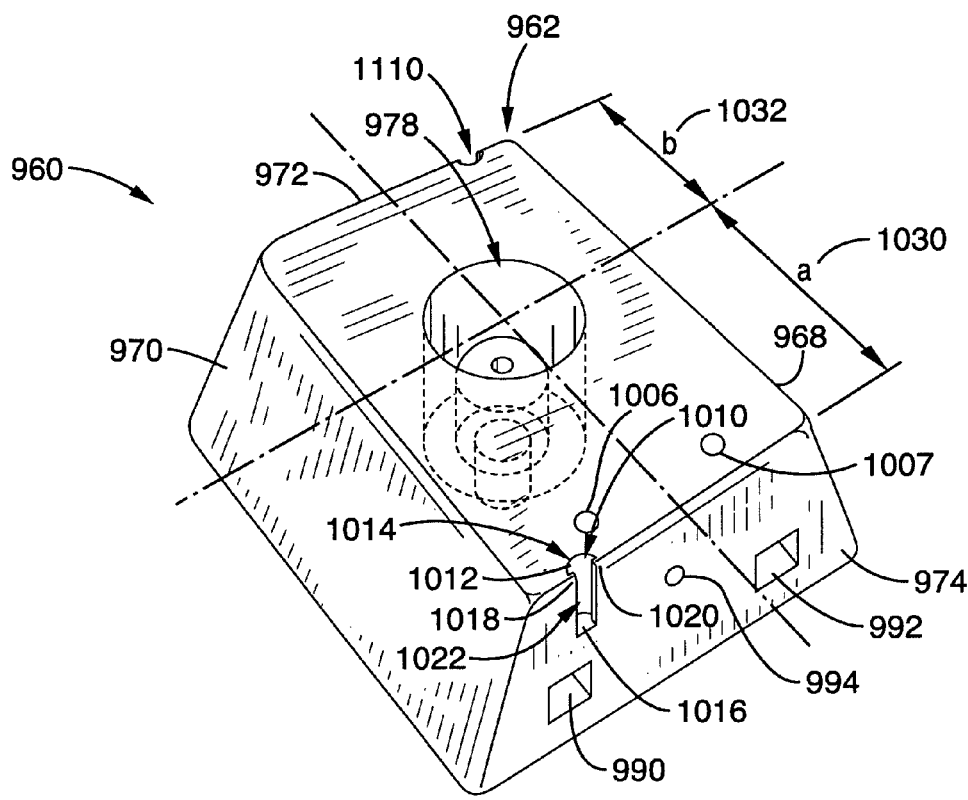
FIG. 81 is a top, front, and side perspective view of a reversible tibial reaming guide having a central body channel circumscribing the removable, cannulated bit with the center of this channel offset posteriorly in a first orientation and anteriorly in a second orientation.
Figure 82:
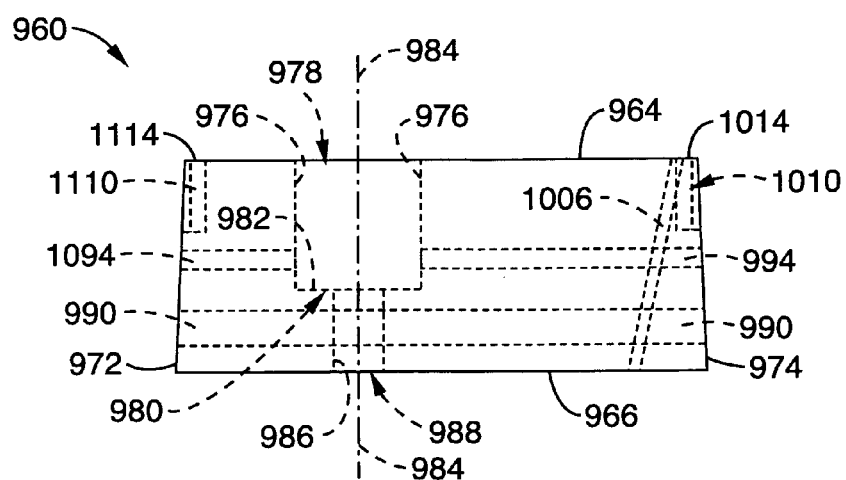
FIG. 82 is a side elevational view of the reversible tibial reaming guide with phantom lines illustrating channels for the fixation pin extending from the anterior surface of the body into the central channel, and from the posterior surface of the body into the central channel, and further illustrating in phantom lines channels in the inferior body for anterior or posterior attachment of the tuning fork adapter, oblique channels running from superior to inferior surfaces for anterior attachment to the custom tibial guide, and vertical grooves in the anterior and posterior faces for attachment of the adjustment screw.
Figure 83:
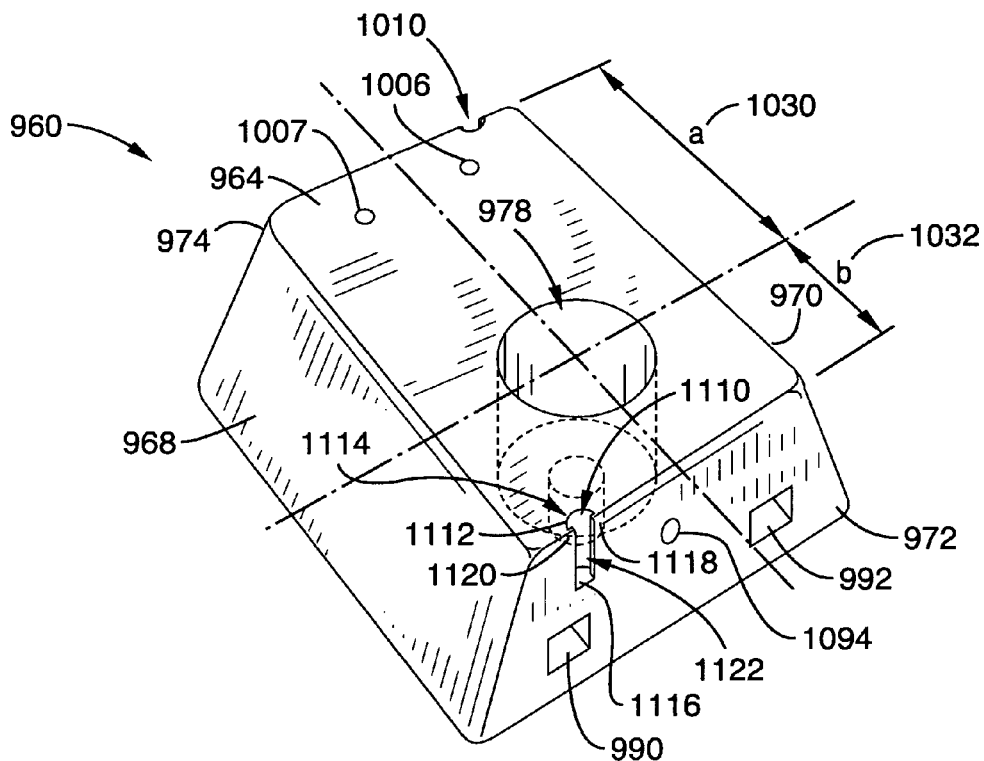
FIG. 83 is a top, back, and side perspective of the reversible tibial reaming guide illustrated in a position reversed or rotated one-hundred-eighty degrees from that which is illustrated in FIG. 81.
Figure 84:
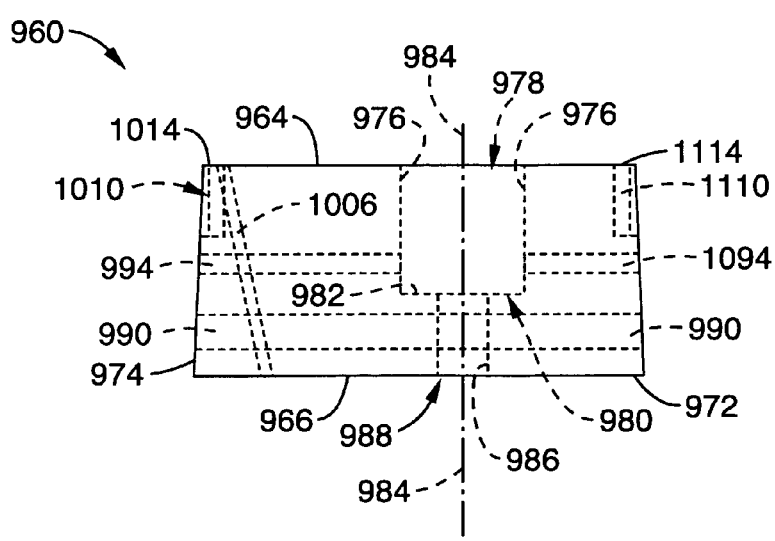
FIG. 84 is a side elevational view of the reversible tibial reaming guide illustrated in a position reversed or rotated one-hundred-eighty degrees from that which is illustrated in FIG. 82.

In use and operation, and to intraoperatively correct the position of reaming anteriorly, the custom anteriorly truncated tibial reaming guide 860 with the anteriorly truncated reamer body 862 can be used as illustrated in FIGS. 79 and 80. As illustrated, the adjustment screw 730 is threadedly coupled with and screwed through the cylindrical interior threaded surface 778 of the elongated cylindrical sidewall 772 of the inner cylindrical sleeve 770 until the bulbous end 740 of the screw 730 emerges therethrough. The bulbous end 740 is then placed down from a superior position into groove 910 for placement as shown in FIG. 79 with the axis 884 of the central channel 878 with the enclosed tibial reaming bit 190 located more anteriorly then when using tibial reaming guide 660.

Now, as shown in FIG. 80, the adjustment screw 730 is turned and the anteriorly truncated reamer body 862 of the custom anteriorly truncated tibial reaming guide 860 is pushed posterior thereby repositioning the anterior position of the axis 884 of the central channel 878 posteriorly, but still anterior to the axis 684 defined by tibial reaming guide 660 interacting with the custom tibial guide 20. This allows for anterior correction over a significant range.

Also analogous to the custom tibial reaming guide 660, the custom anteriorly truncated tibial reaming guide 860 can be provided with a lateral radiographic marker in the form of, for example, a notch or groove disposed in the inferior face 866 of the tibial reaming guide 860 with a cleft in the outer face 870 and one in the inner face 868 that can be identified with an intra-operative fluoroscopy to identify the position of the axis 884 of the central channel 878 of the tibial reaming guide 860, so the surgeon can verify that it is properly aligned with the radiographic appearance of the distal tibia in the proper position for reaming. Additionally, the anteriorly truncated body can be provided with, in one embodiment, the lateral radiographic alignment guide 790 or, in another embodiment, the lateral radiographic alignment guide 810.

Reversible Tibial Reaming Guide 960

Referring to FIGS. 85 through 91, and in another embodiment, the tibial reaming guide is in a form of a custom reversible tibial reaming guide 960 comprising a body shape congruent to tibial reaming guides 660 and 860. Tibial reaming guide 960 generally follows the same manufacturing protocol as the tibial reaming guides 660 and 860 for providing a range of sizes that correspond to the different selection of prosthesis sizes 362.

In particular, the custom tibial reaming guide 960 is comprised of a generally pyramidal frustum shaped reversible tibial reamer body 962 that is designed to fit into the tibial-talar space 342 defined as the space between the tibia 300 and the talus 330 after the resected tibial and talar bone segments have been removed. Accordingly, the reversible tibial reamer body 962 corresponds to the size of the chosen prosthesis 370 to be used, so if there are five different prosthesis sizes to choose from then there are five different sizes of the reversible tibial reaming guide 960 for providing a one to one correspondence between the two.

Additionally, the generally pyramidal frustum shaped reversible tibial reamer body 962 is comprised of six faces: a superior face 964, an inferior face 966, an inner face 968, an outer face 970, a posterior face 972, and an anterior face 974. The superior and inferior faces 964 and 966 have a generally square or rectangular shape while the inner face 968, outer face 970, posterior face 972, and anterior face 974 have a generally trapezoidal shape.

Figure 85:
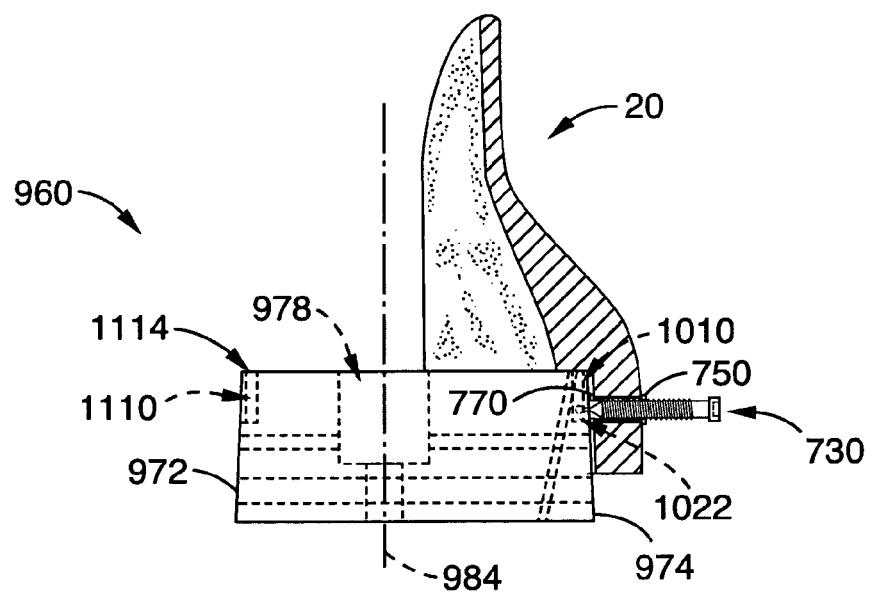
FIG. 85 is a side elevational view of the reversible tibial reaming guide coupled to the adjustment screw in a first orientation and abutting the posterior locator notch of the custom tibial guide illustrated in, for example, FIGS. 37 and 38.
Figure 86:
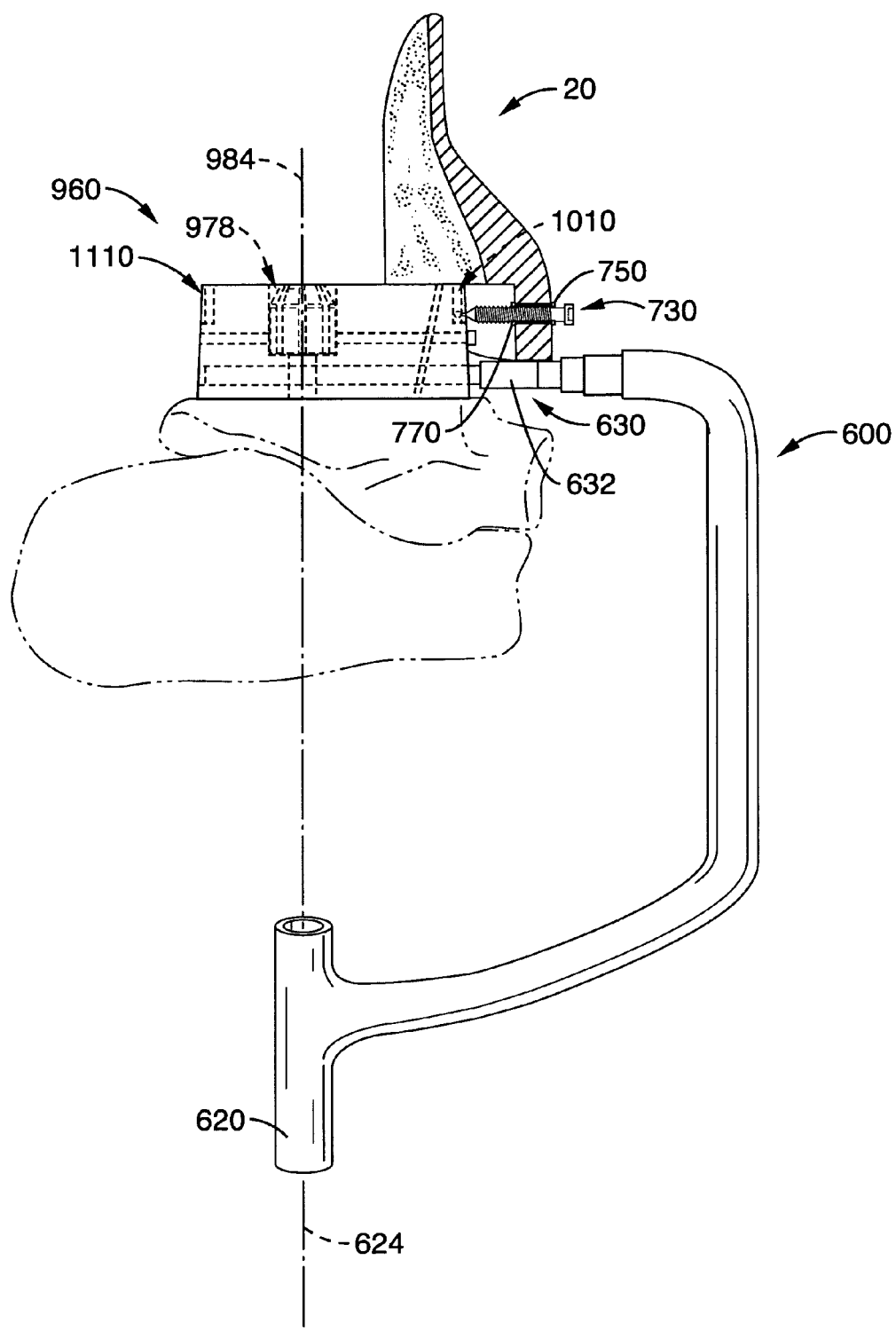
FIG. 86 is a side elevational view of the reversible tibial reaming guide coupled to the adjustment screw in the first orientation and posteriorly adjusted relative to the custom tibial guide illustrated in, for example, FIGS. 37 and 38.

Furthermore, and referring to FIGS. 85 and 86, the reamer body 962 of the tibial reaming guide 960 is comprised of a first interior cylindrical surface 976 that has a first inside circumference that defines a first cylindrically shaped central channel 978 that extends from an opening in the superior face 964 to an annular stepped shoulder 980 (FIG. 86) disposed substantially parallel to the superior face 664. The annular stepped shoulder 980 forms an axially directed stop surface 982. A central longitudinal axis 984 of the first cylindrically shaped central channel 978 is substantially perpendicular to both the superior face 964 and the annular stepped shoulder 980. The open ended cylindrically shaped central channel 978 is sized to receive the cannulated reaming bit 190 illustrated in FIGS. 11 and 12 and comprised of the axial passage 192 extending through the interior of the cannulated reaming bit 190 and a bone reaming exterior surface comprised of front cutting threads 194 and side cutting threads 196.

Still referring to FIGS. 85 and 86, the tibial reaming guide 960 is further comprised of a second interior surface 986 that has a second inside circumference less than the first inside circumference of said first interior cylindrical surface 976 and defines a second central channel 988 that extends from an opening in the annular stepped shoulder 980 to an opening in the inferior face 966. Accordingly, the first cylindrically shaped central channel 978 and the second central channel 988 are in open communication with one another and in open communication between the openings in the superior face 964 and the inferior face 966. Additionally, the central longitudinal axis 984 of the first cylindrically shaped central channel 978 is also the central longitudinal axis of the second central channel 988 thereby defining a coaxial relationship between the two. Furthermore, and in one embodiment, the second central channel 988 comprises a cylindrically shaped second interior surface 986 or, in another embodiment, a conically shaped second interior surface 986 with an inferior end having a wider diameter and tapering to a narrower diameter at the level of the annular stepped shoulder 980, with the conical shape guiding the reamer driver 416 to the opening at the annular stepped shoulder 980 having a diameter large enough to allow passage therethrough.

Moreover, and in one situation, the central longitudinal axis 984 aligns or is coincident with the central axis 302 of the tibia 300 when the trapezoidally shaped anterior face 974 of the reamer body 962 abuts against the trapezoidally shaped posterior surface portion 44 of the reaming guide locator notch 46 and when the custom tibial cutting guide 20 is placed against the anterior surface portion 306 of the distal portion 304 of the tibia 300 with a portion of the reamer body 962 received within the tibial-talar space 342. Thus, when the cannulated reaming bit 190 is received within the first cylindrically shaped central channel 978, the shape of the custom tibial cutting guide 20 and the depth of the locator notch 46 in its distal end combine to set the alignment of the axial passage 192 of the cannulated reaming bit 190 with the central axis 302 of the tibia 300 for reaming of the tibia 300 along its central axis 302 with the reaming exterior front and side cutting threads 194, 196 of the cannulated reaming bit 190. The diameter of the first cylindrically shaped central channel 978 of the reamer body 962 is sized to closely receive the cannulated reamer bit 190 and the annular stepped shoulder 980 forms the axially directed stop surface 982 for supporting the cannulated reamer bit 190. The cannulated reamer bit 190 is of the size needed to ream the tibial blind bore 328 for the size of the tibial stem or, in one embodiment, the modular tibial stem components 372 of the size of the preoperatively chosen prosthesis 370.

Attachment Channels 990, 992 and Fixation Pin Holes 994, 1094

Referring now to FIGS. 85 through 88, the reamer body 962 of the custom tibial reaming guide 960 is comprised of two attachment channels 990, 992 that extend completely through the reamer body 962 for respectively receiving the spaced apart furcations or tines 638, 640 of the forked end portion 636 of the tuning forked shaped adapter 630 (FIG. 54) by way of the openings of the respective channels 990, 992 disposed in the anterior face 974 or in the posterior face 972 of the reamer body 962. The two attachment channels 990, 992 also have a width of separation between the channels 990, 992 corresponding to the width of separation between the tines 638, 640 on the corresponding tuning fork adapter 630.

Additionally, the reamer body 962 of the custom tibial reaming guide 960 is comprised of a fixation pin hole or channel 1094 that passes from the posterior surface 972 of the tibial reaming guide 960 into the central channel 978 with a diameter large enough to allow passage of the fixation pin 696. Again, the fixation pin 696 engages the tibial reaming bit 190 when it sits on the ledge 982 in the central channel 978 of the tibial reaming guide 960. This engagement stabilizes the tibial reaming bit 190 within the central channel 978. Accordingly, the use and operation of the fixation pin 696 with the tibial reaming bit 190 when placed within the central channel 978 is analogous to that which has been delineated above with respect to the use and operation of the fixation pin 696 with the tibial reaming bit 190 when placed within the central channel 678.

Oblique Channels for Fixation to Custom Tibial Guide and Talus

Referring to FIGS. 85 and 86, an embodiment of the custom tibial reaming guide 960 comprises a pair of parallel oblique channels 1006, 1007 that pass from the anterior superior surface 964 of the tibial reaming guide 960 and exit the inferior surface 966 more posteriorly, each with a diameter large enough for passage of a fixation pin 704 (FIG. 58).

Vertical Grooves 1010 and 1110

Still referring to FIGS. 85 and 86, an embodiment of the tibial reaming guide 960 comprises a vertically elongated groove 1010 in the anterior face 974 of the tibial reaming guide 960. The vertically elongated groove 1010 comprises a vertically extending domed shaped interior sidewall surface 1012 vertically extending between a superior arcuate shaped opening 1014 in the superior face 964 to an interior arcuate shaped closed end 1016. The vertically extending domed shaped interior sidewall surface 1012 transitions into a vertically extending base comprised of a lateral anterior flange 1018 and a central anterior flange 1020 extending toward, but spaced from one another for defining an anterior rectangular opening 1022 extending between the superior arcuate shaped opening 1014 and the interior arcuate shaped closed end 1016. The lateral anterior flange 1018 and the central anterior flange 1020 make the anterior rectangular opening 1022 of the vertically elongated groove 1010 narrower than the interior depths or, in other words, narrower than the interior diameter of the vertically extending domed shaped interior sidewall surface 1012 at the base location. The function of this narrowing is the same as delineated above with reference to the tibial reaming guide 960.

Figure 87:
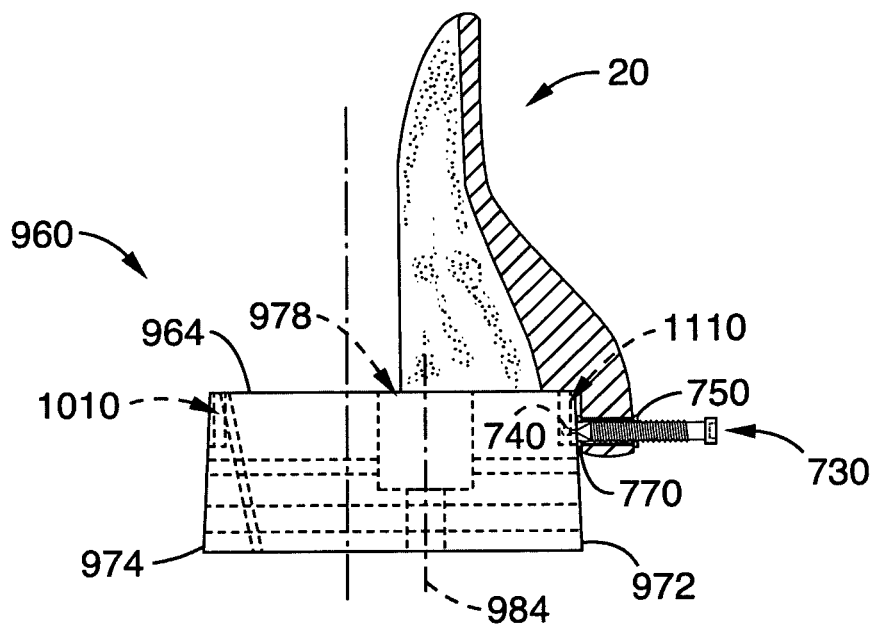
FIG. 87 is a side elevational view of the reversible tibial reaming guide coupled to the adjustment screw in a second orientation (rotated one-hundred-eighty degrees from the first orientation) and abutting the posterior locator notch of the custom tibial guide illustrated in, for example, FIGS. 37 and 38.
Figure 88:
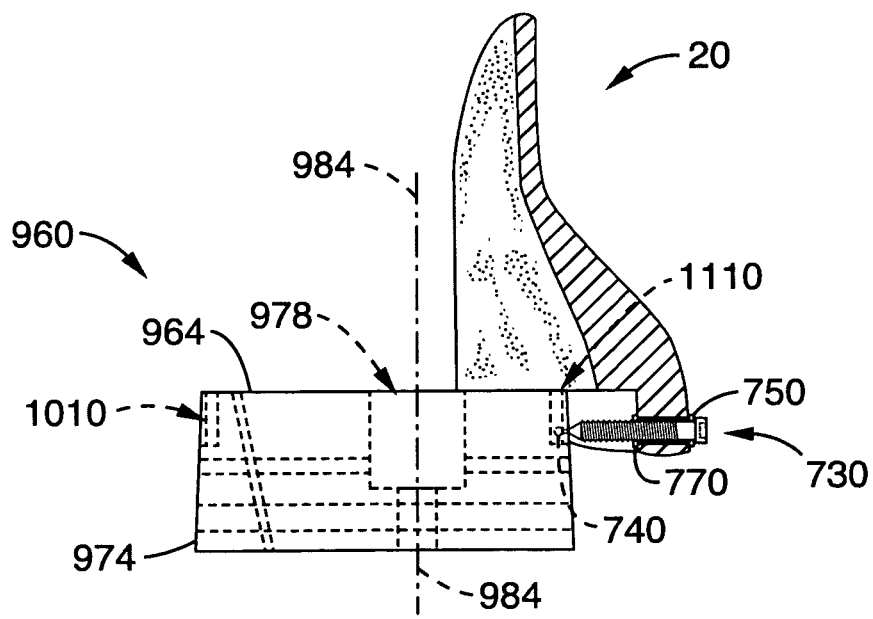
FIG. 88 is a side elevational view of the reversible tibial reaming guide coupled to the adjustment screw in the second orientation and posteriorly adjusted relative to the custom tibial guide illustrated in, for example, FIGS. 37 and 38.

Referring to FIGS. 87 and 88, an embodiment of the tibial reaming guide 960 further comprises a vertically elongated groove 1110 in the posterior face 972 of the tibial reaming guide 960. The vertically elongated groove 1110 comprises a vertically extending domed shaped interior sidewall surface 1112 vertically extending between a superior arcuate shaped opening 1114 in the posterior face 972 to an interior arcuate shaped closed end 1116. The vertically extending domed shaped interior sidewall surface 1112 transitions into a vertically extending base comprised of a lateral anterior flange 1118 and a central anterior flange 1120 extending toward, but spaced from one another for defining a rectangular opening 1122 in the posterior face 972 that extends between the superior arcuate shaped opening 1114 and the interior arcuate shaped closed end 1116. The lateral anterior flange 1118 and the central anterior flange 1120 make the rectangular opening 1122 of the vertically elongated groove 1110 narrower than the interior depths or, in other words, narrower than the interior diameter of the vertically extending domed shaped interior sidewall surface 1112 at the base location. The function of this narrowing is the same as delineated above with reference to the tibial reaming guide 960.

Reversible Tibial Reaming Guide Use and Operation

In use and operation, and referring to FIGS. 87 through 91, the reversible tibial reaming guide 960 can be utilized intraoperatively to perform like the tibial reaming guide 660 or reversed to perform like the anteriorly truncated tibial reaming guide 860 by providing an offset central channel 978 such that a distance 1030 (or a) between a superior edge of the anterior face 974 to the center of the central channel 978 is shorter than a distance 1032 (or b) between a superior edge of the posterior face 972 to the center of the central channel 878. Accordingly, both the anterior and posterior positions of the reversible tibial reaming guide 960 can be adjusted intraoperatively if the surgeon determines that the alignment provided by the guide 960 is not proper.

More specifically, the reversible tibial reaming guide 960 can be used like tibial reaming guide 660 to interact with the custom tibial guide 20 in the fashion when the anterior face 974 is positioned against the custom tibial guide 20. When used in this same position with the anterior face 974 against the custom tibial guide 20, the reversible tibial reaming guide 960 can be moved posteriorly like tibial reaming guide 660 described previously with the body 962 attaching to the adjustment screw 730 by the bulbous end 740 of screw 730 passing through the opening 1014 and into the vertically elongated domed shaped groove 1010 while the neck of the screw 730 slides down the rectangular opening 1022 disposed trough the anterior face 974 of the reaming guide 960.

Figure 89:
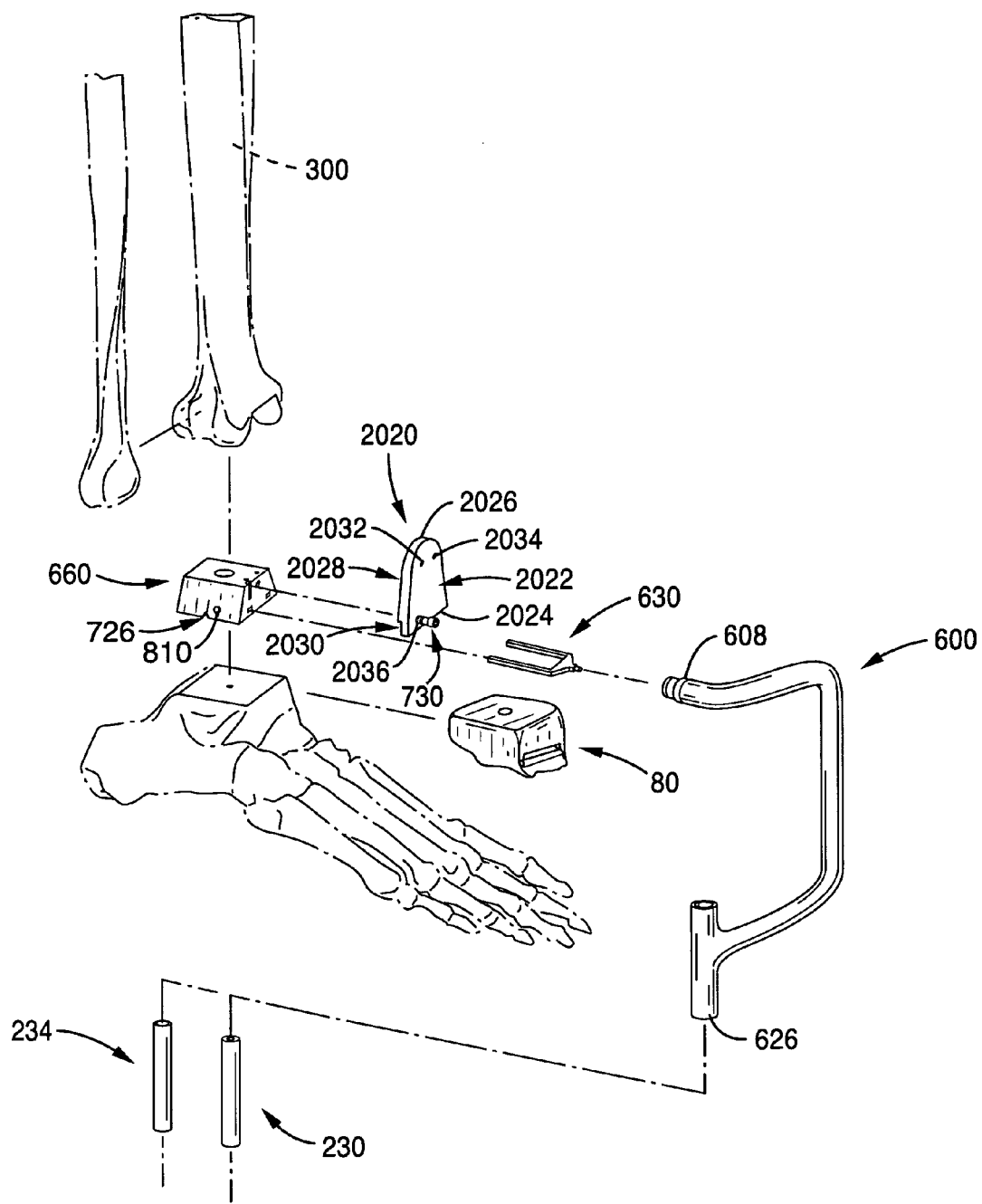
FIG. 89 is a front and side perspective view of another embodiment of a system for use in total ankle replacement surgery with a non-custom tibial cutting guide.

Turning the screw will push the reversible tibial reaming body 962 posteriorly, so that the central axis 984 of the central channel 978 can be relocated to a more posterior position as illustrated in FIG. 89.

Additionally, and as illustrated in FIGS. 90 and 91, the reversible tibial reaming guide 960 can be reversed to perform like the anteriorly truncated tibial reaming guide 860. In that case, the posterior face 972 of the reversible tibial reaming guide 960 is against the custom tibial guide 20 and the central channel 978 is more anteriorly located with the body 962 attaching to the adjustment screw 730 by the bulbous end 740 of screw 730 passing through the opening 1114 and into the vertically elongated domed shaped groove 1110 while the neck of the screw 730 slides down the rectangular opening 1122 disposed trough the posterior face 972 of the reaming guide 960.

Turning the screw will push the reversible tibial reaming body 962 posteriorly, but with the central axis 984 having been brought anteriorly by reversing the body 962 the central axis 984 can be positioned over a range anterior to the positions established with tibial reaming guide 660.

It is preferred that during these maneuvers the alignment of the distal sleeve 620 of the C-shaped outrigger alignment guide 600 with the reamer bit 190 in the tibial reaming guide 960 remains constant. For example, and as shown in FIG. 92, the central axis 984 of the reversible tibial reaming guide 960, and the center of the tibial reaming bit 190 remains aligned with the central axis 624 of the distal sleeve 620 of the C-shaped outrigger alignment guide 600 when it is attached through the tuning fork shaped adapter 630, even when the tibial reaming guide, in this figure the reversible tibial guide 960, is pushed posteriorly by way of the adjustment screw 730 as delineated above.

Anterior Tibial Guide 2020

Illustrated in FIG. 89, instead of a custom tibial guide, there is an anterior tibial guide 2020 that has a pyramidal shaped body 2022 with an inferior base 2024 wider than a superior end 2026. An interior surface 2028 has a gently curved shape that is roughly congruent with the surface of the anterior distal tibia. On an inferior deep surface there is a notch 2030 that a second instrument, for example, tibial reaming guide 660, 860, or 960, can slide under. Anterior tibial guide 2020 is provided with holes 2032, 2034 through the body 2022 of the anterior tibial guide 2020 that can be used to temporarily fix it in place against the tibial bone using thin wires or screws.

Adjustment screw 730, as delineated above, fits through a threaded hole 2036 in a lower portion of the body 2022 of the anterior tibial guide 2020 at the level of the tibial reaming guide 660, 860, or 960. As delineated above, the adjustment screw 730 attaches to one of the grooves 710, 910, 1010, or 1110 of the respective tibial reaming guides 660, 860, or 960.

Turning the adjustment screw 730 in one direction will draw the tibial reaming guide 660, 860, or 960 anterior toward the deep surface or notch 2030 of the anterior tibial guide 2020. Turning the adjustment screw 730 in the opposite direction will push the tibial reaming guide 660, 860, or 960 posterior, away from the deep surface or notch 2030 anterior tibial guide 2020.

In use and operation, the anterior tibial guide 2020 is placed against the anterior surface of the distal tibia with the tibial reaming guide, for example, 660, 860, or 960 attached to it through the adjustment screw 730. An intra-operative fluoroscopy unit would be placed such that the beam would travel from medial to lateral across the ankle. The lateral radiographic alignment guide 810 built into the tibial reaming guide would be used to align the beam of the fluoroscopy unit so that it would show a true lateral view of the tibial reaming guide. The tibial reaming guide is held in the ankle mortise by the prior bone cuts delineated above in detail. Thus, the fluoroscopy unit position would be a true lateral view of the ankle mortise.

The mark, for example, 726, 926, or 1026 built into the respective tibial reaming guide 660, 860, or 960 that corresponds to the central axis of the respective central channel would be visible under this lateral fluoroscopy view. If the tibial reaming guide, for example, 660, 860, or 960 was moved anteriorly or posteriorly the movement of the mark would be seen, indicating the position of the central axis of the central channel, and the enclosed reamer bit 190.

The proper alignment of that central axis would be determined on the lateral fluoroscopy view by turning the thumbscrew one way or the other, and moving the tibial reaming guide, for example, 660, 860, or 960 anteriorly or posteriorly until the proper position aligned with the central axis of the tibia was obtained.

The anterior inferior surface of the tibial reaming guide, for example, 660, 860, or 960 then attaches through the friction fitting with the outrigger alignment guide 600 that has a drill sleeve at its inferior end. The anterior tibial guide 2020 and the proximal part of the outrigger alignment guide 600 by its attachment to the tibial reaming guide can be temporarily fixed into the underlying bone to maintain the proper position of the instruments.

Then the tibial reaming may continue as described above with the proper alignment along the central axis of the distal tibia. A wire is first drilled into the tibia through the distal drill sleeve in the outrigger alignment guide 600 and up through the cannulated drill bit in the central channel of the tibial reaming guide. Then a cannulated drill bit opens a wider channel up to the base of the tibial reaming guide. Finally, a reamer passes through this channel and engages the cannulated reamer bit 190 in the central channel. The distal tibia is then reamed along the central axis of the distal tibia.

The above detailed description of the systems and instrumentalities for use in total ankle replacement surgery, including their use and operation, demonstrate the industrial applicability of this invention.

Moreover, having thus described this instant invention, it should be apparent that numerous modifications and adaptations may be resorted to without departing from the scope and fair meaning of this instant invention as set forth hereinabove and as described hereinbelow by the claims.

I claim:

1. An adjustable tibial reaming guide positioning system for allowing a position for reaming of a distal tibia to be adjusted during total ankle arthroplasty for prostheses with an intramedullary stem, said system comprising:

a tibial reaming guide having a reamer body sized to fit in a space formed by a resected segment of a distal portion of a tibia and a resected segment of a dome of a talus, said reamer body having an opened ended channel for removeably receiving a cannulated tibial reaming bit, said opened ended channel having a central longitudinal axis; and means, operatively coupled to said tibial reaming guide, for incrementally adjusting a position of said tibial reaming guide in the space formed by the resected segment of the distal portion of the tibia and the resected segment of the dome of the talus for locating said central longitudinal axis of said opened ended channel of said tibial reaming guide relative to a central longitudinal axis of the distal portion of the tibia during total ankle arthroplasty for prostheses with an intramedullary stem.

2. The system of claim 1 wherein said adjusting means comprises a grove disposed in an anterior face of said reamer body of said tibial reaming guide and an adjustment screw operatively coupled to said grove and threadedly coupled to an internally threaded opening disposed through a tibial guide located on an anterior of the distal portion of the tibia wherein turning said adjustment screw repositions said central longitudinal axis of said opened ended channel of said tibial reaming guide and the cannulated tibial reaming bit received within said opened ended channel from a first position to a second position different than said first position.

3. The system of claim 2 wherein said grove is defined by a vertically extending domed shaped interior sidewall surface disposed in said anterior face of said reamer body of said tibial reaming guide, said vertically extending domed shaped interior sidewall surface extending between a superior arcuate shaped opening in a superior face of said reamer body of said tibial reaming guide to an interior arcuate shaped closed end.

4. The system of claim 3 wherein said vertically extending domed shaped interior sidewall surface transitions into a vertically extending base comprised of a lateral anterior flange and a central anterior flange extending toward, but spaced from one another for defining an anterior rectangular opening interposed between said lateral and central anterior flanges and extending between said superior arcuate shaped opening and said interior arcuate shaped closed end.

5. The system of claim 4 wherein said adjustment screw comprises an elongated shank having a drive head at a first end and a narrow neck at a second end transitioning into a bulbous tip of said adjustment screw, said elongated shank having exterior threads extending between an area below said drive head and said narrow neck and complemental to said internally threaded opening, and wherein said bulbous tip is sized to fit within said grove disposed in said anterior face of said reamer body of said tibial reaming guide by way of said superior arcuate shaped opening and wherein said neck is sized to fit between said lateral and central anterior flanges while disallowing said bulbous tip from passing therethrough.

6. The system of claim 5 wherein said internally threaded opening disposed through the tibial guide is formed by a threaded interior surface of a hole passing through the tibial guide.

7. The system of claim 5 wherein said internally threaded opening disposed through the tibial guide is formed by a threaded interior surface of a sleeve member fitted within a hole passing through the tibial guide.

8. The system of claim 1 wherein said reamer body further comprises an annular stepped shoulder disposed within said opened ended channel and partitioning said opened ended channel into a first open ended channel superior to said annular stepped shoulder and a second open ended channel inferior to said annular stepped shoulder, said annular stepped shoulder forming an axially directed stop surface for the cannulated reaming bit removeably received within first open ended channel to axially abut against.

9. The system of claim 1 further comprising an alignment guide comprising a generally arcuate body having a medial section transitioning into a superior end supporting a tuning forked shaped adaptor and into an inferior end supporting a sleeve attachment wherein said tuning forked shaped adaptor is comprised of a body extending from said superior end of said generally arcuate body and transitioning into spaced apart furcations received within spaced apart channels disposed within said reamer body of said tibial reaming guide for aligning a longitudinal axis of said sleeve attachment with said central longitudinal axis of said tibial cutting guide when said body of said tuning forked shaped adaptor abuts against an anterior face of said body of said tuning forked shaped adaptor.

10. The system of claim 1 wherein said reamer body of said tibial reaming guide comprises a lateral radiographic marker aligned with said central longitudinal axis of said opened ended channel of said tibial reaming guide for identifying with intra-operative fluoroscopy if a position of said central longitudinal axis of said opened ended channel of said tibial reaming guide is properly positioned for reaming the distal portion of the tibia.

11. The system of claim 10 wherein said radiographic marker is in a form of groove disposed in an inferior face of said reamer body of said tibial reaming guide, said groove having a cleft in an outer face and in an inner face of said reamer body of said tibial reaming guide.

12. The system of claim 1 wherein said reamer body of said tibial reaming guide has a first length between a superior edge of an anterior face of the reamer body and said central longitudinal axis of said opened ended channel which is less than a second length between a superior edge of a posterior face of said reamer body and said central longitudinal axis of said opened ended channel.

13. The system of claim 1 wherein said reamer body of said tibial reaming guide has a first length between a superior edge of an anterior face of the reamer body and said central longitudinal axis of said opened ended channel which is substantially equal to a second length between a superior edge of a posterior face of said reamer body and said central longitudinal axis of said opened ended channel.

14. The system of claim 1 wherein said reamer body of said tibial reaming guide has a first length between a superior edge of an anterior face of the reamer body and said central longitudinal axis of said opened ended channel which is greater than a second length between a superior edge of a posterior face of said reamer body and said central longitudinal axis of said opened ended channel.

15. The system of claim 1 wherein said adjusting means comprises an anterior face grove disposed in an anterior face of said reamer body, a posterior face grove disposed in a posterior face of said reamer body, and an adjustment screw operatively coupled to said anterior face grove when said reamer body is in a first position and to said posterior face grove when said reamer body is in a second position rotated about one-hundred-eight degrees from said first position.

16. The system of claim 15 wherein said adjustment screw is threadedly coupled to an internally threaded opening disposed through a tibial guide located on an anterior of the distal portion of the tibia wherein turning said screw repositions said central longitudinal axis of said opened ended channel of said tibial reaming guide and a tibial reaming bit received within said opened ended channel from a first position to a second position different than said first position.

* * * * *